(12) United States Patent
Eder et al.

(10) Patent No.: US 10,465,011 B2
(45) Date of Patent: Nov. 5, 2019

(54) FACTOR XI ANTIBODIES AND METHODS OF USE

(71) Applicant: Novartis AG, Basel (CH)

(72) Inventors: Jorg Eder, Rheinfelden (DE); Stefan Ewert, Geroldswill (DE); Ulrich Hassiepen, Lorrach (DE); Yasser Khder, Hesingue (FR); Lorenz Mayr, Binen (DE); Samu Melkko, Zurich (CH); Nikolaus Schiering, Weil am Rhein (CH)

(73) Assignee: Novartis AG, Basel (CH)

( * ) Notice: Subject to any disclaimer, the term of this patent is extended or adjusted under 35 U.S.C. 154(b) by 243 days.

(21) Appl. No.: 15/192,020

(22) Filed: Jun. 24, 2016

(65) Prior Publication Data

US 2017/0022292 A1  Jan. 26, 2017

Related U.S. Application Data

(60) Provisional application No. 62/184,955, filed on Jun. 26, 2015, provisional application No. 62/341,568, filed on May 25, 2016.

(51) Int. Cl.

| A61K 39/395 | (2006.01) |
| C07K 16/36 | (2006.01) |
| C07K 16/40 | (2006.01) |
| A61P 7/02 | (2006.01) |
| A61K 45/06 | (2006.01) |
| A61K 39/00 | (2006.01) |

(52) U.S. Cl.
CPC .......... *C07K 16/36* (2013.01); *A61K 39/3955* (2013.01); *A61K 45/06* (2013.01); *A61P 7/02* (2018.01); *C07K 16/40* (2013.01); *A61K 2039/505* (2013.01); *C07K 2317/21* (2013.01); *C07K 2317/55* (2013.01); *C07K 2317/56* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| 4,399,216 A | 8/1983 | Axel et al. |
| 4,439,196 A | 3/1984 | Higuchi |
| 4,447,224 A | 5/1984 | DeCant, Jr. et al. |
| 4,447,233 A | 5/1984 | Mayfield |
| 4,486,194 A | 12/1984 | Ferrara |
| 4,487,603 A | 12/1984 | Harris |
| 4,596,556 A | 6/1986 | Morrow et al. |
| 4,634,665 A | 1/1987 | Axel et al. |
| 4,790,824 A | 12/1988 | Morrow et al. |
| 4,816,397 A | 3/1989 | Boss et al. |
| 4,816,567 A | 3/1989 | Cabilly et al. |
| 4,941,880 A | 7/1990 | Burns |
| 4,946,778 A | 8/1990 | Ladner et al. |
| 4,963,657 A | 10/1990 | Pixley |
| 5,064,413 A | 11/1991 | McKinnon et al. |
| 5,179,017 A | 1/1993 | Axel et al. |
| 5,223,409 A | 6/1993 | Ladner et al. |
| 5,225,539 A | 7/1993 | Winter |
| 5,312,335 A | 5/1994 | McKinnon et al. |
| 5,383,851 A | 1/1995 | McKinnon, Jr. et al. |
| 5,399,163 A | 3/1995 | Peterson et al. |
| 5,403,484 A | 4/1995 | Ladner et al. |
| 5,545,806 A | 8/1996 | Lonberg et al. |
| 5,569,825 A | 10/1996 | Lonberg et al. |
| 5,571,698 A | 11/1996 | Ladner et al. |
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,648,260 A | 7/1997 | Winter et al. |
| 5,661,806 A | 8/1997 | Lonberg et al. |
| 5,959,083 A | 9/1999 | Bosslet et al. |
| 6,005,091 A | 12/1999 | Blackburn et al. |
| 7,217,794 B2 | 5/2007 | Abdel-Meguid et al. |
| 7,459,564 B2 | 12/2008 | Corte et al. |
| 7,501,404 B2 | 3/2009 | Bannister et al. |
| 7,544,699 B2 | 6/2009 | Mjalli et al. |
| 7,626,039 B2 | 12/2009 | Pinto et al. |
| 7,645,799 B2 | 1/2010 | Corte et al. |
| 7,842,708 B2 | 11/2010 | Pinto et al. |
| 8,236,316 B2 | 8/2012 | Gruber et al. |
| 8,324,199 B2 | 12/2012 | Corte et al. |
| 8,388,959 B2 | 3/2013 | Gruber et al. |

(Continued)

FOREIGN PATENT DOCUMENTS

| EP | 0 125 023 A1 | 11/1984 |
| EP | 0 171 496 A2 | 2/1986 |

(Continued)

OTHER PUBLICATIONS

Kipriyanov et al., Mol Biotechnol. Jan. 2004;26(1):39-60.*
Reagents, "Supplemental Methods and Data" (Jan. 13, 2015), URL:http://www.bloodjournal.org/content/bloodjournal/suppl/2015/01/13/blood-2014-10-604587.DC1/blood-2014-10-604587-1.pdf.
Akiyama, Hideki, et al., "Mechanism of Activation of Coagulation factor XI by by Factor XIIa Studied with monoclonal Antibodies", J. Clin. Invest, 78:1631-1637. 1986.
Al-Horani & Umesh, "Factor XIa inhibitors: A review of the patent literature", Expert opinion on Therapeutic Patents, 26 (3):323-345. 2016.
Minnema, et al., "Activation of Clotting Factors XIand IX in Patients With Acute Myocardial Infarction", Arterioscler Thromb Vasc Biol, 20:2489-2493. 2000.
Bern et al., Treatment of factor XI inhibitor using recombinant factor VIIa, Haemophilia, 11:20-25. 2005.

(Continued)

*Primary Examiner* — Michael Szperka
(74) *Attorney, Agent, or Firm* — Finnegan, Henderson, Farabow, Garrett & Dunner LLP

(57) ABSTRACT

The present invention relates to monoclonal antibodies and antigen binding fragments thereof that bind to human Factor XI and activated Factor XI ("Factor XIa"), and pharmaceutical compositions and methods of treatment comprising the same.

16 Claims, 10 Drawing Sheets

Specification includes a Sequence Listing.

(56) References Cited

U.S. PATENT DOCUMENTS

| | | |
|---|---|---|
| 8,399,648 B2 | 3/2013 | Gruber et al. |
| 8,568,724 B2 | 10/2013 | Hack |
| 8,940,833 B2 | 1/2015 | Schmitt et al. |
| 9,125,895 B2 | 9/2015 | Gruber et al. |
| 9,636,399 B2 | 5/2017 | Gruber et al. |
| 9,637,550 B2 | 5/2017 | Gruber et al. |
| 9,783,614 B2 | 10/2017 | Wilmen et al. |
| 10,053,515 B2 | 8/2018 | Chen et al. |
| 10,221,247 B2 | 3/2019 | Wilmen et al. |
| 2004/0180855 A1 | 9/2004 | Shumacher et al. |
| 2005/0059705 A1 | 3/2005 | Mjalli et al. |
| 2005/0143317 A1 | 6/2005 | Abdel-Megui et al. |
| 2006/0154915 A1 | 7/2006 | Corte et al. |
| 2007/0105832 A1 | 5/2007 | Bannister et al. |
| 2008/0146811 A1 | 6/2008 | Deng et al. |
| 2008/0161373 A1 | 7/2008 | Pinto et al. |
| 2009/0062287 A1 | 3/2009 | Corte et al. |
| 2010/0022506 A1 | 1/2010 | Pinto et al. |
| 2010/0137414 A1 | 6/2010 | Freier et al. |
| 2011/0020349 A1 | 1/2011 | Gruber et al. |
| 2011/0021492 A1 | 1/2011 | Corte et al. |
| 2011/0028446 A1 | 2/2011 | Pinto et al. |
| 2011/0159006 A1 | 6/2011 | Hack |
| 2014/0194600 A1 | 7/2014 | Hack |
| 2015/0099298 A1 | 4/2015 | Wilmen et al. |
| 2017/0355780 A1 | 12/2017 | Chen et al. |
| 2018/0022825 A1 | 1/2018 | Ewert et al. |
| 2018/0112009 A1 | 4/2018 | Wilmen et al. |
| 2018/0118850 A1 | 5/2018 | Hack |
| 2018/0216093 A1 | 8/2018 | Goletz et al. |
| 2018/0355056 A1* | 12/2018 | Eder ............ C07K 16/40 |
| 2018/0355057 A1 | 12/2018 | Gruber et al. |
| 2018/0362661 A1 | 12/2018 | Chen et al. |

FOREIGN PATENT DOCUMENTS

| | | |
|---|---|---|
| EP | 0 173 494 A2 | 3/1986 |
| EP | 0 184 187 A2 | 6/1986 |
| EP | 0 338 841 A1 | 10/1989 |
| EP | 0 517 024 A2 | 12/1992 |
| EP | 2 297 207 B1 | 3/2011 |
| EP | 2 297 201 B1 | 10/2018 |
| EP | 3 404 045 A1 | 11/2018 |
| JP | S6265693 A | 3/1987 |
| WO | WO 86/01533 | 3/1986 |
| WO | WO 87/02671 | 5/1987 |
| WO | WO 87/04462 | 7/1987 |
| WO | WO 89/01036 | 2/1989 |
| WO | WO 94/29351 | 12/1994 |
| WO | 1995017420 A1 | 6/1995 |
| WO | 9726010 A1 | 7/1997 |
| WO | WO 00/042072 | 7/2000 |
| WO | WO 02/064634 A2 | 8/2002 |
| WO | WO 02/100348 A2 | 12/2002 |
| WO | WO 03/017935 A2 | 3/2003 |
| WO | WO 03/040169 A2 | 5/2003 |
| WO | WO 2004/035607 A2 | 4/2004 |
| WO | WO 2004/043989 A2 | 5/2004 |
| WO | 04089297 A1 | 10/2004 |
| WO | 04103270 A1 | 12/2004 |
| WO | WO 2004/108749 A2 | 12/2004 |
| WO | 06012504 A1 | 2/2006 |
| WO | WO 2006/040153 A2 | 4/2006 |
| WO | 06076575 A1 | 7/2006 |
| WO | 07070826 A1 | 6/2007 |
| WO | 09067660 A1 | 5/2009 |
| WO | WO 2009/067660 A2 | 5/2009 |
| WO | 2009114677 A1 | 9/2009 |
| WO | 2009154461 A1 | 12/2009 |
| WO | 2010080623 A1 | 7/2010 |
| WO | WO 2010/080623 A2 | 7/2010 |
| WO | 10045509 A1 | 11/2013 |
| WO | 13167669 A1 | 11/2013 |
| WO | WO 2013/167669 A1 | 11/2013 |
| WO | 2016/207858 A1 | 12/2016 |
| WO | WO 2017/015619 A1 | 1/2017 |
| WO | WO 2017/021528 A1 | 2/2017 |
| WO | WO 2017/127468 A1 | 7/2017 |
| WO | 2017/162791 A1 | 9/2017 |
| WO | WO2017162791 A1 | 9/2017 |
| WO | 2017/203450 A1 | 11/2017 |
| WO | 2017/218371 | 12/2017 |
| WO | WO 2018/053597 A1 | 3/2018 |
| WO | WO 2018/054813 A1 | 3/2018 |
| WO | 2018/116255 A1 | 6/2018 |
| WO | 2018/116267 A1 | 6/2018 |
| WO | WO 2018/134184 A1 | 7/2018 |

OTHER PUBLICATIONS

Wuillemin, et al., "Thrombin-mediated activation of endogenous factor XI in plasma in the presence of physiological glycosaminoglycans occurs only with high concentrations of thrombin", British Journal of Haematology, 92:466-472. 1996.

De La Cadena, et al., "Naturally Occurring human Antibodies Against Two Distinct Functional Domains in the Heavy Chain of FXI/FXIa", Blood, 72(5):1748-1754. 1988.

Fujikawa, et al., "Amino Acid Sequence of Human factor XI, a Blood Coagulation Factor with Four Tandem Repeats That Are Highly Homologous with Plasma Prekallikrein", Biochemistry, 25:2417-2424. 1986.

Goldsmith and Silverman, "Inhibitors of plasma thromboplastin antecedent (factor XI): Studies on mechanism of Inhibition", J Lab. Clin Med. 106(3):279-285. 1985.

Gruber and Hanon, "Factor XI-dependence of surface- and tissue factor-initiated thrombus propagation in primates", Blood, 102(3):953-955. 2003.

Halvoet et al., "Measurement of Free, one-Chain Tissue-Type Plasminogen Activator in Human Plasma With an Enzyme-Linked Immunosorbent Assay Based on an Active Site-Specific Murine Monoclonal Antibody", Blood, 69 (1):284-289. 1987.

Naito and Fujikawa, "Activation of Human Blood Coagulation Factor XI Independent of Factor XII", The Journal of Biological Chemistry, 266(12):7353-7358. 1991.

Jin et al., "Crystal Structures of the FXIa catalytic Domain in Complex with Ecotin Mutants Reveal Substrate-like Interactions", The Journal of Biological Chemistry, 280(6):4704-4712. 2005.

Kravtsov et al., "Factor XI contributes to thrombin generation in the absence of factor XII", Blood, 114(2): 452-458. 2009.

Minnema et al., "Enhancement of Rabbit Jugular Vein thrombolysis by neutralization of factor XI in Vivo Evidence for Role of Factor XI as an Anti-fibrinolytic Factor", J. Clin. Invest., 101(1):10-14. 1998.

Morgan et al., "Acquired Factor XI Inhibitors in Two Patients with Hereditary Factor XI Deficiency", Thromb Haemostas, 51(3):371-375. 1984.

Nishikado et al., "Murine Monoclonal Antibodies to Human Factor XI", Thrombosis Research, 42:225-234. 1986.

Ohkubo et al., "Characterization of a Panel of Monoclonal Antibodies to Human Coagulation Factor XI and Detection of Factor XI in Hep G2 Cell Conditioned Medium", Thrombosis and Haemostasis, 63(3):4170423. 1990.

Konings et al., "Ongoing Contact Activation in Patients with Hereditary Angioedema", PLOS ONE, 8(8):1-9. 2013.

Renne et al., "Factor XI deficiency in animal models", Journal of Thrombosis and Haemostasis, 7(Suppl. 1):79-83. 2009.

Salomon et al., "Prevalence, causes, and characterization of factor XI inhibitors in patients with inherited factor XI deficiency", Blood, 101(12):4783-4788. 2003.

Samuel et al., "Solution structure of the A4 domain of factor XI sheds light on the mechanism of zymogen activation", PNAS, 104(40):15693-15698. 2007.

Shumacher et al., "Antithrombotic and hemostatic effects of a small molecule factor XIa inhibitor in rats", European Journal of Pharmacology, 570:167-174. 2007.

Scott et al., "Amidolytic Assay of Human Factor XI in Plasma: Comparison With a coagulant Assay and a new Rapid Radioimmunoassay", Blood, 63(1):42-50. 1984.

(56) References Cited

OTHER PUBLICATIONS

Sie et al., "An Acquired Antithrombin Autoantibody Directed toward the Catalytic Center of the Enzyme", J. Clin. Invest., 88:290-296. 1991.
Sinha et al., "Functional Characterization of Human Blood Coagulation factor XIa Using Hybridoma Antibodies", The Journal of Biological Chemistry, 260(19):10714-10719. 1985.
Stern et al., "Acquired Antibody to Factor XI in a Patient with Congenital factor XI Deficiency", J. Clin. Invest., 39:1270-1276. 1982.
Tucker et al., "Prevention of vascular graft occlusion and thrombus-associated thrombin generation by inhibition of factor XI", Blood, 113(4):936-944. 2009.
Spronk et al., "Monitoring thrombin generation: Is addition of corn trypsin inhibitor needed", Throm Haemost, 101:1156-1162. 2009.
Minnema et al., "Activation of the contact System of Coagulation Does Not Contribute to the Hemostatic Imbalance in Hypertriglyceridemia", Arterioscler Throm Vasc Biol. 19:2548-2553. 1999.
Wuillemin et al., "Activation of the Intrinsic Pathway of Coagulation in Children with Meningococcal Septic Shock", Thrombosis and Haemostasis, 74(6):1436-41. 1995.
van Montfoort and Meijers, "Anticoagulation beyond direct thrombin and factor Xa inhibitors: indications for targeting the intrinsic pathway", Thrombosis and Haemostasis, 110(2):223-232. 2013.
van Montfoort, "Factor XI as target for antithrombotic therapy", Thesis. 2014.
Yamashita et al., "Factor XI contributes to thrombus propagation on injured neointima of the rabbit iliac artery", Journal of Thrombosis and Haemostasis, 4:1496-1501. 2006.
Zucker et al., "Induction of an inhibitor antibody to factor XI in a patient with severe inherited factor XI deficiency by Rh Immune globulin", Blood, 111(3):1306-1308. 2008.
Matafonov et al., "Evidence for factor IX-independent roles for factor XIa in blood coagulation", J Thromb Haemost 11 (12):2118-2127 (2013).
Puy et al., "Activated factor XI increases the procoagulant activity of the extrinsic pathway by inactivating tissue factor pathway inhibitor", Blood, 125(9):1488-1496 (2015).
van Montfoort et al., "Two novel inhibitory anti-human factor XI antibodies prevent cessation of blood flow in a murine venous thrombosis model", Thrombosis and Haemostasis, 110(5):1065-1073 (2013).
Yamashita et al., "Favor XI contributes to thrombus propagation on injured neointima of the of the rabbit iliac artery", Journal of Thrombosis and Haemostatis 4:1496-1501 (2006).
Takahashi et al., "Inhibition of factor XI reduces thrombus formation in rabbit jugular vein under endothelial denudation and/or blood stasis", Thrombosis Research, 125(5)464-470 (2010).
David et al., "Factor XIa-specific IgG and a reversal agent to probe factor XI function in thrombosis and hemostasis", Sci. Transl. Med., vol. 8 353ra112 (2016).
Fradera et al., "High-Resolution crystal structures of facrot XIa coagulation factor in complex with nobasic high-affinity synthetic inhibitors", Acta Cryst. F68, 404-408 (2012).
Navaneetham et al., "Structural and Mutational Analyses of the Molecular Interactions between the Catalytic Domain of Factor XIa and the Kunitz Protease Inhibitor Domain of Protease Nexin 2", Journal of Biological Chemistry, 280 (43):36165-36175 (2005).
Jin et al., "Crystal Structures of the FXIa Catalytic Domain in Complex with Ecotin Mutants Reveal Substrate-like Interactions", Journal of Biological Chemistry, 280(6):4704-4712 (2005).
Baglia, F., et al. "A Binding Site for Thrombin in the Apple 1 Domain of Factor XI", The Journal of Biological Chemistry, 1996 271 (7):3652-3658.
Berge, Stephen M. et al., "Pharmaceutical Salts", Journal of Pharmaceutical Sciences, 1977, 66(1):1-19.

"Efficacy and Safety of MAA868 in Patients with Atrial Fibrillation", ClinicalTrials.gov, U.S. National Library of Medicine [online], https://www.clinicaltrials.gov/ct2/show/NCT03398434?term=maa868&rank=1.
Fanger, Peter M. et al., "Bispecific Antibodies", Critical Reviews in Immunology, 1992, 12(3,4):101-124.
Gailani, David et al., "Model for a factor IX activation complex on blood platelets: dimeric conformation of factor XIa is essential", Blood, 2001, 97(10):3117-3122.
Gailani, D. et al., "A murine model of factor XI deficiency", Blood Coagulation and Fibrinolysis, 1997, vol. 8, pp. 134-144.
Gruber, Andras et al., "Antithrombotic factor XI antibody inhibition of the intrinsic pathway", Blood, 2001 98(11):42a.
Hack, C.E. et al., "Disruption of the internal thioester bond in the third component of complement (C3) results in the exposure of neodeterminants also present on activation products of C3. An analysis with monoclonal antibodies", Journal of Immunology, 1988, 141:1602-1609.
Holliger, Philipp, et al., "Diabodies: Small bivalent and bispecific antibody fragments", Proc Natl. Acad. Sci., 1993, 90:6444-6448.
Kipriyanov, Sergey M. et al., "Generation and Production of Engineered Antibodies", Molecular Biotechnology, 2004, 26:39-60.
Koch, Alexander W., "MAA868, a novel FXI antibody with a unique binding mode, shows durable effects on markers of anticoagulation in humans", Blood, 2019, 133(13): 1507-1516.
Matafonov, A. et al., "Evidence for factor IX-independent roles for factor XIa in blood coagulation", Journal of Thrombosis and Haemostasis, 2013, 11:2118-2127.
Mendez, Michael J. et al., "Functional transplant of megabase human immunoglobulin loci recapitulates human antibody response in mice", Nature Genetics, 1997, 15:146-156.
Minnema M.C. et al., "Activation of Clotting Factor XI Without Detectable Contact Activation in Experimental Human Endotoxemia", Blood, 1998, 92(9):3294-3301.
Peyvandi, Flora et al., "Factor XI deficiency in Iranians: its clinical manifestations in comparison with those of classic hemophilia", Haemtologica, 2002, 87(5):512-514.
"Prevention of Thromboembolic Events in Total Knee Replacement Positions", ClinicalTrials.gov, U.S. National Library of Medicine [online], https://www.clinicaltrials.gov/ct2/show/NCT03393481?term=ma868&rank=2.
Puy, Cristina et al., "Activated factor XI increases the procoagulant activity of the extrinsic pathway by inactivating tissue factor pathway inhibitor", Blood, 2015, 125(9):1488-1496.
Reagents, "Suplemmental Methods and Data", (Jan. 13, 2015), URL: http://www.bloodjournal.org/content/bloodjournal/suppl/2015/01/13/blood-2014-10-604587.DC1/blood-2014-10-604587-1.pdf.
St. Groth, S. Fazekas et al., "Production of Monoclonal Antibodies: Strategy and Tactics", Journal of Immunological Methods, 1980, 35:1-21.
Smeenk, Ruud J. et al., "Is Anticardiolipin Activity a Cross-Reaction of Anti-DNA or a Separate Entity?", Arthritis and Rheumatism, 1987, 30(6): 607-617.
Tait, Jonathan F. et al., "Primary Structure Requirements for the Binding of Human High Molecular Weight Kininogen to Plasma Prekallikrein and Factor XI", Journal of Biological Chemistry, 1987, 262(24): 11651-11656.
Ogawa, Taketoshi et al., "Exosite-mediated Substrate Recognition of Factor XI by Factor XIa", Journal of Biological Chemistry, 2005, 280(25):23523-23530.
Renne, T. et al., "Characterization of the H-kininogen-binding Site on Factor XI", The Journal of Biological Chemistry, 2002, 277(7):4892-4899.
Renne, Thomas et al., "Defective thrombus formation in mice lacking coagulation factor XII", The Journal of Experimental Medicine, 2005, 202(2):271-281.
Sinha, Dipali et al., "Macromolecular Substrate-Binding Exosites on Both the Heavy and Light Chains of Factor XIa Mediate the Formation of the Michaelis Complex Required for Factor IX-Activation", Biochemistry, 2007, 46, 9830-9839.
Strejan, G.H. et al., "Suppression of Chronic-Relapsing Experimental Allergic Encephalomyelitis in Strain-13 Guinea Pigs by Admin-

(56) References Cited

OTHER PUBLICATIONS istration of Liposome-Associated Myelin Basic Protein", *Journal of Neuroimmunology*, 1984, 7:27-41.
Sun, Yuehui et al., "Identification of a Factor IX Binding Site on the Third Apple Domain of Activated Factor XI", *The Journal of Biological Chemistry*, 1996, 271(46):29023-29028.
Takahashi, M. et al., Inhibition of factor XI reduced thrombus formation in rabbit jugular vein under endothelial denudation and/or blood stasis, *Thrombosis Research*, 2010, 125(5):464-470.
Tucker, Erik et al., "Inhibition of Factor XI decreases thrombin production and prevents vascular occlusion in experimental thrombosis in primates", *Blood*, 2007 110(11):1-5.
Van Montfoort, Maurits L. et al., "Two novel inhibitory anti-human factor XI antibodies prevent cessation of blood flow in a murine venous thrombosis model", *Thrombosis and Haemostasis*, 2013, 110:1065-1073.
Yamashita, A. et al., "Factor XI contributes to thrombus propagation on injured neointima of the rabbit iliac artery", *Journal of Thrombosis and Haemostasis*, 2006, 4:1496:1501.
Yang, Mark X. et al., "Crystalline monoclonal antibodies for subcutaneous delivery", *PNAS*, 2003 100(12):6934-6939.
Al-Horani, Rami A. et al., "Designing Allosteric Inhibitors of Factor XIa. Lessons from the Interactions of Sulfated Pentagalloylglucopyranosides", *Journal of Medicinal Chemistry*, ACS Publications, 2014, 57, pp. 4805-4818.
Argade, Malaika D., "Allosteric inhibition of Human Factor XIa: Discovery of Monosulfated Benzofurans as a Class of Promising Inhibitors", *Journal of Medicinal Chemistry*, ACS Publications, 2014, 57, pp. 3559-3569.
Baglia, Frank A., et al., "A Binding Site for Thrombin in the Apple 1 Domain of Factor XI", *The Journal of Biological Chemistry*, vol. 271, No. 7, Feb. 16, 1996, pp. 3652-3658.

Emsley, Jonas et al., "Structure and function of factor XI", *Blood*, vol. 115, No. 13, Apr. 1, 2010, pp. 2569-2577.
Gailani, D. et al., "The Intrinsic pathway of coagulation: a target for treating thromboembolic disease?" *Journal of Thrombosis and Haemostasis*, 2007, 5:1106-1112.
Jin, Lei et al., "Mutation of surface residues to promote crystallization of activated factor XI as a complex with benzamidine: an essential step for the iterative structure-based design of factor XI inhibitors", *Acta Cryst.* (2005) D61, pp. 1418-1425.
Mohammed, Bassem M. et al., "An Update on Factor XI Structure and Function", *Thromb Res.*, Jan. 2018; 161:94-105 (32 pages).
Papagrigoriou, Evangelos et al., "Crystal Structure of the factor XI zymogen reveals a pathway for transactivation", *Nature Structural & Molecular Biology*, vol. 13, No. 6, Jun. 2006, pp. 557-558.
Su, Ya-Chi et al., "The Role of Factor XIa (FXIa) Catalytic Domain Exosite Residues in Substrate Catalysis and Inhibition by the Kunitz Protease Inhibitor Domain of Protease Nexin 2", *The Journal of Biological Chemistry*, vol. 286, No. 36, Sep. 9, 2011, pp. 31904-31914.
Tans, Guido et al., Studies on the effect of serine protease inhibitors on activated contact factors Application in amidolytic assays for factor $XII_a$, plasma kallikrein and factor $XI_a$, Eur. J. *Biochem*, 164, pp. 637-642 (1987).
Wong, Szu S. et al., "A novel DFP tripeptide motif interacts with the coagulation factor XI apple 2 domain", *Blood*, vol. 127, No. 23, Jun. 9, 2016, pp. 2915-2923.
Wu, Yan et al., "Structural insight into distinct mechanisms of protease inhibition by antibodies", *PNAS*, Dec. 11, 2007, vol. 104, No. 50, pp. 19784-19789.
Van Der Graaf, Fedde et al., "Isolation and Functional Characterization of the Active Light Chain of Activated Human Blood Coagulation Factor XI", *The Journal of Biological Chemistry*, 1983, vol. 258, No. 16, pp. 9669-9675.

\* cited by examiner

SEQUENCE LISTING

```
<160> NUMBER OF SEQ ID NOS: 51

<210> SEQ ID NO 1
<211> LENGTH: 625
<212> TYPE: PRT
<213> ORGANISM: Homo sapiens

<400> SEQUENCE: 1

Met Ile Phe Leu Tyr Gln Val Val His Phe Ile Leu Phe Thr Ser Val
1               5                   10                  15

Ser Gly Glu Cys Val Thr Gln Leu Leu Lys Asp Thr Cys Phe Glu Gly
            20                  25                  30

Gly Asp Ile Thr Thr Val Phe Thr Pro Ser Ala Lys Tyr Cys Gln Val
        35                  40                  45

Val Cys Thr Tyr His Pro Arg Cys Leu Leu Phe Thr Phe Thr Ala Glu
    50                  55                  60

Ser Pro Ser Glu Asp Pro Thr Arg Trp Phe Thr Cys Val Leu Lys Asp
65                  70                  75                  80

Ser Val Thr Glu Thr Leu Pro Arg Val Asn Arg Thr Ala Ala Ile Ser
                85                  90                  95

Gly Tyr Ser Phe Lys Gln Cys Ser His Gln Ile Ser Ala Cys Asn Lys
            100                 105                 110

Asp Ile Tyr Val Asp Leu Asp Met Lys Gly Ile Asn Tyr Asn Ser Ser
        115                 120                 125

Val Ala Lys Ser Ala Gln Glu Cys Gln Glu Arg Cys Thr Asp Asp Val
    130                 135                 140

His Cys His Phe Phe Thr Tyr Ala Thr Arg Gln Phe Pro Ser Leu Glu
145                 150                 155                 160
```

```
His Arg Asn Ile Cys Leu Leu Lys His Thr Gln Thr Gly Thr Pro Thr
                165                 170                 175

Arg Ile Thr Lys Leu Asp Lys Val Val Ser Gly Phe Ser Leu Lys Ser
            180                 185                 190

Cys Ala Leu Ser Asn Leu Ala Cys Ile Arg Asp Ile Phe Pro Asn Thr
            195                 200                 205

Val Phe Ala Asp Ser Asn Ile Asp Ser Val Met Ala Pro Asp Ala Phe
        210                 215                 220

Val Ser Gly Arg Ile Cys Thr His His Pro Gly Cys Leu Phe Phe Thr
225                 230                 235                 240

Phe Phe Ser Gln Glu Trp Pro Lys Glu Ser Gln Arg Asn Leu Cys Leu
                245                 250                 255

Leu Lys Thr Ser Glu Ser Gly Leu Pro Ser Thr Arg Ile Lys Lys Ser
            260                 265                 270

Lys Ala Leu Ser Gly Phe Ser Leu Gln Ser Cys Arg His Ser Ile Pro
        275                 280                 285

Val Phe Cys His Ser Ser Phe Tyr His Asp Thr Asp Phe Leu Gly Glu
        290                 295                 300

Glu Leu Asp Ile Val Ala Ala Lys Ser His Glu Ala Cys Gln Lys Leu
305                 310                 315                 320

Cys Thr Asn Ala Val Arg Cys Gln Phe Phe Thr Tyr Thr Pro Ala Gln
                325                 330                 335

Ala Ser Cys Asn Glu Gly Lys Gly Lys Cys Tyr Leu Lys Leu Ser Ser
            340                 345                 350

Asn Gly Ser Pro Thr Lys Ile Leu His Gly Arg Gly Ile Ser Gly
        355                 360                 365

Tyr Thr Leu Arg Leu Cys Lys Met Asp Asn Glu Cys Thr Thr Lys Ile
        370                 375                 380

Lys Pro Arg Ile Val Gly Gly Thr Ala Ser Val Arg Gly Glu Trp Pro
385                 390                 395                 400

Trp Gln Val Thr Leu His Thr Thr Ser Pro Thr Gln Arg His Leu Cys
                405                 410                 415

Gly Gly Ser Ile Ile Gly Asn Gln Trp Ile Leu Thr Ala Ala His Cys
            420                 425                 430

Phe Tyr Gly Val Glu Ser Pro Lys Ile Leu Arg Val Tyr Ser Gly Ile
        435                 440                 445

Leu Asn Gln Ser Glu Ile Lys Glu Asp Thr Ser Phe Phe Gly Val Gln
    450                 455                 460

Glu Ile Ile Ile His Asp Gln Tyr Lys Met Ala Glu Ser Gly Tyr Asp
465                 470                 475                 480

Ile Ala Leu Leu Lys Leu Glu Thr Thr Val Asn Tyr Thr Asp Ser Gln
                485                 490                 495

Arg Pro Ile Cys Leu Pro Ser Lys Gly Asp Arg Asn Val Ile Tyr Thr
            500                 505                 510

Asp Cys Trp Val Thr Gly Trp Gly Tyr Arg Lys Leu Arg Asp Lys Ile
        515                 520                 525

Gln Asn Thr Leu Gln Lys Ala Lys Ile Pro Leu Val Thr Asn Glu Glu
    530                 535                 540

Cys Gln Lys Arg Tyr Arg Gly His Lys Ile Thr His Lys Met Ile Cys
545                 550                 555                 560

Ala Gly Tyr Arg Glu Gly Gly Lys Asp Ala Cys Lys Gly Asp Ser Gly
                565                 570                 575
```

```
Gly Pro Leu Ser Cys Lys His Asn Glu Val Trp His Leu Val Gly Ile
            580                 585                 590

Thr Ser Trp Gly Glu Gly Cys Ala Gln Arg Glu Arg Pro Gly Val Tyr
        595                 600                 605

Thr Asn Val Val Glu Tyr Val Asp Trp Ile Leu Glu Lys Thr Gln Ala
    610                 615                 620

Val
625

<210> SEQ ID NO 2
<211> LENGTH: 3278
<212> TYPE: DNA
<213> ORGANISM: Homo sapiens

<400> SEQUENCE: 2
aggcacacag gcaaaatcaa gttctacatc tgtccctgtg tatgtcactt gtttgaatac     60
gaaataaaat taaaaaaata aattcagtgt attgagaaag caagcaattc tctcaaggta    120
tatttctgac atactaagat tttaacgact ttcacaaata tgctgtactg agagagaatg    180
ttacataaca ttgagaacta gtacaagtaa atattaaagt gaagtgacca tttcctacac    240
aagctcattc agaggaggat gaagaccatt ttggaggaag aaaagcaccc ttattaagaa    300
ttgcagcaag taagccaaca aggtcttttc aggatgattt tcttatatca agtggtacat    360
ttcattttat ttacttcagt ttctggtgaa tgtgtgactc agttgttgaa ggacacctgc    420
tttgaaggag gggacattac tacggtcttc acaccaagcg ccaagtactg ccaggtagtc    480
tgcacttacc acccaagatg tttactcttc actttcacgg cggaatcacc atctgaggat    540
cccacccgat ggtttacttg tgtcctgaaa acagtgttga cagaaacact gccaagagtg    600
aataggacag cagcgatttc tgggtattct ttcaagcaat gctcacacca ataagcgct    660 tgcaacaaag acatttatgt ggacctagac atgaagggca taaactataa cagctcagtt    720
gccaagagtg ctcaagaatg ccaagaagag tgcacggatg acgtccactg ccactttttc    780
acgtacgcca caaggcagtt tcccagcctg gagcatcgta acatttgtct actgaagcac    840
acccaaacag ggacaccaac cagaataacg aagctcgata aagtggtgtc tggatttcca    900
ctgaaatcct gtgcactttc taatctggct tgtattaggg acatttcctcc taatacggtg    960 tttgcagaca gcaacatcga cagtgtcatg gctcccgatg cttttgtctg tggccgaatc   1020
tgcactcatc atccccggttg cttgttttttt accttctttt cccaggaatg gcccaaagaa   1080
tctcaaagaa atctttgtct ccttaaaaca tctgagagtg gattgcccag tacacgcatt   1140
aaaaagagca aagctctttc tggtttcagt ctacaaagct gcaggcacag catcccagtg   1200
ttctgccatt cttcatttta ccatgacact gatttcttgg gagaagaact ggatattgtt   1260
gctgcaaaaa gtcacgaggc ctgccagaaa ctgtgcacca atgccgtccg ctgccagtt   1320 tttacctata ccccagccca agcatcctgc aacgaaggga agggcaagtg ttacttaaag   1380
ctttcttcaa acggatctcc aactaaaata cttcacggga gaggaggcat ctctggatac   1440
acattaaggt tgtgtaaaat ggataatgag tgtaccacca aaatcaagcc caggatcgtt   1500
ggaggaactg cgtctgttcg tggtgagtgg ccgtggcagg tgaccctgca cacaacctca   1560
cccactcaga gacacctgtg tggaggctcc atcattggaa accagtggat attaacagcc   1620
gctcactgtt tctatggggt agagtcacct aagattttgc gtgtctacag tggcatttta   1680
aatcaatctg aaataaaaga ggacacatct ttcctttgggg ttcaagaaat aataatccat   1740
gatcagtata aaatggcaga aagcgggtat gatattgcct tgttgaaact ggaaaccaca   1800
```

```
gtgaattaca cagattctca acgacccata tgcctgcctt ccaaaggaga tagaaatgta    1860
atatacactg attgctgggt gactggatgg gggtacagaa aactaagaga caaaatacaa    1920
aatactctcc agaaagccaa gatacccta gtgaccaacg aagagtgcca gaagagatac     1980
agaggacata aaataaccca taagatgatc tgtgccggct acagggaagg agggaaggac    2040
gcttgcaagg gagattcggg aggccctctg tcctgcaaac acaatgaggt ctggcatctg    2100
gtaggcatca cgagctgggg cgaaggctgt gctcaaaggg agcggccagg tgtttacacc    2160
aacgtggtcg agtacgtgga ctggattctg gagaaaactc aagcagtgtg aatgggttcc    2220 cagggggccat tggagtccct gaaggaccca ggatttgctg ggagagggtg ttgagttcac    2280
tgtgccagca tgcttcctcc acagtaacac gctgaagggg cttggtgttt gtaagaaaat    2340
gctagaagaa acaaaactgt cacaagttgt tatgtccaaa actcccgttc tatgatcgtt    2400
gtagtttgtt tgagcattca gtctctttgt ttttgatcac gcttctatgg agtccaagaa    2460
ttaccataag gcaatatttc tgaagattac tatataggca gatatagcag aaaataacca    2520
agtagtggca gtggggatca ggcagaagaa ctggtaaaag aagccaccat aaatagattt    2580
gttcgatgaa agatgaaaac tggaagaaag gagaacaaag acagtcttca ccattttgca    2640
ggaatctaca ctctgcctat gtgaacacat ttcttttgta aagaaagaaa ttgattgcat    2700
ttaatggcag attttcagaa tagtcaggaa ttcttgtcat ttccatttta aaatatatat    2760
taaaaaaaat cagttcgagt agacacgagc taagagtgaa tgtgaagata acagaatttc    2820
tgtgtggaag aggattacaa gcagcaattt acctggaagt gataccttag ggcaatcttt    2880
gaagatacac tttcctgaaa aatgatttgt gatggattgt atatttattt aaaatatctt    2940
gggaggggag gctgatggag ataggggagca tgctcaaacc tccctaagac aagctgctgc    3000
tgtgactatg ggctcccaaa gagctagatc gtatatttat ttgacaaaaa tcaccataga    3060
ctgcatccat actacagaga aaaacaatt agggcgcaaa tggatagtta cagtaaagtc    3120
ttcagcaagc agctgcctgt attctaagca ctgggatttt ctgtttcgtg caaatattta    3180
tctcattatt gttgtgatct agttcaataa cctagaattt gaattgtcac cacatagctt    3240
tcaatctgtg ccaacaacta tacaattcat caagtgtg                            3278

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Ala Ala Met Ser
1               5

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ile Ser Gly Ser Gly Ser Ser Thr Tyr Tyr Ala Asp Ser Val Lys
1               5                   10                  15
```

```
Gly

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Leu Ser Tyr Leu Tyr Ser Gly Tyr Tyr Phe Asp Tyr
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Phe Thr Phe Ser Thr Ala
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Gly Ser Gly Ser Ser
1               5

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Leu Ser Tyr Leu Tyr Ser Gly Tyr Tyr Phe Asp Tyr
1               5                   10

<210> SEQ ID NO 9
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Gly Ile Ser Gly Ser Gly Ser Ser Thr Tyr Tyr Ala Asp Ser Val
```

```
                    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Glu Leu Ser Tyr Leu Tyr Ser Gly Tyr Tyr Phe Asp Tyr Trp
                100                 105                 110

Gly Gln Gly Thr Leu Val Thr Val Ser Ser
            115                 120

<210> SEQ ID NO 10
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
caggtgcaat tgctggaaag cggcggtggc ctggtgcagc cgggtggcag cctgcgtctg        60
agctgcgcgg cgtccggatt cacctttttct actgctgcta tgtcttgggt gcgccaggcc      120
ccgggcaaag gtctcgagtg gtttccggt atctctggtt ctggttcttc tacctactat        180
gcggatagcg tgaaaggccg ctttaccatc agccgcgata ttcgaaaaaa caccctgtat       240
ctgcaaatga acagcctgcg tgcggaagat acggccgtgt attattgcgc gcgtgaactg      300
tcttacctgt actctggtta ctacttcgat tactggggcc aaggcaccct ggtgactgtt      360
agctca                                                                  366

<210> SEQ ID NO 11
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Thr Ala
             20                  25                  30

Ala Met Ser Trp Val Arg Gln Ala Pro Gly Lys Gly Leu Glu Trp Val
         35                  40                  45

Ser Gly Ile Ser Gly Ser Gly Ser Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Glu Leu Ser Tyr Leu Tyr Ser Gly Tyr Tyr Phe Asp Tyr Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160
```

Val Ser Trp Asn Ser Gly Ala Leu Thr Ser Gly Val His Thr Phe Pro
             165                 170                 175

Ala Val Leu Gln Ser Ser Gly Leu Tyr Ser Leu Ser Ser Val Val Thr
         180                 185                 190

Val Pro Ser Ser Ser Leu Gly Thr Gln Thr Tyr Ile Cys Asn Val Asn
         195                 200                 205

His Lys Pro Ser Asn Thr Lys Val Asp Lys Arg Val Glu Pro Lys Ser
     210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                 245                 250                 255

Met Ile Ser Arg Thr Pro Glu Val Thr Cys Val Val Val Asp Val Ser
             260                 265                 270

His Glu Asp Pro Glu Val Lys Phe Asn Trp Tyr Val Asp Gly Val Glu
         275                 280                 285

Val His Asn Ala Lys Thr Lys Pro Arg Glu Glu Gln Tyr Asn Ser Thr
     290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                 325                 330                 335

Ile Glu Lys Thr Ile Ser Lys Ala Lys Gly Gln Pro Arg Glu Pro Gln
             340                 345                 350

Val Tyr Thr Leu Pro Pro Ser Arg Glu Glu Met Thr Lys Asn Gln Val
         355                 360                 365

Ser Leu Thr Cys Leu Val Lys Gly Phe Tyr Pro Ser Asp Ile Ala Val
     370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                 405                 410                 415

Val Asp Lys Ser Arg Trp Gln Gln Gly Asn Val Phe Ser Cys Ser Val
             420                 425                 430

Met His Glu Ala Leu His Asn His Tyr Thr Gln Lys Ser Leu Ser Leu
         435                 440                 445

Ser Pro Gly Lys
    450

<210> SEQ ID NO 12
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
caggtgcaat tgctggaaag cggcggtggc ctggtgcagc cgggtggcag cctgcgtctg      60
agctgcgcgg cgtccggatt caccttttct actgctgcta tgtcttgggt gcgccaggcc     120
ccgggcaaag gtctcgagtg ggtttccggt atctctggtt ctggttcttc tacctactat     180
gcggatagcg tgaaaggccg ctttaccatc agccgcgata ttcgaaaaaa cacccctgtat    240 ctgcaaatga acagcctgcg tgcggaagat acggccgtgt attattgcgc gcgtgaactg     300

```
tcttacctgt actctggtta ctacttcgat tactggggcc aaggcaccct ggtgactgtt    360
agctcagcct ccaccaaggg tccatcggtc ttccccctgg caccctcctc caagagcacc    420
tctggggcca gcggcccct gggctgcctg gtcaaggact acttccccga accggtgacg     480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagagagtt    660
gagcccaaat cttgtgacaa aactcacaca tgcccaccgt gcccagcacc tgaagcagcg    720
gggggaccgt cagtcttcct cttcccccca aaacccaagg acaccctcat gatctcccgg    780
acccctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgggt ggtcagcgtc ctcaccgtcc tgcaccagga ctggctgaat    960
ggcaaggagt acaagtgcaa ggtctccaac aaagccctcc cagcccccat cgagaaaacc   1020
atctccaaag ccaaagggca gccccgagaa ccacaggtgt acaccctgcc cccatcccgg   1080
gaggagatga ccaagaacca ggtcagcctg acctgcctgg tcaaaggctt ctatcccagc   1140
gacatcgccg tggagtggga gagcaatggg cagccggaga caactacaa gaccacgcct    1200
cccgtgctgg actccgacgg ctccttcttc ctctacagca agctcaccgt ggacaagagc   1260
aggtggcagc aggggaacgt cttctcatgc tccgtgatgc atgaggctct gcacaaccac   1320
tacacgcaga agagcctctc cctgtctccg ggtaaa                              1356

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Gly Ser Ser Ser Asn Ile Gly Ser Asn Asp Val Ser
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Asn Tyr Asn Arg Pro Ser
1               5

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Ala Trp Asp Gln Arg Gln Phe Asp Val Val
1               5                   10
```

-continued

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Ser Ser Asn Ile Gly Ser Asn Asp
1               5

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Asn Tyr
1

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Trp Asp Gln Arg Gln Phe Asp Val
1               5

<210> SEQ ID NO 19
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
                20                  25                  30

Asp Val Ser Trp Tyr Gln Gln Leu Pro Gly Thr Ala Pro Lys Leu Leu
            35                  40                  45

Ile Tyr Lys Asn Tyr Asn Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu
            100                 105                 110

<210> SEQ ID NO 20
<211> LENGTH: 330
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 20

```
gatatcgtgc tgacccagcc gccgagcgtg agcggtgcac cgggccagcg cgtgaccatt      60
agctgtagcg gcagcagcag caacattggt tctaacgacg tgtcttggta ccagcagctg     120
ccgggcacgg cgccgaaact gctgatctac aaaaactaca accgcccgag cggcgtgccg     180
gatcgcttta gcggatccaa aagcggcacc agcgccagcc tggcgattac cggcctgcaa     240
gcagaagacg aagcggatta ttactgctct gcttgggacc agcgtcagtt cgacgttgtg     300
tttggcggcg gcacgaagtt aaccgtccta                                      330
```

<210> SEQ ID NO 21
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Asp Ile Val Leu Thr Gln Pro Pro Ser Val Ser Gly Ala Pro Gly Gln
 1               5                  10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 22
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
gatatcgtgc tgacccagcc gccgagcgtg agcggtgcac cgggccagcg cgtgaccatt      60
agctgtagcg gcagcagcag caacattggt tctaacgacg tgtcttggta ccagcagctg     120
ccgggcacgg cgccgaaact gctgatctac aaaaactaca accgcccgag cggcgtgccg     180
gatcgcttta gcggatccaa aagcggcacc agcgccagcc tggcgattac cggcctgcaa     240
gcagaagacg aagcggatta ttactgctct gcttgggacc agcgtcagtt cgacgttgtg     300
tttggcggcg gcacgaagtt aaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca caagtacgcg gccagcagc      540 tatctgagcc tgacgcctga gcagtggaag tcccacagaa gctacagctg ccaggtcacg     600
catgaaggga gcaccgtgga aagacagtg gcccctacag aatgttca                   648
```

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Ala Ala Met Ser
1               5

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Ile Ser Gly Ser Gly Ser Ser Thr Tyr Tyr Ala Asp Ser Val Lys
1               5                   10                  15

Gly

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Leu Ser Tyr Leu Tyr Ser Gly Tyr Tyr Phe Asp Tyr
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Phe Thr Phe Ser Thr Ala
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Gly Ser Gly Ser Ser
1               5

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Leu Ser Tyr Leu Tyr Ser Gly Tyr Tyr Phe Asp Tyr
1               5                   10

<210> SEQ ID NO 29
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Gly Ile Ser Gly Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser
            115                 120

<210> SEQ ID NO 30
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
caggtgcagc tgctggaatc aggcggcgga ctggtgcagc ctggcggtag cctgagactg    60

-continued

```
agctgcgctg ctagtggctt cacctttagc accgccgcta tgagctgggt tcgacaggcc      120
ccagggaaag gcctcgagtg ggtctcaggg attagcggta gcggctctag cacctactac      180
gccgatagcg tgaagggccg gttcactatc tctagggata actctaagaa caccctgtac      240
ctgcagatga atagcctgag agccgaggac accgccgtct actactgcgc tagagagctg      300
agctacctgt atagcggcta ctacttcgac tactggggtc aaggcaccct ggtcaccgtg      360
tctagc                                                                  366
```

<210> SEQ ID NO 31
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Gly Ile Ser Gly Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ala Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300
```

```
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Ala Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 32
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
caggtgcagc tgctggaatc aggcggcgga ctggtgcagc ctggcggtag cctgagactg      60
agctgcgctg ctagtggctt cacctttagc accgccgcta tgagctgggt tcgacaggcc    120
ccagggaaag gcctcgagtg gtctcaggg attagcggta gcggctctag cacctactac     180
gccgatagcg tgaagggccg gttcactatc tctaggata actctaagaa cacccctgtac    240 ctgcagatga atagcctgag agccgaggac accgccgtct actactgcgc tagagagctg    300
agctacctgt atagcggcta ctacttcgac tactggggtc aaggcaccct ggtcaccgtg    360
tctagcgcta gcactaaggg ccctccgtg ttccctctgg cccttccag caagtctacc      420 tccggcggca cagctgctct gggctgcctg gtcaaggact acttccctga gcctgtgaca    480
gtgtcctgga actctggcgc cctgacctct ggcgtgcaca ccttccctgc cgtgctgcag    540
tcctccggcc tgtactccct gtcctccgtg gtcacagtgc cttcaagcag cctgggcacc    600
cagacctata tctgcaacgt gaaccacaag ccttccaaca ccaaggtgga caagcgggtg    660
gagcctaagt cctgcgacaa gacccacacc tgtcctcccct gccctgctcc tgaactgctg    720
ggcggccctt ctgtgttcct gttccctcca aagcccaagg acaccctgat gatctcccgg    780 accccctgaag tgacctgcgt ggtggtggcc gtgtcccacg aggatcctga agtgaagttc    840
aattggtacg tggacggcgt ggaggtgcac aacgccaaga ccaagcctcg ggaggaacag    900
tacaactcca cctaccgggt ggtgtccgtg ctgaccgtgc tgcaccagga ctggctgaac    960
ggcaaagagt acaagtgcaa agtctccaac aaggccctgg ccgcccctat cgaaaagaca   1020
atctccaagg ccaagggcca gcctagggaa ccccaggtgt acaccctgcc acccagccgg   1080
gaggaaatga ccaagaacca ggtgtccctg acctgtctgg tcaagggctt ctacccttcc   1140
```

```
gatatcgccg tggagtggga gtctaacggc cagcctgaga caaactacaa gaccacccct    1200
cctgtgctgg actccgacgg ctccttcttc ctgtactcca aactgaccgt ggacaagtcc    1260
cggtggcagc agggcaacgt gttctcctgc tccgtgatgc acgaggccct gcacaaccac    1320
tacacccaga agtccctgtc cctgtctccc ggcaag                              1356
```

```
<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Gly Ser Ser Ser Asn Ile Gly Ser Asn Asp Val Ser
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Asn Tyr Asn Arg Pro Ser
1               5

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Ala Trp Asp Gln Arg Gln Phe Asp Val Val
1               5                   10

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Ser Ser Asn Ile Gly Ser Asn Asp
1               5

<210> SEQ ID NO 37
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Asn Tyr
1
```

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Trp Asp Gln Arg Gln Phe Asp Val
1               5

<210> SEQ ID NO 39
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu
            100                 105                 110

<210> SEQ ID NO 40
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
cagtcagtcc tgactcagcc ccctagcgct agtggcaccc ctggtcaaag agtgactatt      60
agctgtagcg gctctagctc taatatcggc tctaacgacg tcagctggta tcagcagctg     120
cccggcaccg cccctaagct gctgatctat aagaactata ataggcctag cggcgtgccc     180
gataggttta gcggatctaa atcagggact tctgctagtc tggctattag cggcctgcag     240
tcagaggacg aggccgacta ctactgtagc gcctgggatc agcgtcagtt cgacgtggtg     300
ttcggcggag gcactaagct gaccgtgctg                                      330

<210> SEQ ID NO 41
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 42
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
cagtcagtcc tgactcagcc ccctagcgct agtggcaccc ctggtcaaag agtgactatt      60
agctgtagcg gctctagctc taatatcggc tctaacgacg tcagctggta tcagcagctg     120
cccggcaccg cccctaagct gctgatctat aagaactata ataggcctag cggcgtgccc     180
gataggttta gcggatctaa atcagggact tctgctagtc tggctattag cggcctgcag     240
tcagaggacg aggccgacta ctactgtagc gcctgggatc agcgtcagtt cgacgtggtg     300
ttcggcggag cactaagct gaccgtgctg ggtcaaccta aggctgcccc cagcgtgacc      360
ctgttccccc ccagcagcga ggagctgcag gccaacaagg ccaccctggt gtgcctgatc     420
agcgacttct acccaggcgc cgtgaccgtg gcctggaagg ccgacagcag ccccgtgaag     480
gccggcgtgg agaccaccac ccccagcaag cagagcaaca acaagtacgc cgccagcagc     540
tacctgagcc tgacccccga gcagtggaag agccacaggt cctacagctg ccaggtgacc     600
cacgagggca gcaccgtgga aaagaccgtg gccccaaccg agtgcagc                  648

<210> SEQ ID NO 43
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Phe Thr Phe Ser Thr Ala Ala
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Ser Gly Ser Gly Ser Ser Thr
1               5

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Arg Glu Leu Ser Tyr Leu Tyr Ser Gly Tyr Tyr Phe Asp Tyr
1               5                   10                  15

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Phe Thr Phe Ser Thr Ala Ala Met Ser
1               5                   10

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Ser Asn Ile Gly Ser Asn Asp
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 48

His His His His His His
```

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Met Gly Ser Ser
1

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 50

His His His His His His His His
1               5

<210> SEQ ID NO 51
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Ile Val Gly Gly Thr Ala Ser Val Arg Gly Glu Trp Pro Trp Gln Val
1               5                   10                  15

Thr Leu His Thr Thr Ser Pro Thr Gln Arg His Leu Cys Gly Gly Ser
            20                  25                  30

Ile Ile Gly Asn Gln Trp Ile Leu Thr Ala Ala His Cys Phe Tyr Gly
        35                  40                  45

Val Glu Ser Pro Lys Ile Leu Arg Val Tyr Ser Gly Ile Leu Asn Gln
    50                  55                  60

Ser Glu Ile Lys Glu Asp Thr Ser Phe Phe Gly Val Gln Glu Ile Ile
65                  70                  75                  80

Ile His Asp Gln Tyr Lys Met Ala Glu Ser Gly Tyr Asp Ile Ala Leu
                85                  90                  95

Leu Lys Leu Glu Thr Thr Val Asn Tyr Thr Asp Ser Gln Arg Pro Ile
            100                 105                 110

Cys Leu Pro Ser Lys Gly Asp Arg Asn Val Ile Tyr Thr Asp Cys Trp
        115                 120                 125

Val Thr Gly Trp Gly Tyr Arg Lys Leu Arg Asp Lys Ile Gln Asn Thr
    130                 135                 140

Leu Gln Lys Ala Lys Ile Pro Leu Val Thr Asn Glu Glu Cys Gln Lys
145                 150                 155                 160

Arg Tyr Arg Gly His Lys Ile Thr His Lys Met Ile Cys Ala Gly Tyr
                165                 170                 175

Arg Glu Gly Gly Lys Asp Ala Cys Lys Gly Asp Ser Gly Gly Pro Leu
            180                 185                 190

Ser Cys Lys His Asn Glu Val Trp His Leu Val Gly Ile Thr Ser Trp
        195                 200                 205

```
Gly Glu Gly Cys Ala Gln Arg Glu Arg Pro Gly Val Tyr Thr Asn Val
    210                 215                 220

Val Glu Tyr Val Asp Trp Ile Leu Glu Lys Thr Gln Ala Val
225                 230                 235
```

FACTOR XI ANTIBODIES AND METHODS OF USE

This application claims the benefit of U.S. Provisional Application No. 62/184,955 filed on Jun. 26, 2015 and U.S. Provisional Application No. 62/341,568 filed on May 25, 2016, each of which is hereby incorporated by reference in its entirety.

The instant application contains a Sequence Listing which has been submitted electronically in ASCII format and is hereby incorporated by reference in its entirety. Said ASCII copy, created on Jun. 23, 2016, is named "PAT056955-US-NP_SL.txt" and is 44,601 bytes in size.

BACKGROUND

Thrombosis refers to thrombus formation inside blood vessels, subsequent to a combination of hereditary and acquired risk factors, known as thrombophilia or hypercoagulable states. Vessel wall damage, stasis, increased platelets reactivity and activation of clotting factors are some of the fundamental features of thrombosis. Thrombosis can occur in both venous and arterial circulation and can result in the development of deep vein thrombosis (DVT), pulmonary embolism, and stroke. If a thrombus occurs in the arterial system, down-stream ischemia can occur, leading to acute coronary syndromes (ACS), ischemic stroke, and acute limb ischemia. Thrombus formation in the venous system typically leads to deep venous thrombosis, pulmonary embolism and chronic thromboembolic pulmonary hypertension. Clots may also form in the left atrial appendage in patients with atrial fibrillation (AF), and dislodged thrombi may result in potentially devastating complications, i.e. thromboembolic stroke and systemic embolism. The currently available antithrombotic medications, including low molecular weight heparin (LMWH), thrombin inhibitors, and Factor Xa (FXa) inhibitors, are all associated with a significant risk of bleeding (Weitz J. I. (2010) Thromb. Haemost. 103, 62). The development of an antithrombotic agent that does not affect hemostasis, and therefore does not result in bleeding complications, would be highly desirable.

Current anticoagulants are either injected or taken orally. The injectable anticoagulant LMWH is widely used and offers an improved therapeutic profile over formerly applied unfractionated heparin. For the past few decades the most commonly used oral anticoagulant has been warfarin. Warfarin has a narrow therapeutic window that requires frequent monitoring of the coagulation status, and shows a variety of drug-drug interactions. More recently, orally available direct FXa and thrombin inhibitors entered the anticoagulant market and are increasingly applied.

LMWHs, FXa inhibitors, and thrombin inhibitors are all efficacious in the prevention of post-operative venous thromboembolic disease, in the treatment of spontaneous DVT and pulmonary embolism, and in the stroke prevention in atrial fibrillation. However, these anticoagulants are also associated with bleeding complications that were generally comparable to those observed with the older drugs warfarin and unfractionated heparin. In the ADVANCE-2 clinical trial, the FXa inhibitor apixaban (Eliquis) was compared to the LMWH enoxaparin in patients after total knee replacement. While acute apixaban therapy was more effective at preventing venous thromboembolic disease than enoxaparin, both agents were associated with a significant risk of bleeding. Clinically relevant bleeding occurred in 4% of patients receiving apixaban and in 5% of patients treated with enoxaparin (Lassen, M. R., et al. (2009) N. Engl. J. Med. 361, 594).

In the RE-LY trial, the direct thrombin inhibitor dabigatran (Pradaxa) was compared to warfarin in patients with atrial fibrillation and a risk of stroke (Connolly, S. J., et al. (2009) N. Engl. J. Med. 361, 1139). Chronic dabigatran therapy was associated with a significantly lower risk of stroke or systemic embolism. However, major bleeding complications occurred in 3.1% of patients receiving 150 mg per day of dabigatran and in 3.4% of patients receiving warfarin (p=0.31).

Atrial fibrillation (AF) remains the most common cardiac arrhythmia in clinical practice, accounting for approximately one third of hospitalizations for cardiac dysrhythmias. Currently, it is estimated to affect more than 6 million patients in Europe and approximately 2.3 million in the United States, and this number continues to grow rapidly because of the increasing proportion of the aging population. It is estimated that approximately 5% of the population over the age of 65 years, and 10% of people aged over 80 years, will develop AF, however, the prevalence of AF is increasing beyond what is explained by age alone. AF risk factors such as hypertension, congestive heart failure, left ventricular hypertrophy, coronary artery disease and diabetes mellitus, and obstructive sleep apnea are also on the rise. As such, the number of affected individuals with AF is expected to increase two to three times over the next three decades in western populations. (Kannel and Benjamin (2008) Med Clin North Am. 2008; 92:17-40; Bunch, et al. (2012) J Innovations of Card Rhythm Manag 2012; 3: 855-63).

The principal risk of AF is a four- to five fold increase in embolic stroke. The attributable risk for stroke associated with AF increases steeply with age to 23.5% at ages 80 to 89. AF is associated with a doubling of mortality in both genders (Kannel and Benjamin 2008). AF is also independently associated with cognitive decline and all forms of dementia (Marzona, et al. (2012) CMAJ 2012; 184: 329-36; Geita et al 2013; Bunch et al 2012).

Most patients with AF require life-long anticoagulation therapy to prevent cardioembolic stroke and systemic embolism. The CHA2DS2-VASc risk score is a validated and widely used stratification tool to predict thromboembolic risk in atrial fibrillation patients and to identify patients who should benefit from anticoagulation therapy (LIP 2011; Camm, et al. (2012) Eur Heart J 2012; 33: 2719-2747); the accumulated evidence shows that CHA2DS2-VASc is at least as accurate as or possibly better than, scores such as CHADS2 in identifying patients who develop stroke and thromboembolism and definitively better at identifying 'truly low-risk' patients with AF. It is estimated that 85 to 90% of AF patients will require anticoagulation therapy.

In a meta-analysis comprising 6 trials which evaluated the effect of vitamin K antagonists (VKA) in reducing stroke and systemic embolism, a highly significant risk reduction in stroke incidence (relative risk reduction of 67% for stoke) was observed. All-cause mortality was significantly reduced (26%) by adjusted-dose VKA vs. control (Hart, Pearce, and Aguilar (2007) Ann Intern Med 2007; 146:857-867). An international normalized ratio (INR) target between 2 and 3 was associated with best benefit-risk ratio (Hylek et al (2003) N Engl J Med; 349:1019-1026) and universally adopted by international and national guidelines.

In the recent years new oral anticoagulants (NOAC) also referred to as direct oral anticoagulants (DOAC) have been approved and introduced to clinical practice. These drugs are at least as effective or even better than warfarin for reducing thrombo-embolic disease (Connolly, et al. (2009) N Engl J Med; 361:1139-51; Connolly, et al. (2011) N Engl J Med; 364:806-17; Patel, et al. (2011) N Engl J Med 2011; 365: 883-91). NOAC were also associated with large reductions in the most devastating complications of warfarin namely hemorrhagic stroke and intracranial hemorrhage. Major bleeding events were similar or slightly lower than well conducted warfarin therapy. In addition NOAC are associated with a lower potential for drug-drug interaction than warfarin and could be used without routine monitoring; this is expected to ease their use in everyday medical practice.

Despite recent improvements, bleeding risk continues to be high with the use of anticoagulants. For instance, the annual incidence of major and clinically relevant non major bleeding was 14.9% and the annual incidence of major bleeding events was 3.6% in patients treated with rivaroxaban in the ROCKET study (Patel et al 2011). The annual incidence of major bleeding was >5% in patients at a high risk for bleeding defined as HAS Bled risk score ≥3 (Gallego, et al. (2012) Carc Arrhythm Electrophysiol.; 5:312-318). Major bleeding is a particularly relevant clinical outcome; for instance in the ROCKET study, once major bleeding has occurred, all-cause mortality rate was 20.4% in the rivaroxaban group and 26.1% in the warfarin group. Once major bleeding events have occurred stroke and systemic embolism occurred in 4.7% and 5.4% of patients in rivaroxaban and warfarin groups, respectively (Piccini, et al. (2014) Eur Heart J; 35:1873-80). Hospital stay, transfusion of blood products and resources utilization were also severely impacted by the occurrence of major bleeding. Bleeding risk is also a major reason for not receiving anticoagulants in eligible patients. In the Euro Heart Survey on Atrial Fibrillation comprising data from 182 hospitals in 35 countries and 5333 ambulant and hospitalized AF patients, only 67% of eligible patients received oral anticoagulant at discharge (Nieuwlaat, et al (2005) Eur Heart J; 26, 2422-2434).

A high unmet medical need therefore exists for a safer therapy which can reduce AF thromboembolic complications such as stroke, systemic embolism, cognitive decline and mortality with comparable efficacy as existing therapy but with a lower bleeding liability.

SUMMARY

The present invention relates to monoclonal antibodies binding to human coagulation Factor XI and XIa (activated Factor XI) (hereinafter, sometimes referred to as "FXI", "FXIa," and similar terms), and pharmaceutical compositions comprising the same and methods of treatment comprising administering the same. The development of an anti-thrombotic agent that is efficacious in the prevention and treatment of thrombosis or thromboembolic disease/disorder (e.g., thrombic stroke, atrial fibrillation, stroke prevention in atrial fibrillation (SPAF), deep vein thrombosis, venous thromboembolism, pulmonary embolism, acute coronary syndromes (ACS), ischemic stroke, acute limb ischemia, chronic thromboembolic pulmonary hypertension, systemic embolism) but carries no or only minimal bleeding risk would meet a sizable unmet medical need.

In specific aspects, antibodies (e.g., human, chimeric, humanized monoclonal antibodies) provided herein bind with similarly high affinity to the catalytic domain (CD) of human FXIa and FXI and induces an inactive protease domain conformation in FXIa.

The isolated anti-FXI and/or anti-FXIa antibodies described herein, e.g., the full IgGs described herein with two binding sites, bind FXI and/or FXIa with an equilibrium dissociation constant ($K_D$) of less than or equal to 100 pM. For example, the isolated antibodies described herein may bind to human FXI and/or FXIa with a $K_D$ of less than or equal to 100 pM, less than or equal to 50 pM, less than or equal to 45 pM, less than or equal to 40 pM, less than or equal to 35 pM, less than or equal to 20 pM, or less than or equal to 10 pM. More specifically, the isolated antibodies described herein may also bind human FXI and/or FXIa with a $K_D$ of less than or equal to 34 pM, as measured by surface plasmon resonance (SPR), e.g., BIACORE™ assay, or less than or equal to 4 pM, as measured by solution equilibrium titration assay (SET); and may also bind cynomolgus monkey FXI and/or FXIa with a $K_D$ of less than or equal to 53 pM, as measured by BIACORE™ assay, or less than or equal to 4 pM, as measured by SET. In specific aspects, isolated antibodies described herein (e.g., NOV1401) bind human FXI and FXIa with an apparent $K_D$ of less than or equal to approximately 5 pM (e.g., 4.7 pM) and 2 pM (e.g., 1.3 pM), respectively, for example as measured by solution equilibrium titration assay (SET). In specific embodiments, anti-FXI/FXIa antibodies described herein bind to cynomolgus monkey FXI/FXIa with an apparent $K_D$ of approximately 12.5 (±6.6) pM for FXIa and approximately 5.0 (±0.7) pM as measured by SET (see, e.g., Example 2). In specific embodiments, anti-FXI/FXIa antibodies described herein bind rabbit FXI and/or FXIa with a $K_D$ of approximately 20 (±2) nM. In specific aspects, anti-FXI/FXIa antibodies described herein bind human, cynomolgus monkey and rabbit FXI and/or FXIa, but do not specifically bind mouse or rat FXI.

The isolated anti-FXI and/or anti-FXIa antigen binding fragments described herein, e.g., Fab fragments and other fragments containing one binding site, bind FXI and/or FXIa, with an equilibrium dissociation constant ($K_D$) of less than or equal to 10 nM. For example, the isolated antigen binding fragments described herein may bind to human FXI and/or FXIa with a KD of less than or equal to 10 nM, less than or equal to 5 nM, less than or equal to 1 nM, less than or equal to 500 pM, less than or equal to 305 pM, less or equal to 62 pM. More specifically, the isolated antigen binding fragments described herein may also bind human FXI and/or FXIa with a KD of less than or equal to 305 pM.

The present invention relates to an isolated antibody, or antigen binding fragments thereof, that binds to human, rabbit, and cynomolgus monkey FXIa. The invention also relates to an isolated antibody, or antigen binding fragments thereof, that binds within the catalytic domain of FXI and/or FXIa, specifically to the surface of the active site region.

The present invention also relates to an isolated antibody, or antigen binding fragments thereof, that binds FXI and/or FXIa and further competes for binding with an antibody as described in Table 1 (e.g., NOV1401). As described here, "competition" between antibodies and/or antigen binding fragments thereof signifies that both antibodies (or binding fragments thereof) bind to the same, or overlapping, FXI and/or FXIa epitope (e.g., as determined by a competitive binding assay, by any of the methods well known to those of skill in the art). As used herein, an antibody or antigen binding fragment thereof does not "compete" with an FXI and/or FXIa antibody or antigen binding fragment of the invention (e.g., NOV1401 or NOV1090) unless said competing antibody or antigen binding fragment thereof binds the same FXI and/or FXIa epitope, or an overlapping FXI and/or FXIa epitope, as an antibody or antigen binding fragment of the invention. As used herein, a competing antibody or antigen binding fragment thereof does not include one which (i) sterically blocks an antibody or antigen binding fragment of the invention from binding its target (e.g., if said competing antibody binds to a nearby, non-overlapping FXI and/or FXIa epitope and physically prevents an antibody or antigen binding fragment of the invention from binding its target); and/or (ii) binds to a different, non-overlapping FXI and/or FXIa epitope and induces a conformational change to the FXI and/or FXIa protein such that said protein can no longer be bound by an FXI and/or FXIa antibody or antigen binding fragment of the invention in a way that would occur absent said conformational change.

In one embodiment, isolated antibodies, or antigen binding fragments thereof, bind FXI and/or FXIa and further compete for binding with an antibody as described in Table 1 bind to a majority of the amino acids of the epitope(s) bound by said antibody of Table 1. In another embodiment, isolated antibodies, or antigen binding fragments thereof, that bind FXI and/or FXIa and further compete for binding with an antibody as described in Table 1 bind to all of the epitope(s) bound by said antibody of Table 1.

In one embodiment, isolated antibodies, or antigen binding fragments thereof, bind to active FXI (FXIa) and leads upon binding to the active FXI (FXIa) catalytic domain to FXIa changing its conformation to an inactive conformation. In another embodiment, said isolated antibodies or antigen binding fragments thereof further induce a change in which the N-terminal 4 residues, loops 145, 188 and 220 of said inactive conformation are shifted and/or disordered compared to the active conformation.

In one embodiment, isolated antibodies, or antigen binding fragments thereof, bind to FXI (e.g., human FXI) and upon binding to FXI prevent the FXI catalytic domain from assuming an active conformation, in which loops 145, 188 and 220 are ordered as in the structure of the FXIa catalytic domain.

In one embodiment, isolated antibodies, or antigen binding fragments thereof, bind to FXI and upon binding to FXI prevents the FXI catalytic domain from assuming an active conformation, in which the N-terminal 4 residues, loops 145, 188 and 220 are ordered as in the structure of the FXIa catalytic domain.

In one embodiment, isolated antibodies, or antigen binding fragments thereof, bind to FXI and upon binding to FXI prevents the FXI catalytic domain from assuming an active conformation by inducing conformational changes in the zymogen structure, further leading to an inhibited FXI conformation closely related to that observed when binding to FXIa.

In one embodiment, isolated antibodies, or antigen binding fragments thereof, bind to FXI and/or FXIa and upon binding to FXI and/or FXIa and forming an antibody:antigen complex with the catalytic domain of FXI and/or FXIa cause a shift and/or disorientation of loops 145, 188 and 220 when compared with the uncomplexed structure of the catalytic domain of active Factor XI (FXIa).

In one embodiment, isolated antibodies, or antigen binding fragments thereof, bind to FXI and/or FXIa upon binding to FXI and/or FXIa and forming an antibody:antigen complex with the catalytic domain of FXI and/or FXIa causes a shift and/or disorientation of the N-terminal 4 residues, loops 145, 188 and 220 when compared with the uncomplexed structure of the catalytic domain of active Factor XI (FXIa).

In one embodiment, isolated antibodies, or antigen binding fragments thereof, bind to active FXI (FXIa) and cause the FXI (FXIa) catalytic domain to change its conformation to an inactive conformation, in which loops 145, 188 and 220 are shifted and/or disoriented compared to the active conformation.

In one embodiment, isolated antibodies, or antigen binding fragments thereof, bind to FXI and prevent the catalytic domain from assuming an active conformation by inducing a conformational changes in the zymogen structure, thereby leading to an inhibited FXI conformation closely related to that observed when binding to FXIa.

The present invention also further relates to an isolated antibody, or antigen binding fragments thereof, that binds the same epitope as an antibody as described in Table 1 (e.g., NOV1401).

The binding affinity of isolated antibodies and antigen binding fragments described herein can be determined by solution equilibrium titration (SET). Methods for SET are known in the art and are described in further detail below. Alternatively, binding affinity of the isolated antibodies, or fragments, described herein can be determined by surface plasmon resonance measurements, e.g., in BIACORE™ assays. Methods for BIACORE™ kinetic assays are known in the art and are described in further detail below.

The isolated anti-FXI and/or FXIa antibodies and antigen binding fragments described herein can be used to inhibit the direct or indirect activation of Factor IX (also known as FIX), Factor X (FX), and/or thrombin, and/or the binding to platelet receptors, and thereby can prevent activation of the intrinsic and/or common coagulation pathways.

The isolated anti-FXI and/or FXIa antibodies and antigen binding fragments described herein can be used to inhibit the direct or indirect activation of Factor IX (also known as FIX), Factor X (FX), and/or thrombin with an $IC_{50}$ of less than or equal to 100 nM, less than or equal to 50 nM, less than or equal to 35 nM, less than or equal to 25 nM, less than or equal to 10 nM, or less than or equal to 5.2 nM. More specifically, an isolated antibody or antigen binding fragments thereof as described herein can inhibit the direct or indirect activation of Factor IX (also known as FIX), Factor X (FX), and/or thrombin with an $IC_{50}$ of less than or equal to 100 nM, less than or equal to 50 nM, less than or equal to 35 nM, less than or equal to 25 nM, less than or equal to 10 nM, or less than or equal to 5.2 nM. More specifically, an isolated antibody or antigen binding fragments thereof as described herein can inhibit the direct or indirect activation of Factor IX (also known as FIX), Factor X (FX), and/or thrombin with an $IC_{50}$ of less than or equal to 100 nM, less than or equal to 50 nM, less than or equal to 35 nM, less than or equal to 25 nM, less than or equal to 20 nM, or less than or equal to 18 nM. More specifically, an isolated antibody or antigen binding fragments thereof as described herein can inhibit the direct or indirect activation of Factor IX (also known as FIX), Factor X (FX), and/or thrombin with an $IC_{50}$ of less than or equal to 100 nM, less than or equal to 50 nM, less than or equal to 35 nM, less than or equal to 25 nM, less than or equal to 10 nM, or less than or equal to 5 nM. In a specific embodiment, an anti-FXI/FXIa antibody described herein, or antigen binding fragment thereof, inhibits FXIa-mediated activation of its native substrate FIX with an $IC_{50}$ of less than or equal to 2 nM, e.g., 1.8 nM.

The isolated anti-FXI and/or anti-FXIa antibodies, or antigen binding fragments thereof, may be used to inhibit (e.g., block the activation of) the intrinsic and/or common coagulation pathways, e.g., via inhibiting FXI and/or FXIa-mediated activation of FIX. The isolated anti-FXI/FXIa antibodies, or antigen binding fragments thereof, may therefore be used to prevent clotting or the propagation of clotting. The isolated antibodies, or antigen binding fragments thereof, may be used to prevent, treat, or ameliorate such coagulation disorders as deep vein thrombosis and stroke (e.g., ischemic stroke) by inhibiting FXI-mediated activation of FIX.

In specific embodiments, anti-FXI and/or anti-FXIa antibodies, or antigen binding fragments thereof, are capable of prolonging the clotting time (e.g., time until a blood clot starts to form) of human plasma in a concentration-dependent manner as determined by an aPTT assay, for example as described in the Examples Section. In a specific embodiment, clotting time (aPTT) was doubled compared to baseline at a total anti-FXI antibody (e.g., NOV1401) concentration in the range of 10 nM to 20 nM, for example approximately 14 nM or 15 nM, as determined by an aPTT assay. In particular embodiments, anti-FXI and/or anti-FXIa antibodies, or antigen binding fragments thereof, are capable of prolonging the clotting time of human plasma in a concentration-dependent manner with an 1050 in the range of 5 nM to 20 nM, for example approximately 13 nM, as determined by the aPTT assay, for example as described in the Examples Section.

In specific embodiments, anti-FXI and/or anti-FXIa antibodies described herein, or antigen binding fragments thereof, are capable of prolonging the clotting time (e.g., time until a blood clot starts to form) of human plasma by at least 1.1 fold, 1.2 fold, 1.3 fold, 1.4 fold, 1.5 fold, 1.6 fold, 1.7 fold, 1.8 fold, 1.9 fold, or 2 fold, e.g., in a concentration-dependent manner, as determined by an aPTT assay, for example as described in the Examples Section. In specific embodiments, anti-FXI and/or anti-FXIa antibodies described herein, or antigen binding fragments thereof, are capable of prolonging the clotting time (e.g., time until a blood clot starts to form) of human plasma by at least 1.4 fold, 1.5 fold, 1.6 fold, or 1.7 fold, as determined by an aPTT assay, for example as described in the Examples Section.

In specific aspects, anti-FXI and/or anti-FXIa antibodies, or antigen binding fragments thereof, described herein is capable of reducing the amount of thrombin, in a concentration-dependent manner, in a thrombin generation assay (TGA) in human plasma, which measures the effect of FXIa inhibition on the thrombin→FXIa feed-forward loop in the presence of very low tissue factor (TF) concentrations. In particular embodiments, anti-FXI and/or anti-FXIa antibodies, or antigen binding fragments thereof, described herein is capable of reducing the amount of thrombin in a thrombin generation assay (TGA) in human plasma with an $IC_{50}$ value in the range of 10 nM to 30 nM, for example approximately 20 nM or 24 nM, and a residual thrombin concentration of approximately 159 nM.

In specific aspects, provided herein are antibodies (e.g., antibodies in Table 1 such as NOV1401 or antibodies comprising the HCDRs 1-3 and LCDRs 1-3 of NOV1401), or antigen binding fragments thereof, which specifically binds to the catalytic domain of human FXI and/or FXIa, and which has a terminal elimination half-life ($t_{1/2}$) of total antibodies in cynomolgus monkeys as approximately 14-15 days. In specific embodiments, such anti-FXI/FXIa antibodies exhibit an absolute subcutaneous (s.c.) bioavailability of approximately 61-66%.

In a specific embodiment, an antibody or antigen binding fragment thereof provided herein (e.g., antibody described in Table 1, such as NOV1401), which specifically binds to human FXI and/or FXIa, exhibits one or more (e.g., two, or three, or four, or five, or six, or seven), or all, of the following characteristics:

(i) specifically binds to a catalytic domain (CD) of human FXI and FXIa, for example, with an apparent $K_D$ of approximately 1-2 pM and 4-5 pM respectively;
(ii) prolongs clotting time as evaluated by activated partial thromboplastin time (aPTT) assay;
(iii) inhibits thrombin generation in human plasma through inhibition of FXI activation by activated factor XII (FXIIa) and by thrombin, respectively;
(iv) shows antithrombotic and anticoagulant activity in FXI−/− mice reconstituted with human FXI;
(v) reduces or prolongs the reduction of free FXI ($FXI_f$) levels, for example, in cynomolgus monkeys;
(vi) has a terminal elimination half-life of total antibody of approximately 14-15 days, for example, in cynomolgus monkeys;
(vii) specifically binds to human and monkey FXI and/or FXIa but does not specifically bind to mouse or rat FXI and/or FXIa; and
(viii) contacts one or more (e.g., two, three, four, five, six, or seven, or more), or some, or all, of the following residues of human FXI (Swissprot numbering): Pro410, Arg413, Leu415, Cys416, His431, Cys432, Tyr434, Gly435, Glu437, Tyr472-Glu476, Tyr521-Lys527, Arg548, His552, Ser575, Ser594-Glu597, and Arg602-Arg604.

The isolated anti-FXI and/or FXIa antibodies, or antigen binding fragments thereof, as described herein can be monoclonal antibodies, human or humanized antibodies, chimeric antibodies, single chain antibodies, Fab fragments, Fv fragments, F(ab')2 fragments, or scFv fragments, and/or IgG isotypes (e.g., IgG1 such as human IgG1). In specific embodiments, anti-FXI and/or anti-FXIa antibodies described herein are recombinant human antibodies. In specific embodiments, anti-FXI and/or anti-FXIa antibodies described herein are human IgG1/lambda (λ) antibodies. In specific embodiments, anti-FXI and/or anti-FXIa antibodies described herein are human IgG1/lambda (λ) antibodies comprising an Fc domain engineered to reduce the potential for effector function (e.g., ADCC and/or CDC), for example a human Fc domain comprising D265A and/or P329A substitutions.

The isolated anti-FXI and/or FXIa antibodies, or antigen binding fragments thereof, as described herein can also include a framework in which an amino acid has been substituted into the antibody framework from the respective human VH or VL germline sequences.

Another aspect of the invention includes an isolated antibody or antigen binding fragments thereof having the full heavy and light chain sequences of Fabs described in Table 1. More specifically, the isolated antibody or antigen binding fragments thereof can have the heavy and light chain sequences of NOV1090 and NOV1401.

A further aspect of the invention includes an isolated antibody or antigen binding fragments thereof having the heavy and light chain variable domain sequences of Fabs described in Table 1. More specifically, the isolated antibody or antigen binding fragment thereof can have the heavy and light chain variable domain sequence of NOV1090 and NOV1401.

A further aspect of the invention includes an isolated antibody or antigen binding fragments thereof having the heavy chain variable domain CDR (i.e., HCDR1, HCDR2, and HCDR3) and light chain variable domain CDR (i.e., LCDR1, LCDR2, and LCDR3) sequences of antibodies described in Table 1, such as Kabat CDRs, IMGT CDRs, Chothia CDRs, or combined CDRs. More specifically, the isolated antibody or antigen binding fragment thereof can have the HCDR1, HCDR2, HCDR3, LCDR1, LCDR2, and LCDR3 sequences of NOV1090 and NOV1401, for example as presented in Table 1, such as Kabat CDRs, IMGT CDRs, Chothia CDRs, or combined CDRs.

The invention also relates to an isolated antibody or antigen binding fragments thereof that includes a heavy chain CDR1 selected from the group consisting of SEQ ID NOs: 3 and 23; a heavy chain CDR2 selected from the group consisting of SEQ ID NOs: 4 and 24; and a heavy chain CDR3 selected from the group consisting of SEQ ID NOs: 5 and 25, wherein the isolated antibody or antigen binding fragments thereof binds to human FXI and/or FXIa. In another aspect, such isolated antibody or antigen binding fragments thereof further includes a light chain CDR1 selected from the group consisting of SEQ ID NOs: 13 and 33; a light chain CDR2 selected from the group consisting of SEQ ID NOs: 14 and 34; and a light chain CDR3 selected from the group consisting of SEQ ID NOs: 15 and 35.

The invention also relates to an isolated antibody or antigen binding fragments thereof that includes a light chain CDR1 selected from the group consisting of SEQ ID NOs: 13 and 33; a light chain CDR2 selected from the group consisting of SEQ ID NOs: 14 and 34; and a light chain CDR3 selected from the group consisting of SEQ ID NOs: 15 and 35, wherein the isolated antibody or antigen binding fragments thereof binds to human FXI and/or FXIa.

The invention also relates to an isolated antibody or antigen binding fragments thereof that binds FXI and/or FXIa having HCDR1, HCDR2, and HCDR3 and LCDR1, LCDR2, and LCDR3, wherein HCDR1, HCDR2, and HCDR3 comprises SEQ ID NOs: 3, 4, and 5, and LCDR1, LCDR2, LCDR3 comprises SEQ ID NOs: 13, 14, and 15; or HCDR1, HCDR2, and HCDR3 comprises SEQ ID NOs: 23, 24, and 25, and LCDR1, LCDR2, LCDR3 comprises SEQ ID NOs: 33, 34, and 35.

The invention also relates to an isolated antibody or antigen binding fragments thereof that binds FXI and/or FXIa having HCDR1, HCDR2, and HCDR3 and LCDR1, LCDR2, and LCDR3, wherein HCDR1, HCDR2, and HCDR3 comprises SEQ ID NOs: 43, 44, and 45, respectively, and LCDR1, LCDR2, LCDR3 comprises SEQ ID NOs: 47, 37, and 15, respectively.

The invention also relates to an isolated antibody or antigen binding fragments thereof that binds FXI and/or FXIa having HCDR1, HCDR2, and HCDR3 and LCDR1, LCDR2, and LCDR3, wherein HCDR1, HCDR2, and HCDR3 comprises SEQ ID NOs: 46, 4, and 5, respectively, and LCDR1, LCDR2, LCDR3 comprises SEQ ID NOs: 33, 14, and 15, respectively.

The invention also relates to an antibody or antigen binding fragment having HCDR1, HCDR2, and HCDR3 of the variable heavy chain of SEQ ID NOs: 9 and 29, and the LCDR1, LCDR2 and LCDR3 of the variable light chain of SEQ ID NOs: 19 and 39, as defined by Chothia. In another aspect of the invention the antibody or antigen binding fragment may have the HCDR1, HCDR2, and HCDR3 of the heavy chain variable domain sequence of SEQ ID NOs: 9 and 29, and the LCDR1, LCDR2 and LCDR3 of the light chain variable domain sequence of SEQ ID NOs: 19 and 39, as defined by Kabat.

The invention also relates to an antibody or antigen binding fragment having HCDR1, HCDR2, and HCDR3 of the variable heavy chain of SEQ ID NOs: 9 and 29, and the LCDR1, LCDR2 and LCDR3 of the variable light chain of SEQ ID NOs: 19 and 39, as defined by IMGT. In another aspect of the invention the antibody or antigen binding fragment may have the HCDR1, HCDR2, and HCDR3 of the heavy chain variable domain sequence of SEQ ID NOs: 9 and 29, and the LCDR1, LCDR2 and LCDR3 of the light chain variable domain sequence of SEQ ID NOs: 19 and 39, as defined by Combined.

In one aspect of the invention the isolated antibody or antigen binding fragments thereof includes a heavy chain variable domain sequence selected from the group consisting of SEQ ID NOs: 9 and 29. The isolated antibody or antigen binding fragment further can comprise a light chain variable domain sequence wherein the heavy chain variable domain and light chain variable domain combine to form an antigen binding site for FXIa. In particular the light chain variable domain sequence can be selected from SEQ ID NOs: 19 and 39 wherein said isolated antibody or antigen binding fragments thereof binds FXI and/or FXIa.

The invention also relates to an isolated antibody or antigen binding fragments thereof that includes a light chain variable domain sequence selected from the group consisting of SEQ ID NOs: 19 and 39, wherein said isolated antibody or antigen binding fragments thereof binds to human FXI and/or FXIa. The isolated antibody or antigen binding fragment may further comprise a heavy chain variable domain sequence wherein the light chain variable domain and heavy chain variable domain combine to form and antigen binding site for FXI and/or FXIa.

In particular, the isolated antibody or antigen binding fragments thereof that binds FXI and/or FXIa, may have heavy and light chain variable domains comprising the sequences of SEQ ID NOs: 9 and 19; or 19 and 39, respectively.

The invention further relates to an isolated antibody or antigen binding fragments thereof, that includes a heavy chain variable domain having at least 80%, 85%, 90%, 95%, 97%, 98%, or 99% sequence identity to a sequence selected from the group consisting of SEQ ID NOs: 9 and 29, wherein said antibody binds to FXI and/or FXIa. In one aspect, the isolated antibody or antigen binding fragments thereof also includes a light chain variable domain having at least 80%, 85%, 90%, 95%, 97%, 98%, or 99% sequence identity to a sequence selected from the group consisting of SEQ ID NOs: 19 and 39. In a further aspect of the invention, the isolated antibody or antigen binding fragment has an HCDR1, HCDR2, HCDR3, LCDR1, LCDR2 and LCDR3 as defined by Kabat and as described in Table 1. In a specific embodiment, the isolated antibody or antigen binding fragment has an HCDR1, HCDR2, HCDR3, LCDR1, LCDR2 and LCDR3 as defined by Chothia, IMGT, or Combined and as described in Table 1.

The invention also relates to an isolated antibody or antigen binding fragments thereof, having a light chain variable domain having at least 80%, 85%, 90%, 95%, 97%, 98%, or 99% sequence identity to a sequence selected from the group consisting of SEQ ID NOs: 19 and 39, wherein said antibody binds FXI and/or FXIa.

In another aspect of the invention, the isolated antibody, or antigen binding fragments thereof, that bind to FXI and/or FXIa may have a heavy chain comprising the sequence of SEQ ID NOs: 11 or 31. The isolated antibody can also include a light chain that can combine with the heavy chain to form an antigen binding site to human FXI and/or FXIa. In particular, the light chain may have a sequence comprising SEQ ID NOs: 21 or 41. In particular, the isolated antibody or antigen binding fragments thereof that binds FXI and/or FXIa, may have a heavy chain and a light chain comprising the sequences of SEQ ID NOs: 11 and 21; or 31 and 41, respectively.

The invention still further relates to an isolated antibody or antigen binding fragments thereof that includes a heavy chain having at least 90% sequence identity to a sequence selected from the group consisting of SEQ ID NOs: 11 or 31, wherein said antibody binds to FXI and/or FXIa. In one aspect, the isolated antibody or antigen binding fragments thereof also includes a light chain having at least 80%, 85%, 90%, 95%, 97%, 98%, or 99% sequence identity to a sequence selected from the group consisting of SEQ ID NOs: 21 or 41.

The invention still further relates to an isolated antibody or antigen binding fragments thereof that includes a light chain having at least 80%, 85%, 90%, 95%, 97%, 98%, or 99% sequence identity to a sequence selected from the group consisting of SEQ ID NOs: 21 or 41, wherein said antibody binds FXI and/or FXIa.

The invention also relates to compositions comprising the isolated antibody, or antigen binding fragments thereof, described herein, as well as, antibody compositions in combination with a pharmaceutically acceptable carrier. Specifically, the invention further includes pharmaceutical compositions comprising an antibody or antigen binding fragments thereof of Table 1, such as, for example antibody NOV1090 and NOV1401. The invention also relates to pharmaceutical compositions comprising a combination of two or more of the isolated antibodies or antigen binding fragments thereof of Table 1.

The invention also relates to an isolated nucleic acid sequence encoding the variable heavy chain having a sequence selected from SEQ ID NOs: 9 and 29. In particular the nucleic acid has a sequence at least 80%, 85%, 90%, 95%, 97%, 98%, or 99% sequence identity to a sequence selected from the group consisting of SEQ ID NOs: 10 and 30. In a further aspect of the invention the sequence is SEQ ID NOs: 10 or 30.

The invention also relates to an isolated nucleic acid sequence encoding the variable light chain having a sequence selected from SEQ ID NOs: 20 and 40. In particular the nucleic acid has a sequence at least 80%, 85%, 90%, 95%, 97%, 98%, or 99% sequence identity to a sequence selected from the group consisting of SEQ ID NOs: 20 and 40. In a further aspect of the invention the sequence is SEQ ID NOs: 20 and 40.

The invention also relates to an isolated nucleic acid comprising a sequence encoding an polypeptide that includes a light chain variable domain having at least 90% sequence identity to a sequence selected from the group consisting of SEQ ID NOs: 20 and 40.

The invention also relates to a vector that includes one or more of the nucleic acid molecules described herein.

The invention also relates to an isolated host cell that includes a recombinant DNA sequence encoding a heavy chain of the antibody described above, and a second recombinant DNA sequence encoding a light chain of the antibody described above, wherein said DNA sequences are operably linked to a promoter and are capable of being expressed in the host cell. It is contemplated that the antibody can be a human monoclonal antibody. It is also contemplated that the host cell is a non-human mammalian cell.

The invention also relates to a method of reducing FXI and/or FXIa expression, and/or intrinsic and/or common coagulation pathway activation, wherein the method includes the step of contacting a cell with an effective amount of a composition comprising the isolated antibody or antigen binding fragments thereof described herein.

The invention also relates to a method of inhibiting the binding of FXI and/or FXIa to FIX, wherein the method includes the step of contacting a cell with an effective amount of a composition comprising the isolated antibody or antigen binding fragments thereof described herein.

It is contemplated that the cell is a human cell. It is further contemplated that the cell is in a subject. In one embodiment, it is contemplated that the cell is a platelet. It is still further contemplated that the subject is human.

The invention also relates to a method of treating, improving, or preventing a thromboembolic disease in a subject, wherein the method includes the step of administering to the subject an effective amount of a composition comprising the antibody or antigen binding fragments thereof described herein. In one aspect, the thromboembolic disease is a thrombotic disorder (e.g., thrombosis, thrombic stroke, atrial fibrillation, stroke prevention in atrial fibrillation (SPAF), deep vein thrombosis, venous thromboembolism, and pulmonary embolism). It is contemplated that the subject is human.

Any of the foregoing isolated antibodies or antigen binding fragments thereof may be a monoclonal antibody or antigen binding fragments thereof.

Non-limiting embodiments of the disclosure are described in the following aspects:

1. An isolated anti-FXI and/or anti-FXIa antibody or fragment thereof that binds within the catalytic domain of FXI and/or FXIa.

2. An isolated antibody or fragment thereof that binds to one or more epitopes of anti-FXI and/or FXIa, wherein the epitope comprises two or more amino acid residues of Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

3. The isolated antibody or fragment of aspect 2, wherein the epitope comprises four or more amino acid residues of Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

4. The isolated antibody or fragment of aspect 2, wherein the epitope comprises six or more amino acid residues of Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

5. The isolated antibody or fragment of aspect 2, wherein the epitope comprises eight or more amino acid residues of Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

6. The isolated antibody or fragment of aspect 2, wherein the epitope comprises the residues of Pro410, Arg413, Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Lys527, Arg548, His552, Ser575, Ser594, Trp595, Gly596, Glu597, Arg602, Glu603, and Arg604.

7. The isolated antibody or fragment of aspect 2, wherein the epitope comprises amino acid residues of Pro410, Arg413, Lys527 and one or more amino acid residues of Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Arg548, His552, Ser575, Ser594, Trp595, Gly596, Glu597, Arg602, Glu603, and Arg604.

8. The isolated antibody or fragment of aspect 2, wherein the epitope comprises amino acid residues of Pro410, Arg413, Lys527 and four or more amino acid residues of Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Arg548, His552, Ser575, Ser594, Trp595, Gly596, Glu597, Arg602, Glu603, and Arg604.

9. The isolated antibody or fragment of aspect 2, wherein the epitope comprises amino acid residues of Pro410, Arg413, Lys527 and six or more amino acid residues of Leu415, Cys416, His431, Cys432, Tyr434, Gly435, Glu437, Tyr472, Lys473, Met474, Ala475, Glu476, Tyr521, Arg522, Lys523, Leu524, Arg525, Asp526, Arg548, His552, Ser575, Ser594, Trp595, Gly596, Glu597, Arg602, Glu603, and Arg604.

10. An isolated anti-FXI and/or anti-FXIa antibody or fragment thereof that binds within the catalytic domain of FXI and/or FXIa, wherein said antibody or fragment blocks FXI and/or FXIa binding to one or more of Factor IX, Factor XIIa, and thrombin.

11. The isolated antibody or fragment of aspect 10, wherein said antibody or fragment blocks FXI and/or FXIa binding to one or more of Factor IX, Factor XIIa, or thrombin, and other components of the coagulation pathway.

12. The isolated antibody or fragment of aspect 1, wherein said antibody or fragment blocks one or more of FIX, FXI, and FXIa binding to platelet receptors.

13. The isolated antibody or fragment of aspect 1, wherein said antibody or fragment prevents activation of the intrinsic or common coagulation pathways.

14. An isolated antibody or fragment thereof that binds to a human FXI and/or FXIa protein with a $K_D$ of less than or equal to 34 nM, as measured by BIACORE™ assay, or less than or equal to 4 pM, as measured by solution equilibrium titration assay (SET).

15. The isolated antibody or fragment of aspect 1, wherein said antibody or fragment comprises at least one complementarity determining region having at least 90% identity to at least one of the CDRs recited in Table 1.

16. The isolated antibody or fragment of aspect 1, wherein said antibody or fragment comprises a CDR1, CDR2, and CDR3 from Table 1.

17. An isolated variant of the antibody or fragment of aspect 1, wherein said antibody or fragment comprises a CDR1, CDR2, and CDR3 from Table 1, and wherein the variant has at least one to four amino acid changes in one of CDR1, CDR2, or CDR3.

18. The isolated antibody or fragment of aspect 1, wherein the antibody or fragment comprises a heavy chain CDR3 selected from the group consisting of SEQ ID NO: 5 and 25.

20. The isolated antibody or fragment of aspect 1, wherein the antibody or fragment comprises a VH selected from the group consisting of SEQ ID NO: 9 and 29 or an amino acid sequence with 90% identity thereof; and a VL selected from the group consisting of SEQ ID NO: 19 and 39 or an amino acid sequence with 90% identity thereof.

21. The isolated antibody or fragment of aspect 1, wherein the antibody or fragment comprises a VH selected from the group consisting of SEQ ID NO: 9 and 29 or an amino acid sequence with 95% identity thereof; and a VL selected from the group consisting of SEQ ID NO: 19 and 39 or an amino acid sequence with 95% identity thereof.

22. The isolated antibody or fragment of aspect 1, wherein the antibody or fragment comprises a VH selected from the group consisting of SEQ ID NO: 9 and 29 or an amino acid sequence with 97% identity thereof; and a VL selected from the group consisting of SEQ ID NO: 19 and 39 or an amino acid sequence with 97% identity thereof.

23. The isolated antibody or fragment of aspect 1, wherein the antibody or fragment comprises a variable heavy chain sequence selected from the group consisting of SEQ ID NO: 9 and 29.

24. The isolated antibody or fragment of aspect 1, wherein the antibody or fragment comprises a variable light chain sequence selected from the group consisting of SEQ ID NO: 19 and 39.

25. The isolated antibody or fragment of aspect 1, wherein the antibody or fragment comprises a variable heavy chain selected from the group consisting of SEQ ID NO: 9 and 29; and variable light chain sequence selected from the group consisting of SEQ ID NO: 19 and 39.

26. The isolated antibody or fragment of aspect 1, wherein the antibody or fragment selected from the group consisting of an antibody or fragment comprising a variable heavy chain of SEQ ID NO: 9 and a variable light chain sequence of SEQ ID NO: 19 and an antibody or fragment comprising a variable heavy chain of SEQ ID NO: 29 and a variable light chain sequence of SEQ ID NO: 39.

27. The isolated antibody or fragment of aspect 1, wherein the antibody or fragment comprises a heavy chain variable region CDR1 selected from the group consisting of SEQ ID NO: 46; CDR2 selected from the group consisting of SEQ ID NO: 4; CDR3 selected from the group consisting of 5; a light chain variable region CDR1 selected from the group consisting of SEQ ID NO: 33; CDR2 selected from the group consisting of SEQ ID NO: 14; and CDR3 selected from the group consisting of SEQ ID NO: 15.

28. The isolated antibody or fragment of aspect 1, wherein the antibody or fragment comprises a heavy chain variable region CDR1 selected from the group consisting of SEQ ID NO: 3 and 23; CDR2 selected from the group consisting of SEQ ID NO: 4 and 24; CDR3 selected from the group consisting of 5 and 25; a light chain variable region CDR1 selected from the group consisting of SEQ ID NO: 13 and 33; CDR2 selected from the group consisting of SEQ ID NO: 14 and 34; and CDR3 selected from the group consisting of SEQ ID NO: 15 and 35.

29. The isolated antibody or fragment of aspect 1, wherein the antibody or fragment comprises a heavy chain variable region CDR1 selected from the group consisting of SEQ ID NO: 6 and 26; CDR2 selected from the group consisting of SEQ ID NO: 7 and 27; CDR3 selected from the group consisting of 8 and 28; a light chain variable region CDR1 selected from the group consisting of SEQ ID NO: 16 and 36; CDR2 selected from the group consisting of SEQ ID NO: 17 and 37; and CDR3 selected from the group consisting of SEQ ID NO: 18 and 38.

30. The isolated antibody or fragment of aspect 1, wherein the antibody or fragment comprises a heavy chain variable region CDR1 of SEQ ID NO: 3; a heavy chain variable region CDR2 of SEQ ID NO: 4; a heavy chain variable region CDR3 of SEQ ID NO: 5; a light chain variable region CDR1 of SEQ ID NO: 13; a light chain variable region CDR2 of SEQ ID NO: 14; and a light chain variable region CDR3 of SEQ ID NO: 15.

31. The isolated antibody or fragment of aspect 1, wherein the antibody or fragment comprises a heavy chain variable region CDR1 of SEQ ID NO: 23; a heavy chain variable region CDR2 of SEQ ID NO: 24; a heavy chain variable region CDR3 of SEQ ID NO: 25; a light chain variable region CDR1 of SEQ ID NO: 33; a light chain variable region CDR2 of SEQ ID NO: 34; and a light chain variable region CDR3 of SEQ ID NO: 35.

32. The isolated antibody or fragment of aspect 1, wherein the antibody or fragment comprises a heavy chain variable region CDR1 of SEQ ID NO: 6; a heavy chain variable region CDR2 of SEQ ID NO: 7; a heavy chain variable region CDR3 of SEQ ID NO: 8; a light chain variable region CDR1 of SEQ ID NO: 16; a light chain variable region CDR2 of SEQ ID NO: 17; and a light chain variable region CDR3 of SEQ ID NO: 18.

33. The isolated antibody or fragment of aspect 1, wherein the antibody or fragment comprises a heavy chain variable region CDR1 of SEQ ID NO: 26; a heavy chain variable region CDR2 of SEQ ID NO: 27; a heavy chain variable region CDR3 of SEQ ID NO: 28; a light chain variable region CDR1 of SEQ ID NO: 36; a light chain variable region CDR2 of SEQ ID NO: 37; and a light chain variable region CDR3 of SEQ ID NO: 38.

34. A pharmaceutical composition comprising an antibody or fragment thereof of one of the preceding aspects and a pharmaceutically acceptable carrier.

35. The isolated antibody or fragment of aspect 1, wherein the antibody or fragment binds to the same epitope as an isolated antibody or fragment according to any previous aspect.

36. The isolated antibody or fragment of aspect 1, wherein the antibody or fragment competes for binding to a human FXI and/or FXIa protein with an isolated antibody or fragment according to any previous aspect.

37. The isolated antibody or fragment of aspect 1, wherein the antibody or fragment is selected from the group consisting of NOV1090 and NOV1401.

38. A method of treating a thromboembolic disorder comprising administering to a subject afflicted with a thromboembolic disorder an effective amount of a pharmaceutical composition comprising an antibody or fragment according to any previous aspect.

39. The method of aspect 38, wherein the subject is afflicated with one or more of ischemic stroke associated with atrial fibrillation and deep vein thrombosis.

40. The method of aspect 38, wherein the subject is afflicated with ischemic stroke associated with atrial fibrillation.

41. A method of treating a thromboembolic disorder comprising administering to a subject afflicted with a thromboembolic disorder an effective amount of a pharmaceutical composition comprising an antibody or fragment according to any previous aspect in combination with statin therapies.

42. A medicament comprising an antibody according to any previous aspect.

43. A nucleic acid coding for one or more of the antibodies according to any previous aspect.

44. A vector comprising the nucleic acid according to aspect 43.

45. A host cell comprising the vector of aspect 44.

46. The isolated antibody or fragment of aspect 1, wherein the antibody or fragment leads upon binding to the active FXI (FXIa) catalytic domain to FXIa changing its conformation to an inactive conformation, in which the N-terminal 4 residues, loops 145, 188 and 220 are shifted and/or disordered compared to the active conformation.

47. The isolated antibody or fragment of aspect 1, wherein the antibody or fragment upon binding to FXI prevents the FXI catalytic domain from assuming an active conformation, in which loops 145, 188 and 220 are ordered as in the structure of the FXIa catalytic domain.

48. The isolated antibody or fragment of aspect 1, wherein the antibody or fragment upon binding to FXI prevents the FXI catalytic domain from assuming an active conformation, in which the N-terminal 4 residues, loops 145, 188 and 220 are ordered as in the structure of the FXIa catalytic domain.

49. The isolated antibody or fragment of aspect 1, wherein the antibody or fragment upon binding to FXI prevents the FXI catalytic domain from assuming an active conformation by inducing conformational changes in the zymogen structure, further leading to an inhibited FXI conformation closely related to that observed when binding to FXI a.

50. The isolated antibody or fragment of aspect 1, wherein the antibody or fragment, upon binding to FXI and/or FXIa and forming an antibody:antigen complex with the catalytic domain of FXI and/or FXIa, causes a shift and/or disorientation of loops 145, 188 and 220 when compared with the uncomplexed structure of the catalytic domain of active Factor XI (FXIa).

51. The isolated antibody or fragment of aspect 1, wherein the antibody or fragment, upon binding to FXI and/or FXIa and forming an antibody:antigen complex with the catalytic domain of FXI and/or FXIa, causes a shift and/or disorientation of the N-terminal 4 residues, loops 145, 188 and 220 when compared with the uncomplexed structure of the catalytic domain of active Factor XI (FXIa).

52. The isolated antibody or fragment of aspect 1, wherein the antibody or fragment binds to active FXI (FXIa) and causes the FXI (FXIa) catalytic domain to change its conformation to an inactive conformation, in which loops 145, 188 and 220 are shifted and/or disoriented compared to the active conformation.

DEFINITIONS

Unless defined otherwise, all technical and scientific terms used herein have the same meaning as commonly understood by those of ordinary skill in the art to which this invention pertains.

The terms "FXI protein," "FXI antigen," and "FXI" are used interchangeably, and refers to the Factor XI protein in different species. Factor XI is the mammalian plasma coagulation factor XI, a glycoprotein present in human plasma at a concentration of 25-30 nM as a zymogen that when converted by limited proteolysis to an active serine protease, participates in the intrinsic pathway of blood coagulation.

The terms "FXIa protein," "FXIa antigen," and "FXIa", are used interchangeably, and refers to the activated FXI protein in different species. The zymogen Factor XI is converted into its active form, the coagulation factor XIa (FXIa), either via the contact phase of blood coagulation or through thrombin-mediated activation on the platelet surface. During this activation of factor XI, an internal peptide bond is cleaved in each of the two chains, resulting in the activated factor XIa, a serine protease composed of two heavy and two light chains held together by disulfide bonds. This serine protease FXIa converts the coagulation Factor IX into IXa, which subsequently activates coagulation Factor X (Xa). Xa then can mediate coagulation Factor II/Thrombin activation. For example, human FXI has the sequence as set out in Table 1 (SEQ ID NO:1), and has been described in previous reports and literature (Mandle R J Jr, et al. (1979) Blood; 54(4):850; NCBI Reference Sequence: AAA51985).

In the context of this invention, the terms "FXI" and "FXIa" (and the like) include mutants and variants of the natural FXI and FXIa protein, respectively, which have substantially the same amino acid sequence as that of the native primary structure (amino acid sequence) described in the above-mentioned reports.

The term "catalytic domain," "serine protease catalytic domain," and similar terms as used herein, means amino acids Ile370 to Val607, as counted from the Glu1 at the N-terminus of the mature protein that is in circulation. It can also be described as residues 388-625 at the C-terminus of FXI. As used herein, the term "active site" means the catalytic triad comprised of the amino acids His413, Asp462 and Se557. (Bane and Gailani (2014) Drug Disc. 19(9)).

The term "about" in relation to a numerical value x means, for example, x±10%. The term "antibody" as used herein means a whole antibody and any antigen binding fragment (i.e., "antigen-binding portion") or single chain thereof. A whole antibody is a glycoprotein comprising at least two heavy (H) chains and two light (L) chains interconnected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen binding portion" or "antigen binding fragment" of an antibody, as used herein, refers to one or more fragments of an intact antibody that retain the ability to specifically bind to a given antigen (e.g., Factor XIa (FXIa)). Antigen binding functions of an antibody can be performed by fragments of an intact antibody. Examples of binding fragments encompassed within the term antigen binding portion or antigen binding fragment of an antibody include a Fab fragment, a monovalent fragment consisting of the VL, VH, CL and CH1 domains; a F(ab)$_2$ fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341:544-546), which consists of a VH domain or a VL domain; and an isolated complementarity determining region (CDR).

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more antigen binding portions or fragments of an antibody. These antibody fragments are obtained using conventional techniques known to those of skill in the art, and the fragments are screened for utility in the same manner as are intact antibodies.

Antigen binding fragments can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH—CH1-VH—CH1) which, together with complementary light chain polypeptides, form a pair of antigen binding regions (Zapata et al., 1995 Protein Eng. 8(10):1057-1062; and U.S. Pat. No. 5,641,870).

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. As used herein, the term "high affinity" for an antibody or antigen binding fragments thereof (e.g., a Fab fragment) generally refers to an antibody, or antigen binding fragment, having a $K_D$ of $10^{-3}$M or less (e.g., a $K_D$ of $10^{-10}$ M or less, a $K_D$ of $10^{-11}$M or less, a $K_D$ of $10^{-12}$M or less, a $K_D$ of $10^{-13}$M or less, a $K_D$ of $10^{-14}$ M or less, etc.).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "binding specificity" as used herein refers to the ability of an individual antibody combining site to react with only one antigenic determinant.

The phrase "specifically (or selectively) binds" to an antibody (e.g., a FXI and/or FXIa-binding antibody) refers to a binding reaction that is determinative of the presence of a cognate antigen (e.g., a human FXI and/or FXIa or cynomolgus FXI and/or FXIa) in a heterogeneous population of proteins and other biologics. The phrases "an antibody recognizing an antigen" and "an antibody specific for an antigen" are used interchangeably herein with the term "an antibody which binds specifically to an antigen".

The term "FXI and/or FXIa mediated" refers to the fact that FXI and/or FXIa mediates the intrinsic and/or common coagulation pathways by directly or indirectly activating Factor IX (also known as FIX), Factor X (FX), and/or thrombin, and/or by binding to platelet receptors.

The term "hemostasis" represents the principal mechanisms for arresting the flow of blood at sites of injury and restoring vascular patency during wound healing, respectively. During normal hemostasis and pathological thrombosis, three mechanisms become activated simultaneously: primary hemostasis meaning the interactions of activated platelets with the vessel wall, the formation of fibrin, and a process termed as fibrinolysis.

The terms "coagulation and coagulation cascade," "cascade model of coagulation," and the like, refer to the protein based system which serves to stabilize a clot that has formed to seal up a wound. The coagulation pathway is a proteolytic cascade. Each enzyme of the pathway is present in the plasma as a Zymogen (in an inactive form), which on activation undergoes proteolytic cleavage to release the active factor from the precursor molecule. The coagulation cascade functions as a series of positive and negative feedback loops which control the activation process. The ultimate goal of the pathway is to produce thrombin, which can then convert soluble fibrinogen into fibrin that forms a clot.

The process of generation of thrombin can be divided into three phases: the intrinsic and extrinsic pathways, which provide alternative routes for the generation of an active clotting factor: FXa (Activated Factor-X), and the final common pathway, which results in thrombin formation (Hoffman M. M. and Monroe D. M. (2005) Curr Hematol Rep. 4:391-396; Johne J, et al. (2006) Biol Chem. 387:173-178).

"Platelet aggregation" refers to the process whereby when a break in a blood vessel occurs, substances are exposed that normally are not in direct contact with the blood flow. These substances (primarily collagen and von Willebrand factor) allow the platelets to adhere to the broken surface. Once a platelet adheres to the surface, it releases chemicals that attract additional platelets to the damaged area, referred to as platelet aggregation. These two processes are the first responses to stop bleeding.

A "thromboembolic disorder," or similar terms as used herein, refer to any number of conditions or diseases in which the intrinsic and/or common coagulation pathways are aberrantly activated or are not naturally deactivated (e.g., without therapeutic means). These conditions include but are not limited to thrombic stroke, atrial fibrillation, stroke prevention in atrial fibrillation (SPAF), deep vein thrombosis, venous thromboembolism, and pulmonary embolism. These can also include catheter-related conditions (e.g., Hickman catheter in oncology patients) in which catheters become thrombosed, and extracorporeal membrane oxygenation (ECMO), in which the tubing develops clots.

A "thromboembolic," or similar terms as used herein, can also refer to any number of the following, which the anti-FXI and/or FXIa Abs or antigen binding fragments thereof of the invention can be used to prevent or treat:
thromboembolism in subjects with suspected or confirmed cardiac arrhythmia such as paroxysmal, persistent or permanent atrial fibrillation or atrial flutter;
stroke prevention in atrial fibrillation (SPAF), a subpopulation of which is AF patients undergoing percutaneous coronary interventions (PCI);
acute venous thromboembolic events (VIE) treatment and extended secondary VIE prevention in patients at high risk for bleeding;
cerebral and cardiovascular events in secondary prevention after transient ischemic attack (IIA) or non-disabling stroke and prevention of thromboembolic events in heart failure with sinus rhythm;
clot formation in left atrium and thromboembolism in subjects undergoing cardioversion for cardiac arrhythmia;
thrombosis before, during and after ablation procedure for cardiac arrhythmia;
venous thrombosis, this includes but not exclusively, treatment and secondary prevention of deep or superficial veins thrombosis in the lower members or upper member, thrombosis in the abdominal and thoracic veins, sinus thrombosis and thrombosis of jugular veins;
thrombosis on any artificial surface in the veins like catheter or pacemaker wires;
pulmonary embolism in patients with or without venous thrombosis;
Chronic Thromboembolic Pulmonary Hypertension (CTEPH);
arterial thrombosis on ruptured atherosclerotic plaque, thrombosis on intra-arterial prosthesis or catheter and thrombosis in apparently normal arteries, this includes but not limited to acute coronary syndromes, ST elevation myocardial infarction, non ST elevation myocardial infarction, unstable angina, stent thrombosis, thrombosis of any artificial surface in the arterial system and thrombosis of pulmonary arteries in subjects with or without pulmonary hypertension;
thrombosis and thromboembolism in patients undergoing percutaneous coronary interventions (PCI);
cardioembolic and cryptogenic strokes;
thrombosis in patients with invasive and non-invasive cancer malignancies;
thrombosis over an indwelling catheter;
thrombosis and thromboembolism in severely ill patients;
cardiac thrombosis and thromboembolism, this includes but not exclusively cardiac thrombosis after myocardial infarction, cardiac thrombosis related to condition such as cardiac aneurysm, myocardial fibrosis, cardiac enlargement and insufficiency, myocarditis and artificial surface in the heart;
thromboembolism in patients with valvular heart disease with or without atrial fibrillation;
thromboembolism over valvular mechanic or biologic prostheses;
thromboembolism in patients who had native or artificial cardiac patches, arterial or venous conduit tubes after heart repair of simple or complex cardiac malformations;
venous thrombosis and thromboembolism after knee replacement surgery, hip replacement surgery, and orthopedic surgery, thoracic or abdominal surgery;
arterial or venous thrombosis after neurosurgery including intracranial and spinal cord interventions;
congenital or acquired thrombophilia including but not exclusively factor V Leiden, prothrombin mutation, antithrombin III, protein C and protein S deficiencies, factor XIII mutation, familial dysfibrinogenemia, congenital deficiency of plasminogen, increased levels of factor XI, sickle cell disease, antiphospholipid syndrome, autoimmune disease, chronic bowel disease, nephrotic syndrome, hemolytic uremia, myeloproliferative disease, disseminated intra vascular coagulation, paroxysmal nocturnal hemoglobinuria and heparin induced thrombopenia;
thrombosis and thromboembolism in chronic kidney disease; and
thrombosis and thromboembolism in patients undergoing hemodialysis and in patients undergoing extra-corporal membrane oxygenation.

The term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. Two antibodies are said to "compete" if one antibody is shown to bind the same epitope as the second antibody in a competitive binding assay, by any of the methods well known to those of skill in the art.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo).

The term "human monoclonal antibody" refers to antibodies displaying a single binding specificity which have variable regions in which both the framework and CDR regions are derived from human sequences. In one embodiment, the human monoclonal antibodies are prepared using phage display methods for screening libraries of human immunoglobulin genes.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239:1534-1536, 1988; Padlan, Molec. Immun., 28:489-498, 1991; and Padlan, Molec. Immun., 31:169-217, 1994. Other examples of human engineering technology include, but are not limited to Xoma technology disclosed in U.S. Pat. No. 5,766,886.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, John Wiley & Sons, Inc. (Ringbou ed., 2003)).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available on the world wide web at gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "isolated antibody" refers to an antibody that is substantially free of other antibodies having different antigenic specificities (e.g., an isolated antibody that specifically binds FXI and/or FXIa is substantially free of antibodies that specifically bind antigens other than FXI and/or FXIa). An isolated antibody that specifically binds FXI and/or FXIa may, however, have cross-reactivity to other antigens. Moreover, an isolated antibody may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e. $k_d/k_a$) and is expressed as a molar concentration (M). $K_D$ values for antibodies can be determined using methods well established in the art. Methods for determining the $K_D$ of an antibody include measuring surface plasmon resonance using a biosensor system such as a BIACORE™ system, or measuring affinity in solution by solution equilibrium titration (SET).

The terms "monoclonal antibody" or "monoclonal antibody composition" as used herein refer to a preparation of antibody molecules of single molecular composition. A monoclonal antibody composition displays a single binding specificity and affinity for a particular epitope.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "operably linked" refers to a functional relationship between two or more polynucleotide (e.g., DNA) segments. Typically, the term refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term, "optimized" means that a nucleotide sequence has been altered to encode an amino acid sequence using codons that are preferred in the production cell or organism, generally a eukaryotic cell, for example, a cell of *Pichia*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germ line VH and VL sequences, may not naturally exist within the human antibody germline repertoire in vivo.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "subject" includes human and non-human animals. Non-human animals include all vertebrates (e.g.: mammals and non-mammals) such as, non-human primates (e.g.: cynomolgus monkey), sheep, rabbit, dog, cow, chickens, amphibians, and reptiles. Except when noted, the terms "patient" or "subject" are used herein interchangeably. As used herein, the terms "cyno" or "cynomolgus" refer to the cynomolgus monkey (*Macaca fascicularis*). In specific aspects, a patient or subject is a human.

As used herein, the term "treating" or "treatment" of any disease or disorder (e.g., a thromboembolic disorder) refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

"Prevention" as it relates to indications described herein, including, e.g., a thromboembolic disorder, means any action that prevents or slows a worsening in e.g., a thromboembolic disease parameters, as described below, in a patient at risk for said worsening.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, such as an adeno-associated viral vector (AAV, or AAV2), wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

BRIEF DESCRIPTION OF THE DRAWINGS

FIG. 4A shows the X-ray structure of the NOV1401 Fab-FXI CD complex. The FXI catalytic domain is shown as grey surface, the Fab as ribbon in light grey (light chain) and dark grey (heavy chain). FIG. 4B shows the X-ray structure of the NOV1401 Fab-FXI CD complex in superposition with the FXI zymogen. The FXI catalytic domain is shown as ribbon in grey. The variable domains of the Fab are shown as a ribbon in light gray (VL) and dark gray (VH). Superimposed is the zymogen structure including the four apple domains as dark gray ribbon at the structure's bottom (PDB 2F83). The activation cleavage site (Ile370) is indicated.

FIG. 5A shows a view of the FXIa active site prior to Fab binding. FXIa is represented as a ribbon with a transparent surface. Sections of the structure that change conformation upon Fab binding are labelled (loop145, loop188, and loop220). The S1 and S1' subpockets are indicated. FIG. 5B shows the inactive conformation of FXI in the Fab-complex (Fab not shown).

FIG. 6A shows inhibition of Factor XIa activity by NOV1401. Representative compound response curve of antibody NOV1401 inhibiting the enzymatic activity of full length human FXIa. The assay measures the cleavage of a fluorescently labelled peptide as is described in example 3. Using the non-linear curve fit with a logistic fit model [y=A2+(A1−A2)/(1+(x/IC50)^p), where y is the %-inhibition at the inhibitor concentration, x. A1 is the lowest inhibition value, and A2 the maximum inhibition value. The exponent, p, is the Hill coefficient] on this representative data set leads to an IC$_{50}$ value of 160 pM. FIG. 6B shows an aPTT compound response curve. Representative compound response curve of antibody NOV1401 prolonging coagulation time in the aPTT assay using pooled human plasma. The assay measures the time to coagulation after initiating the intrinsic clotting cascade in presence of different concentrations of NOV1401, as described in Example 4. The black line represents a fit using a logistics non-linear fit model. The dotted line represents the baseline coagulation time of pooled human plasma in absence of NOV1401. The baseline coagulation time is 32.3 seconds, and is indicated with a grey dashed line in the graph. The grey dotted line indicates the antibody concentration at which the clotting time is doubled compared to baseline, i.e. the 2×aPTT value, which is 14 nM. FIG. 6C shows a TGA response curve. A representative compound response curve of antibody NOV1401 inhibiting thrombin generation in the TGA with pooled human plasma is shown. The assay measures the effects of different concentrations of NOV1401 on FXI-dependent thrombin generation through the so-called thrombin→FXIa feed-forward loop that can be triggered by very low tissue factor (TF) concentrations as described in Example 4. The black line represents a fit using a four-parameter dose-response curve model. The dotted line represents the residual thrombin concentration due to thrombin generation induced by small amounts of TF. An IC$_{50}$ value of 24 nM and a residual thrombin concentration of 159 nM (dotted line) were calculated for this compound response curve.

FIG. 7A shows the effect on aPTT, measured on study days 2, 23, and 79. aPTT increased by 2.1- to 3-fold in all animals receiving NOV1401 and remained elevated throughout the dosing phase of the study. No dose-dependency was observed and no gender-related differences were noted. FIG. 7B shows the effect on FXI:C, measured on study days 2, 23 and 79 and depicted as percent of plasma FXI activity. FXI:C decreased in all animals receiving NOV1401 to levels of 5-12% and remained at these levels throughout the dosing phase of the study. No dose-dependency was observed and no gender-related differences were noted.

DETAILED DESCRIPTION

Figure 1A:
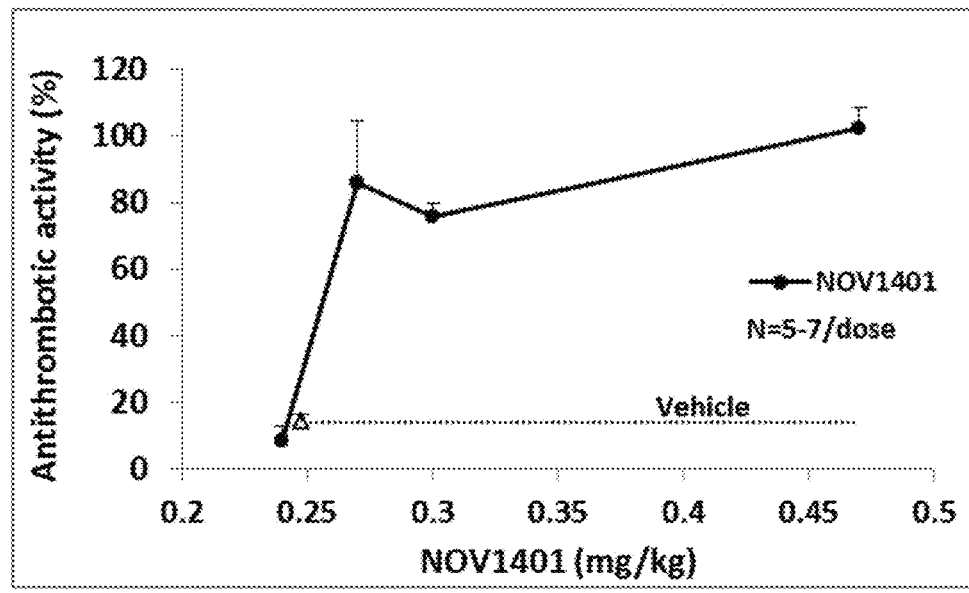
FIGS. 1A-C show the effect of NOV1401 on FeCl$_3$-induced thrombosis in FXI$^{-/-}$ mice reconstituted with human FXI protein. NOV1401 dose-dependently inhibited thrombosis. The antibody prolonged aPTT to the same extent as in untreated FXI$^{-/-}$ mice.

The present invention is based, in part, on the discovery of antibody molecules that specifically bind to FXIa and inhibit its biological activities. The invention relates to both full IgG format antibodies as well as antigen binding fragments thereof, such as Fab fragments (e.g., antibodies NOV1090 and NOV1401).

Accordingly, the present invention provides antibodies that specifically bind to FXI and/or FXIa (e.g., human, rabbit, and cynomolgus monkey FXI and/or FXIa), pharmaceutical compositions, production methods, and methods of use of such antibodies and compositions.

Factor XI

FXI holds important roles in both intrinsic and extrinsic coagulation pathways and in bridging the initiation and amplification phases of plasmatic hemostasis. Both Factor XIIa and thrombin can activate FXI, resulting in a sustained thrombin generation and fibrinolysis inhibition. FXI plays a minor role in normal hemostasis in a high tissue factor environment "after vessel injury" whereas it appears to play a key role in thrombosis. Severe Factor XI deficiency is associated with a lower incidence of ischemic stroke and venous thromboembolic events (Salomon et al 2008; Salomon, et al. (2011) Thromb Haemost.; 105:269-73). Bleeding manifestations in subjects with severe factor XI deficiency are infrequent, often mild, injury-induced and affect preferably tissues with increased fibrinolytic activity such as the oral mucosa, nasal mucosa and urinary tract (Salomon et al 2011). Bleeding in critical organs is extremely rare or not existing.

Plasma coagulation is a sequential process by which coagulation factors in the blood interact and are activated, ultimately resulting in fibrin generation and clot formation. In the classical cascade model of coagulation, the process of fibrin generation can be initiated by two distinct pathways, i.e., the intrinsic and the extrinsic pathway, respectively (Mackman, 2008).

In the extrinsic pathway, vessel injury allows extravascular tissue factor (TF) to interact with and activate factor VII (FVII), which sequentially leads to the activation of factor X and prothrombin. The active thrombin ultimately converts soluble fibrinogen into fibrin. The extrinsic pathway is central for hemostasis, interfering with coagulation factors in this pathway results in a risk of bleeding.

In the intrinsic pathway, factor XII may in some cases be activated by a process referred to as contact activation. Generation of activated factor XIIa leads to the sequential activations of factor XI and factor IX. As factor IXa activates factor X, the extrinsic and intrinsic pathways converge at this stage (at the common pathway). Thrombin activity is boosted by amplifying its own generation through a feed-forward loop in which thrombin activates factor XI independently of factor XII. This feed-forward loop contributes to sustained thrombus growth but is only minimally involved in hemostasis, as the strong activation by extravascular tissue factor is sufficient to clot formation. The intrinsic pathway therefore is not substantially involved in hemostasis (Gailani and Renné (2007) Arterioscler Thromb Vasc Biol. 2007, 27(12):2507-13, Müller, Gailiani, and Renné 2011).

Preclinical studies using a variety of approaches to inhibit FXI or FXIa across a variety of species have contributed to the validation of this target. FXI−/− mice are resistant to experimental venous (Wang, et al. (2006) J Thromb Haemost; 4:1982-8) and arterial (Wang, et al. (2005) J Thromb Haemost; 3:695-702) thrombosis. Treatment of mice with an antibody (Ab, 14E11) that blocks the activation of FXI by FXIIa resulted in inhibition of experimental thrombosis (Cheng, et al. (2010) Blood, 116:3981-9) and reduced cerebral infarct size in a mouse model of ischemic stroke (Leung, et al. (2012) Transl Stroke Res 2012; 3:381-9). In baboons administered an anti-FXI Ab that blocks binding and activation of FIX by FXIa, reduced growth of platelet-rich thrombi was observed on collagen-coated vascular grafts (Tucker, et al. (2009) Blood 2009; 113:936-44), and similar results were found with 14E11 in this model (Cheng 2010). Excessive bleeding was not noted in any of these studies.

Blocking FXI synthesis with antisense oligonucleotides in mice (Zhang, et al. (2010) Blood 2010; 116:4684-92), cynomolgus monkeys (Younis, et al. (2012) Blood 2012; 119:2401-8), and baboons (Crosby, et al. (2013) Arterioscler Thromb Vasc Biol 2013; 33:1670-8) resulted in antithrombotic and anticoagulant effects without excessive bleeding. Moreover, similar effects have been produced by blocking FXIa with low molecular weight inhibitors in venous and arterial models of thrombosis in rats (Schumacher, et al. (2007) Eur J Pharmacol 2007; 570:167-74) and rabbits (Wong, et al. (2011) J Thromb Thrombolysis 2011; 32:129-37).

Patients with severe FXI deficiency rarely bleed spontaneously and they show only mild trauma-induced bleeding, except in tissues with high fibrinolytic activity. The rarity of severe FXI deficiency necessitates the use of population studies for revealing the thrombotic profile of these patients relative to the general population. Notably, such studies report the incidence of ischemic stroke (Salomon 2008) and deep vein thrombosis (DVT) (Salomon, et al. (2011) Blood 2008; 111: 4113-17) to be reduced in these patients. Thus, the number of ischemic strokes (N=1) observed in 115 patients with severe FXI deficiency was less (p<0.003) than the expected incidence (N=8.6) in the general population of Israel, while the incidence of DVT (N=0) was lower (p<0.019) in patients with severe FXI deficiency than expected in the control population (N=4.7). Conversely, individuals with FXI levels above the 90th percentile had a two-fold risk of developing DVT (Meijers, et al. (2000) N Engl J Med. 2000; 342:696-701).

Recently, patients undergoing total knee replacement, a procedure that predisposes to DVT, were treated with FXI antisense therapy or standard of care (enoxaparin). The antisense group (300 mg) showed a 7-fold decreased incidence in venous thrombosis and fewer (not significant) bleeding events compared to standard of care (Büller et al, (2014) N Engl J Med. 372(3):232-40. doi: 10.1056/NEJMoa1405760. Epub 2014 Dec. 7).

Taken together, the above studies strongly support FXI as a valid target for antithrombotic therapy.

FXIa Antibodies & Antigen Binding Fragments

The present invention provides antibodies that specifically bind to FXI and/or FXIa. In some embodiments, the present invention provides antibodies that specifically bind to human, rabbit, and cynomolgus monkey FXI and/or FXIa. Antibodies of the invention include, but are not limited to, the human monoclonal antibodies and Fabs, isolated as described in the Examples.

The present invention provides antibodies that specifically bind a FXI and/or FXIa protein (e.g., human, rabbit, and cynomolgus monkey FXI and/or FXIa), wherein the antibodies comprise a VH domain having an amino acid sequence of SEQ ID NOs: 9 and 29. The present invention also provides antibodies that specifically bind to a FXI and/or FXIa protein, wherein the antibodies comprise a VH CDR having an amino acid sequence of any one of the VH CDRs listed in Table 1, infra. In particular, the invention provides antibodies that specifically bind to an FXI and/or FXIa protein (e.g., human, rabbit, and cynomolgus monkey FXI and/or FXIa), wherein the antibodies comprise (or alternatively, consist of) one, two, three, or more VH CDRs having an amino acid sequence of any of the VH CDRs listed in Table 1, infra.

The present invention provides antibodies that specifically bind to a FXIa protein, said antibodies comprising a VL domain having an amino acid sequence of SEQ ID NOs: 19 or 39. The present invention also provides antibodies that specifically bind to an FXI and/or FXIa protein (e.g., human, rabbit, and cynomolgus monkey FXI and/or FXIa), said antibodies comprising a VL CDR having an amino acid sequence of any one of the VL CDRs listed in Table 1, infra. In particular, the invention provides antibodies that specifically bind to an FXIa protein (e.g., human, rabbit, and cynomolgus monkey FXI and/or FXIa), said antibodies comprising (or alternatively, consisting of) one, two, three or more VL CDRs having an amino acid sequence of any of the VL CDRs listed in Table 1, infra.

Other antibodies of the invention include amino acids that have been mutated, yet have at least 60, 70, 80, 85, 90 or 95 percent identity in the CDR regions with the CDR regions depicted in the sequences described in Table 1. In some embodiments, it includes mutant amino acid sequences wherein no more than 1, 2, 3, 4 or 5 amino acids have been mutated in the CDR regions when compared with the CDR regions depicted in the sequence described in Table 1.

The present invention also provides nucleic acid sequences that encode VH, VL, the full length heavy chain, and the full length light chain of the antibodies that specifically bind to a FXI and/or FXIa protein (e.g., human, rabbit, and cynomolgus monkey FXIa). Such nucleic acid sequences can be optimized for expression in mammalian cells (for example, Table 1 shows the optimized nucleic acid sequences for the heavy chain and light chain of antibodies of the invention).

TABLE 1

Examples of FXIa Antibodies, Fabs and FXIa Proteins.

| Sequence Description | Sequence Identifier (SEQ ID NO:) | Amino acid or polynucleotide sequence |
|---|---|---|
| Human FXIa full-length protein sequence (NCBI Reference Sequence: AAA51985) | 1 | MIFLYQVVHF ILFTSVSGEC VTQLLKDTCF EGGDITTVFT PSAKYCQVVC TYHPRCLLFT FTAESPSEDP TRWFTCVLKD SVTETLPRVN RTAAISGYSF KQCSHQISAC NKDIYVDLDM KGINYNSSVA KSAQECQERC TDDVHCHFFT YATRQFPSLE HRNICLLKHT QTGTPTRITK LDKVVSGFSL KSCALSNLAC IRDIFPNTVF ADSNIDSVMA PDAFVSGRIC THHPGCLFFT FFSQEWPKES QRNLCLLKTS ESGLPSTRIK KSKALSGFSL QSCRHSIPVF CHSSFYHDTD FLGEELDIVA AKSHEACQKL CTNAVRCQFF TYTPAQASCN EGKGKCYLKL SSNGSPTKIL HGRGGISGYT LRLCKMDNEC TTKIKPRIVG GTASVRGEWP WQVTLHTTSP TQRHLCGGSI IGNQWILTAA HCFYGVESPK ILRVYSGILN QSEIKEDTSF FGVQEIIIHD QYKMAESGYD IALLKLETTV NYTDSQRPIC LPSKGDRNVI YTDCWVTGWG YRKLRDKIQN TLQKAKIPLV TNEECQKRYR GHKITHKMIC AGYREGGKDA CKGDSGGPLS CKHNEVWHLV GITSWGEGCA QRERPGVYTN VVEYVDWILE KTQAV |
| Human FXIa full-length nucleotide sequence (NCBI Reference Sequence: NM_000128.3) | 2 | AGGCACACAG GCAAAATCAA GTTCTACATC TGTCCCTGTG TATGTCACTT GTTTGAATAC GAAATAAAAT TAAAAAAATA AATTCAGTGT ATTGAGAAAG CAAGCAATTC TCTCAAGGTA TATTTCTGAC ATACTAAGAT TTTAACGACT TTCACAAATA TGCTGTACTG AGAGAGAATG TTACATAACA TTGAGAACTA GTACAAGTAA ATATTAAAGT GAAGTGACCA TTTCCTACAC AAGCTCATTC AGAGGAGGAT GAAGACCATT TTGGAGGAAG AAAAGCACCC TTATTAAGAA TTGCAGCAAG TAAGCCAACA AGGTCTTTTC AGGATGATTT TCTTATATCA AGTGGTACAT TTCATTTTAT TTACTTCAGT TTCTGGTGAA TGTGTGACTC AGTTGTTGAA GGACACCTGC TTTGAAGGAG GGGACATTAC TACGGTCTTC ACACCAAGCG CCAAGTACTG CCAGGTAGTC TGCACTTACC ACCCAAGATG TTTACTCTTC ACTTTCACGG CGGAATCACC ATCTGAGGAT CCCACCCGAT GGTTTACTTG TGTCCTGAAA GACAGTGTTA CAGAAACACT GCCAAGAGTG AATAGGACAG CAGCGATTTC TGGGTATTCT TTCAAGCAAT GCTCACACCA AATAAGCGCT TGCAACAAAG ACATTTATGT GGACCTAGAC ATGAAGGGCA TAAACTATAA CAGCTCAGTT GCCAAGAGTG CTCAAGAATG CCAAGAAAGA TGCACGGATG ACGTCCACTG CCACTTTTTC ACGTACGCCA CAAGGCAGTT TCCCAGCCTG GAGCATCGTA ACATTTGTCT ACTGAAGCAC ACCCAAACAG GGACACCAAC CAGAATAACG AAGCTCGATA AAGTGGTGTC TGGATTTTCA CTGAAATCCT GTGCACTTTC TAATCTGGCT TGTATTAGGG ACATTTTCCC TAATACGGTG TTTGCAGACA GCAACATCGA CAGTGTCATG GCTCCCGATG CTTTTGTCTG TGGCCGAATC TGCACTCATC ATCCCGTTTG CTTGTTTTTT ACCTTCTTTT CCCAGGAATG GCCCAAAGAA TCTCAAAGAA ATCTTTGTCT CCTTAAAACA TCTGAGAGTG GATTGCCCAG TACACGCATT AAAAAGAGCA AAGCTCTTTC TGGTTTCAGT CTACAAAGCT GCAGGCACAG CATCCCAGTG TTCTGCCATT CTTCATTTTA CCATGACACT GATTTCTTGG GAGAAGAACT GGATATTGTT GCTGCAAAAA GTCACGAGGC CTGCCAGAAA CTGTGCACCA ATGCCGTCCG CTGCCAGTTT TTTACCTATA CCCCAGCCCA AGCATCCTGC AACGAAGGGA |

TABLE 1-continued

Examples of FXIa Antibodies, Fabs and FXIa Proteins.

| Sequence Description | Sequence Identifier (SEQ ID NO:) | Amino acid or polynucleotide sequence |
|---|---|---|
| | | AGGGCAAGTG TTACTTAAAG CTTTCTTCAA ACGGATCTCC AACTAAAATA CTTCACGGGA GAGGAGGCAT CTCTGGATAC ACATTAAGGT TGTGTAAAAT GGATAATGAG TGTACCACCA AAATCAAGCC CAGGATCGTT GGAGGAACTG CGTCTGTTCG TGGTGAGTGG CCGTGGCAGG TGACCCTGCA CACAACCTCA CCCACTCAGA GACACCTGTG TGGAGGCTCC ATCATTGGAA ACCAGTGGAT ATTAACAGCC GCTCACTGTT TCTATGGGGT AGAGTCACCT AAGATTTTGC GTGTCTACAG TGGCATTTTA AATCAATCTG AAATAAAAGA GGACACATCT TTCTTTGGGG TTCAAGAAAT AATAATCCAT GATCAGTATA AATGGCAGA AAGCGGGTAT GATATTGCCT TGTTGAAACT GGAAACCACA GTGAATTACA CAGATTCTCA ACGACCCATA TGCCTGCCTT CCAAAGGAGA TAGAAATGTA ATATACACTG ATTGCTGGGT GACTGGATGG GGGTACAGAA AACTAAGAGA CAAAATACAA AATACTCTCC AGAAAGCCAA GATACCCTTA GTGACCAACG AAGAGTGCCA GAAGAGATAC AGAGGACATA AAATAACCCA TAAGATGATC TGTGCCGGCT ACAGGGAAGG AGGGAAGGAC GCTTGCAAGG GAGATTCGGG AGGCCCTCTG TCCTGCAAAC ACAATGAGGT CTGGCATCTG GTAGGCATCA CGAGCTGGGG CGAAGGCTGT GCTCAAAGGG AGCGGCCAGG TGTTTACACC AACGTGGTCG AGTACGTGGA CTGGATTCTG GAGAAAACTC AAGCAGTGTG AATGGGTTCC CAGGGGCCAT TGGAGTCCCT GAAGGACCCA GGATTTGCTG GGAGAGGGTG TTGAGTTCAC TGTGCCAGCA TGCTTCCTCC ACAGTAACAC GCTGAAGGGG CTTGGTGTTT GTAAGAAAAT GCTAGAAGAA AACAAACTGT CACAAGTTGT TATGTCCAAA ACTCCCGTTC TATGATCGTT GTAGTTTGTT TGAGCATTCA GTCTCTTTGT TTTTGATCAC GCTTCTATGG AGTCCAAGAA TTACCATAAG GCAATATTTC TGAAGATTAC TATATAGGCA GATATAGCAG AAAATAACCA AGTAGTGGCA GTGGGGATCA GGCAGAAGAA CTGGTAAAAG AAGCCACCAT AAATAGATTT GTTCGATGAA AGATGAAAAC TGGAAGAAAG GAGAACAAAG ACAGTCTTCA CCATTTTGCA GGAATCTACA CTCTGCCTAT GTGAACACAT TTCTTTTGTA AAGAAAGAAA TTGATTGCAT TTAATGGCAG ATTTTCAGAA TAGTCAGGAA TTCTTGTCAT TTCCATTTTA AAATATATAT TAAAAAAAAT CAGTTCGAGT AGACACGAGC TAAGAGTGAA TGTGAAGATA ACAGAATTTC TGTGTGGAAG AGGATTACAA GCAGCAATTT ACCTGGAAGT GATACCTTAG GGGCAATCTT GAAGATACAC TTTCCTGAAA AATGATTGT GATGGATTGT ATATTTATTT AAAATATCTT GGGAGGGGAG GCTGATGGAG ATAGGGAGCA TGCTCAAACC TCCCTAAGAC AAGCTGCTGC TGTGACTATG GGCTCCCAAA GAGCTAGATC GTATATTTAT TTGACAAAAA TCACCATAGA CTGCATCCAT ACTACAGAGA AAAAACAATT AGGGCGCAAA TGGATAGTTA CAGTAAAGTC TTCAGCAAGC AGCTGCCTGT ATTCTAAGCA CTGGGATTTT CTGTTTCGTG CAAATATTTA TCTCATTATT GTTGTGATCT AGTTCAATAA CCTAGAATTT GAATTGTCAC CACATAGCTT TCAATCTGTG CCAACAACTA TACAATTCAT CAAGTGTG |
| NOV1090 | | |
| HCDR1 (Kabat) | 3 | TAAMS |
| HCDR2 (Kabat) | 4 | GISGSGSSTYYADSVKG |
| HCDR3 (Kabat) | 5 | ELSYLYSGYYFDY |
| HCDR1 (Chothia) | 6 | GFTFSTA |
| HCDR2 (Chothia) | 7 | SGSGSS |
| HCDR3 (Chothia) | 8 | ELSYLYSGYYFDY |
| HCDR1 (IMGT) | 43 | GFTFSTAA |
| HCDR2 (IMGT) | 44 | ISGSGSST |
| HCDR3 (IMGT) | 45 | ARELSYLYSGYYFDY |
| HCDR1 (Combined) | 46 | GFTFSTAAMS |
| HCDR2 (Combined) | 4 | GISGSGSSTYYADSVKG |

TABLE 1-continued

Examples of FXIa Antibodies, Fabs and FXIa Proteins.

| Sequence Description | Sequence Identifier (SEQ ID NO:) | Amino acid or polynucleotide sequence |
|---|---|---|
| HCDR3 (Combined) | 5 | ELSYLYSGYYFDY |
| VH | 9 | QVQLLESGGGLVQPGGSLRLSCAASGFTFSTAAMSWVRQAPGK<br>GLEWVSGISGSGSSTYYADSVKGRFTISRDNSKNTLYLQMNSL<br>RAEDTAVYYCARELSYLYSGYYFDYWGQGTLVTVSS |
| DNA encoding VH | 10 | CAGGTGCAATTGCTGGAAAGCGGCGGTGGCCTGGTGCAGCCGG<br>GTGGCAGCCTGCGTCTGAGCTGCGCGGCGTCCGGATTCACCTT<br>TTCTACTGCTGCTATGTCTTGGGTGCGCCAGGCCCCGGGCAAA<br>GGTCTCGAGTGGGTTTCCGGTATCTCTGGTTCTGGTTCTTCTA<br>CCTACTATGCGGATAGCGTGAAAGGCCGCTTTACCATCAGCCG<br>CGATAATTCGAAAAACACCCTGTATCTGCAAATGAACAGCCTG<br>CGTGCGGAAGATACGGCCGTGTATTATTGCGCGCGTGAACTGT<br>CTTACCTGTACTCTGGTTACTACTTCGATTACTGGGGCCAAGG<br>CACCCTGGTGACTGTTAGCTCA |
| Heavy Chain | 11 | QVQLLESGGGLVQPGGSLRLSCAASGFTFSTAAMSWVRQAPGK<br>GLEWVSGISGSGSSTYYADSVKGRFTISRDNSKNTLYLQMNSL<br>RAEDTAVYYCARELSYLYSGYYFDYWGQGTLVTVSSASTKGPS<br>VFPLAPSSKSTSGGTAALGCLVKDYFPEPVTVSWNSGALTSGV<br>HTFPAVLQSSGLYSLSSVVTVPSSSLGTQTYICNVNHKPSNTK<br>VDKRVEPKSCDKTHTCPPCPAPEAAGGPSVFLFPPKPKDTLMI<br>SRTPEVTCVVVDVSHEDPEVKFNWYVDGVEVHNAKTKPREEQY<br>NSTYRVVSVLTVLHQDWLNGKEYKCKVSNKALPAPIEKTISKA<br>KGQPREPQVYTLPPSREEMTKNQVSLTCLVKGFYPSDIAVEWE<br>SNGQPENNYKTTPPVLDSDGSFFLYSKLTVDKSRWQQGNVFSC<br>SVMHEALHNHYTQKSLSLSPGK |
| DNA encoding Heavy Chain | 12 | CAGGTGCAATTGCTGGAAAGCGGCGGTGGCCTGGTGCAGCCGG<br>GTGGCAGCCTGCGTCTGAGCTGCGCGGCGTCCGGATTCACCTT<br>TTCTACTGCTGCTATGTCTTGGGTGCGCCAGGCCCCGGGCAAA<br>GGTCTCGAGTGGGTTTCCGGTATCTCTGGTTCTGGTTCTTCTA<br>CCTACTATGCGGATAGCGTGAAAGGCCGCTTTACCATCAGCCG<br>CGATAATTCGAAAAACACCCTGTATCTGCAAATGAACAGCCTG<br>CGTGCGGAAGATACGGCCGTGTATTATTGCGCGCGTGAACTGT<br>CTTACCTGTACTCTGGTTACTACTTCGATTACTGGGGCCAAGG<br>CACCCTGGTGACTGTTAGCTCAGCCTCCACCAAGGGTCCATCG<br>GTCTTCCCCCTGGCACCCTCCTCCAAGAGCACCTCTGGGGGCA<br>CAGCGGCCCTGGGCTGCCTGGTCAAGGACTACTTCCCCGAACC<br>GGTGACGGTGTCGTGGAACTCAGGCGCCCTGACCAGCGGCGTG<br>CACACCTTCCCGGCTGTCCTACAGTCCTCAGGACTCTACTCCC<br>TCAGCAGCGTGGTGACCGTGCCCTCCAGCAGCTTGGGCACCCA<br>GACCTACATCTGCAACGTGAATCACAAGCCCAGCAACACCAAG<br>GTGGACAAGAGAGTTGAGCCCAAATCTTGTGACAAAACTCACA<br>CATGCCCACCGTGCCCAGCACCTGAAGCAGCGGGGGGACCGTC<br>AGTCTTCCTCTTCCCCCCAAAACCCAAGGACACCCTCATGATC<br>TCCCGGACCCCTGAGGTCACATGCGTGGTGGTGGACGTGAGCC<br>ACGAAGACCCTGAGGTCAAGTTCAACTGGTACGTGGACGGCGT<br>GGAGGTGCATAATGCCAAGACAAAGCCGCGGGAGGAGCAGTAC<br>AACAGCACGTACCGGGTGGTCAGCGTCCTCACCGTCCTGCACC<br>AGGACTGGCTGAATGGCAAGGAGTACAAGTGCAAGGTCTCCAA<br>CAAAGCCCTCCCAGCCCCCATCGAGAAAACCATCTCCAAAGCC<br>AAAGGGCAGCCCCGAGAACCACAGGTGTACACCCTGCCCCCAT<br>CCCGGGAGGAGATGACCAAGAACCAGGTCAGCCTGACCTGCCT<br>GGTCAAAGGCTTCTATCCCAGCGACATCGCCGTGGAGTGGGAG<br>AGCAATGGGCAGCCGGAGAACAACTACAAGACCACGCCTCCCG<br>TGCTGGACTCCGACGGCTCCTTCTTCCTCTACAGCAAGCTCAC<br>CGTGGACAAGAGCAGGTGGCAGCAGGGGAACGTCTTCTCATGC<br>TCCGTGATGCATGAGGCTCTGCACAACCACTACACGCAGAAGA<br>GCCTCTCCCTGTCTCCGGGTAAA |
| LCDR1 (Kabat) | 13 | SGSSSNIGSNDVS |
| LCDR2 (Kabat) | 14 | KNYNRPS |
| LCDR3 (Kabat) | 15 | SAWDQRQFDVV |
| LCDR1 (Chothia) | 16 | SSSNIGSND |
| LCDR2 (Chothia) | 17 | KNY |

TABLE 1-continued

Examples of FXIa Antibodies,
Fabs and FXIa Proteins.

| Sequence Description | Sequence Identifier (SEQ ID NO:) | Amino acid or polynucleotide sequence |
|---|---|---|
| LCDR3 (Chothia) | 18 | WDQRQFDV |
| LCDR1 (IMGT) | 47 | SSNIGSND |
| LCDR2 (IMGT) | 37 | KNY |
| LCDR3 (IMGT) | 15 | SAWDQRQFDVV |
| LCDR1 (Combined) | 33 | SGSSSNIGSNDVS |
| LCDR2 (Combined) | 14 | KNYNRPS |
| LCDR3 (Combined) | 15 | SAWDQRQFDVV |
| VL | 19 | DIVLTQPPSVSGAPGQRVTISCSGSSSNIGSNDVSWYQQLPGT APKLLIYKNYNRPSGVPDRFSGSKSGTSASLAITGLQAEDEAD YYCSAWDQRQFDVVFGGGTKLTVL |
| DNA encoding VL | 20 | GATATCGTGCTGACCCAGCCGCCGAGCGTGAGCGGTGCACCGG GCCAGCGCGTGACCATTAGCTGTAGCGGCAGCAGCAGCAACAT TGGTTCTAACGACGTGTCTTGGTACCAGCAGCTGCCGGGCACG GCGCCGAAACTGCTGATCTACAAAAACTACAACCGCCCGAGCG GCGTGCCGGATCGCTTTAGCGGATCCAAAAGCGGCACCAGCGC CAGCCTGGCGATTACCGGCCTGCAAGCAGAAGACGAAGCGGAT TATTACTGCTCTGCTTGGGACCAGCGTCAGTTCGACGTTGTGT TTGGCGGCGGCACGAAGTTAACCGTCCTA |
| Light Chain | 21 | DIVLTQPPSVSGAPGQRVTISCSGSSSNIGSNDVSWYQQLPGT APKLLIYKNYNRPSGVPDRFSGSKSGTSASLAITGLQAEDEAD YYCSAWDQRQFDVVFGGGTKLTVLGQPKAAPSVTLFPPSSEEL QANKATLVCLISDFYPGAVTVAWKADSSPVKAGVETTTPSKQS NNKYAASSYLSLTPEQWKSHRSYSCQVTHEGSTVEKTVAPTEC S |
| DNA encoding Light Chain | 22 | GATATCGTGCTGACCCAGCCGCCGAGCGTGAGCGGTGCACCGG GCCAGCGCGTGACCATTAGCTGTAGCGGCAGCAGCAGCAACAT TGGTTCTAACGACGTGTCTTGGTACCAGCAGCTGCCGGGCACG GCGCCGAAACTGCTGATCTACAAAAACTACAACCGCCCGAGCG GCGTGCCGGATCGCTTTAGCGGATCCAAAAGCGGCACCAGCGC CAGCCTGGCGATTACCGGCCTGCAAGCAGAAGACGAAGCGGAT TATTACTGCTCTGCTTGGGACCAGCGTCAGTTCGACGTTGTGT TTGGCGGCGGCACGAAGTTAACCGTCCTAGGTCAGCCCAAGGC TGCCCCCTCGGTCACTCTGTTCCCGCCCTCCTCTGAGGAGCTT CAAGCCAACAAGGCCACACTGGTGTGTCTCATAAGTGACTTCT ACCCGGGAGCCGTGACAGTGGCCTGGAAGGCAGATAGCAGCCC CGTCAAGGCGGGAGTGGAGACCACCACACCCTCCAAACAAAGC AACAACAAGTACGCGGCCAGCAGCTATCTGAGCCTGACGCCTG AGCAGTGGAAGTCCCACAGAAGCTACAGCTGCCAGGTCACGCA TGAAGGGAGCACCGTGGAGAAGACAGTGGCCCCTACAGAATGT TCA |
| NOV1401 | | |
| HCDR1 (Kabat) | 23 | TAAMS |
| HCDR2 (Kabat) | 24 | GISGSGSSTYYADSVKG |
| HCDR3 (Kabat) | 25 | ELSYLYSGYYFDY |
| HCDR1 (Chothia) | 26 | GFTFSTA |
| HCDR2 (Chothia) | 27 | SGSGSS |
| HCDR3 (Chothia) | 28 | ELSYLYSGYYFDY |
| HCDR1 (IMGT) | 43 | GFTFSTAA |
| HCDR2 (IMGT) | 44 | ISGSGSST |
| HCDR3 (IMGT) | 45 | ARELSYLYSGYYFDY |
| HCDR1 (Combined) | 46 | GFTFSTAAMS |

TABLE 1-continued

Examples of FXIa Antibodies, Fabs and FXIa Proteins.

| Sequence Description | Sequence Identifier (SEQ ID NO:) | Amino acid or polynucleotide sequence |
|---|---|---|
| HCDR2 (Combined) | 4 | GISGSGSSTYYADSVKG |
| HCDR3 (Combined) | 5 | ELSYLYSGYYFDY |
| VH | 29 | QVQLLESGGGLVQPGGSLRLSCAASGFTFSTAAMSWVRQAPGK GLEWVSGISGSGSSTYYADSVKGRFTISRDNSKNTLYLQMNSL RAEDTAVYYCARELSYLYSGYYFDYWGQGTLVTVSS |
| DNA encoding VH | 30 | CAGGTGCAGCTGCTGGAATCAGGCGGCGGACTGGTGCAGCCTG GCGGTAGCCTGAGACTGAGCTGCGCTGCTAGTGGCTTCACCTT TAGCACCGCCGCTATGAGCTGGGTTCGACAGGCCCCAGGGAAA GGCCTCGAGTGGGTCTCAGGGATTAGCGGTAGCGGCTCTAGCA CCTACTACGCCGATAGCGTGAAGGGCCGGTTCACTATCTCTAG GGATAACTCTAAGAACACCCTGTACCTGCAGATGAATAGCCTG AGAGCCGAGGACACCGCCGTCTACTACTGCGCTAGAGAGCTGA GCTACCTGTATAGCGGCTACTACTTCGACTACTGGGGTCAAGG CACCCTGGTCACCGTGTCTAGC |
| Heavy Chain | 31 | QVQLLESGGGLVQPGGSLRLSCAASGFTFSTAAMSWVRQAPGK GLEWVSGISGSGSSTYYADSVKGRFTISRDNSKNTLYLQMNSL RAEDTAVYYCARELSYLYSGYYFDYWGQGTLVTVSSASTKGPS VFPLAPSSKSTSGGTAALGCLVKDYFPEPVTVSWNSGALTSGV HTFPAVLQSSGLYSLSSVVTVPSSSLGTQTYICNVNHKPSNTK VDKRVEPKSCDKTHTCPPCPAPELLGGPSVFLFPPKPKDTLMI SRTPEVTCVVVAVSHEDPEVKFNWYVDGVEVHNAKTKPREEQY NSTYRVVSVLTVLHQDWLNGKEYKCKVSNKALAAPIEKTISKA KGQPREPQVYTLPPSREEMTKNQVSLTCLVKGFYPSDIAVEWE SNGQPENNYKTTPPVLDSDGSFFLYSKLTVDKSRWQQGNVFSC SVMHEALHNHYTQKSLSLSPGK |
| DNA encoding Heavy Chain | 32 | CAGGTGCAGCTGCTGGAATCAGGCGGCGGACTGGTGCAGCCTG GCGGTAGCCTGAGACTGAGCTGCGCTGCTAGTGGCTTCACCTT TAGCACCGCCGCTATGAGCTGGGTTCGACAGGCCCCAGGGAAA GGCCTCGAGTGGGTCTCAGGGATTAGCGGTAGCGGCTCTAGCA CCTACTACGCCGATAGCGTGAAGGGCCGGTTCACTATCTCTAG GGATAACTCTAAGAACACCCTGTACCTGCAGATGAATAGCCTG AGAGCCGAGGACACCGCCGTCTACTACTGCGCTAGAGAGCTGA GCTACCTGTATAGCGGCTACTACTTCGACTACTGGGGTCAAGG CACCCTGGTCACCGTGTCTAGCGCTAGCACTAAGGGCCCCTCC GTGTTCCCTCTGGCCCCTTCCAGCAAGTCTACCTCCGGCGGCA CAGCTGCTCTGGGCTGCCTGGTCAAGGACTACTTCCCTGAGCC TGTGACAGTGTCCTGGAACTCTGGCGCCCTGACCTCTGGCGTG CACACCTTCCCTGCCGTGCTGCAGTCCTCCGGCCTGTACTCCC TGTCCTCCGTGGTCACAGTGCCTTCAAGCAGCCTGGGCACCCA GACCTATATCTGCAACGTGAACCACAAGCCTTCCAACACCAAG GTGGACAAGCGGGTGGAGCCTAAGTCCTGCGACAAGACCCACA CCTGTCCTCCCTGCCCTGCTCCTGAACTGCTGGGCGGCCCTTC TGTGTTCCTGTTCCCTCCAAAGCCCAAGGACACCCTGATGATC TCCCGGACCCCTGAAGTGACCTGCGTGGTGGTGGCCGTGTCCC ACGAGGATCCTGAAGTGAAGTTCAATTGGTACGTGGACGGCGT GGAGGTGCACAACGCCAAGACCAAGCCTCGGGAGGAACAGTAC AACTCCACCTACCGGGTGGTGTCCGTGCTGACCGTGCTGCACC AGGACTGGCTGAACGGCAAAGAGTACAAGTGCAAAGTCTCCAA CAAGGCCCTGGCCGCCCCTATCGAAAAGACAATCTCCAAGGCC AAGGGCCAGCCTAGGGAACCCCAGGTGTACACCCTGCCACCCA GCCGGGAGGAAATGACCAAGAACCAGGTGTCCCTGACCTGTCT GGTCAAGGGCTTCTACCCTTCCGATATCGCCGTGGAGTGGGAG TCTAACGGCCAGCCTGAGAACAACTACAAGACCACCCCTCCTG TGCTGGACTCCGACGGCTCCTTCTTCCTGTACTCCAAACTGAC CGTGGACAAGTCCCGGTGGCAGCAGGGCAACGTGTTCTCCTGC TCCGTGATGCACGAGGCCCTGCACAACCACTACACCCAGAAGT CCCTGTCCCTGTCTCCCGGCAAG |
| LCDR1 (Kabat) | 33 | SGSSSNIGSNDVS |
| LCDR2 (Kabat) | 34 | KNYNRPS |
| LCDR3 (Kabat) | 35 | SAWDQRQFDVV |
| LCDR1 (Chothia) | 36 | SSSNIGSND |

TABLE 1-continued

Examples of FXIa Antibodies, Fabs and FXIa Proteins.

| Sequence Description | Sequence Identifier (SEQ ID NO:) | Amino acid or polynucleotide sequence |
|---|---|---|
| LCDR2 (Chothia) | 37 | KNY |
| LCDR3 (Chothia) | 38 | WDQRQFDV |
| LCDR1 (IMGT) | 47 | SSNIGSND |
| LCDR2 (IMGT) | 37 | KNY |
| LCDR3 (IMGT) | 15 | SAWDQRQFDVV |
| LCDR1 (Combined) | 33 | SGSSSNIGSNDVS |
| LCDR2 (Combined) | 14 | KNYNRPS |
| LCDR3 (Combined) | 15 | SAWDQRQFDVV |
| VL | 39 | QSVLTQPPSASGTPGQRVTISCSGSSSNIGSNDVSWYQQLPGT APKLLIYKNYNRPSGVPDRFSGSKSGTSASLAISGLQSEDEAD YYCSAWDQRQFDVVFGGGTKLTVL |
| DNA encoding VL | 40 | CAGTCAGTCCTGACTCAGCCCCCTAGCGCTAGTGGCACCCCTG GTCAAAGAGTGACTATTAGCTGTAGCGGCTCTAGCTCTAATAT CGGCTCTAACGACGTCAGCTGGTATCAGCAGCTGCCCGGCACC GCCCCTAAGCTGCTGATCTATAAGAACTATAATAGGCCTAGCG GCGTGCCCGATAGGTTTAGCGGATCTAAATCAGGGACTTCTGC TAGTCTGGCTATTAGCGGCCTGCAGTCAGAGGACGAGGCCGAC TACTACTGTAGCGCCTGGGATCAGCGTCAGTTCGACGTGGTGT TCGGCGGAGGCACTAAGCTGACCGTGCTG |
| Light Chain | 41 | QSVLTQPPSASGTPGQRVTISCSGSSSNIGSNDVSWYQQLPGT APKLLIYKNYNRPSGVPDRFSGSKSGTSASLAISGLQSEDEAD YYCSAWDQRQFDVVFGGGTKLTVLGQPKAAPSVTLFPPSSEEL QANKATLVCLISDFYPGAVTVAWKADSSPVKAGVETTTPSKQS NNKYAASSYLSLTPEQWKSHRSYSCQVTHEGSTVEKTVAPTEC S |
| DNA encoding Light Chain | 42 | CAGTCAGTCCTGACTCAGCCCCCTAGCGCTAGTGGCACCCCTG GTCAAAGAGTGACTATTAGCTGTAGCGGCTCTAGCTCTAATAT CGGCTCTAACGACGTCAGCTGGTATCAGCAGCTGCCCGGCACC GCCCCTAAGCTGCTGATCTATAAGAACTATAATAGGCCTAGCG GCGTGCCCGATAGGTTTAGCGGATCTAAATCAGGGACTTCTGC TAGTCTGGCTATTAGCGGCCTGCAGTCAGAGGACGAGGCCGAC TACTACTGTAGCGCCTGGGATCAGCGTCAGTTCGACGTGGTGT TCGGCGGAGGCACTAAGCTGACCGTGCTGGGTCAACCTAAGGC TGCCCCCAGCGTGACCCTGTTCCCCCCCAGCAGCGAGGAGCTG CAGGCCAACAAGGCCACCCTGGTGTGCCTGATCAGCGACTTCT ACCCAGGCGCCGTGACCGTGGCCTGGAAGGCCGACAGCAGCCC CGTGAAGGCCGGCGTGGAGACCACCACCCCCAGCAAGCAGAGC AACAACAAGTACGCCGCCAGCAGCTACCTGAGCCTGACCCCCG AGCAGTGGAAGAGCCACAGGTCCTACAGCTGCCAGGTGACCCA CGAGGGCAGCACCGTGGAAAAGACCGTGGCCCCAACCGAGTGC AGC |

Other antibodies of the invention include those where the amino acids or nucleic acids encoding the amino acids have been mutated, yet have at least 60, 65, 70, 75, 80, 85, 90, or 95 percent identity to the sequences described in Table 1. Some embodiments include mutant amino acid sequences wherein no more than 1, 2, 3, 4 or 5 amino acids have been mutated in the variable regions when compared with the variable regions depicted in the sequence described in Table 1, while retaining substantially the same antigen binding activity.

Since each of these antibodies can bind to FXI and/or FXIa, the VH, VL, full length light chain, and full length heavy chain sequences (amino acid sequences and the nucleotide sequences encoding the amino acid sequences) can be "mixed and matched" to create other FXI and/or FXIa-binding antibodies of the invention. Such "mixed and matched" FXI and/or FXIa-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence.

Accordingly, in one aspect, the invention provides an isolated antibody or antigen binding region thereof having: a heavy chain variable domain comprising an amino acid sequence selected from the group consisting of SEQ ID NOs: 9 and 29, and a light chain variable domain comprising an amino acid sequence selected from the group consisting of SEQ ID NOs: 19 and 39, wherein the antibody specifically binds to FXI and/or FXIa (e.g., human, rabbit, and cynomolgus monkey FXIa).

More specifically, in certain aspects, the invention provides an isolated antibody or antigen binding region thereof having a heavy chain variable domain and a light chain variable domain comprising amino acid sequences selected from SEQ ID NOs: 9 and 29; or 19 and 39, respectively.

In a specific embodiment, an antibody or antigen binding fragment thereof provided herein which specifically binds to human FXI and/or FXIa, comprises a heavy chain variable region comprising the amino acid sequence of SEQ ID NO: 9, and a light chain variable region comprising the amino acid sequence of SEQ ID NO: 19.

In a specific embodiment, an antibody or antigen binding fragment thereof provided herein which specifically binds to human FXI and/or FXIa, comprises a heavy chain variable region comprising the amino acid sequence of SEQ ID NO: 29, and a light chain variable region comprising the amino acid sequence of SEQ ID NO: 39.

In another aspect, the invention provides (i) an isolated antibody having: a full length heavy chain comprising an amino acid sequence that has been optimized for expression in a mammalian cell selected from the group consisting of SEQ ID NOs: 11 or 31, and a full length light chain comprising an amino acid sequence that has been optimized for expression in a mammalian cell selected from the group consisting of SEQ ID NOs: 21 or 41; or (ii) a functional protein comprising an antigen binding portion thereof. More specifically, in certain aspects, the invention provides an isolated antibody or antigen binding region thereof having a heavy chain and a light chain comprising amino acid sequences selected from SEQ ID NOs: 11 and 31; or 19 and 39, respectively.

In a specific embodiment, an antibody or antigen binding fragment thereof provided herein which specifically binds to human FXI and/or FXIa, comprises a heavy chain comprising the amino acid sequence of SEQ ID NO: 11, and a light chain comprising the amino acid sequence of SEQ ID NO: 21.

In a specific embodiment, an antibody or antigen binding fragment thereof provided herein which specifically binds to human FXI and/or FXIa, comprises a heavy chain variable region comprising the amino acid sequence of SEQ ID NO: 31, and a light chain variable region comprising the amino acid sequence of SEQ ID NO: 41.

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme), Lefranc et al., (2003) Dev. Comp. Immunol., 27, 55-77 ("IMGT" numbering scheme), or the "Combined" system.

For example, under Kabat, the CDR amino acid residues of antibody NOV1090 in the heavy chain variable domain (VH) are numbered 31-35 (HCDR1), 50-66 (HCDR2), and 99-111 (HCDR3); and the CDR amino acid residues in the light chain variable domain (VL) are numbered 22-35 (LCDR1), 51-57 (LCDR2), and 90-100 (LCDR3). Under Chothia the CDR amino acids in the VH are numbered 26-32 (HCDR1), 52-57 (HCDR2), and 99-111 (HCDR3); and the amino acid residues in VL are numbered 25-33 (LCDR1), 51-53 (LCDR2), and 92-99 (LCDR3). By combining the CDR definitions of both Kabat and Chothia, the CDRs consist of amino acid residues 26-35 (HCDR1), 50-66 (HCDR2), and 99-111 (HCDR3) in human VH and amino acid residues 22-35 (LCDR1), 51-57 (LCDR2), and 90-100 (LCDR3) in human VL. By combining the CDR definitions of both Kabat and Chothia, the "Combined" CDRs consist of amino acid residues 26-35 (HCDR1), 50-66 (HCDR2), and 99-108 (HCDR3) in human VH and amino acid residues 24-38 (LCDR1), 54-60 (LCDR2), and 93-101 (LCDR3) in human VL. As another example, under IMGT, the CDR amino acid residues in the heavy chain variable domain (VH) are numbered 26-33 (HCDR1), 51-58 (HCDR2), and 97-108 (HCDR3); and the CDR amino acid residues in the light chain variable domain (VL) are numbered 27-36 (LCDR1), 54-56 (LCDR2), and 93-101 (LCDR3). Table 1 provides exemplary Kabat, Chothia, Combined, and IMGT HCDR1, HCDR2, HCDR3, LCDR1, LCDR2, and LCDR3 for anti-FXI/FXIa antibodies, e.g., NOV1090 and NOV1401. In another aspect, the present invention provides FXIa binding antibodies that comprise the heavy chain and light chain CDR1s, CDR2s, and CDR3s as described in Table 1, or combinations thereof. The amino acid sequences of the VH CDR1s of the antibodies are shown in SEQ ID NOs: 3 and 23. The amino acid sequences of the VH CDR2s of the antibodies and are shown in SEQ ID NOs: 4 and 24. The amino acid sequences of the VH CDR3s of the antibodies are shown in SEQ ID NOs: 5 and 25. The amino acid sequences of the VL CDR1s of the antibodies are shown in SEQ ID NOs: 13 and 33. The amino acid sequences of the VL CDR2s of the antibodies are shown in SEQ ID NOs: 14 and 34. The amino acid sequences of the VL CDR3s of the antibodies are shown in SEQ ID NOs: 15 and 35. These CDR regions are delineated using the Kabat system.

Alternatively, as defined using the Chothia system (Al-Lazikani et al., (1997) JMB 273,927-948), the amino acid sequences of the VH CDR1s of the antibodies are shown in SEQ ID NOs: 6 and 26. The amino acid sequences of the VH CDR2s of the antibodies and are shown in SEQ ID NOs: 7 and 27. The amino acid sequences of the VH CDR3s of the antibodies are shown in SEQ ID NOs: 8 and 28. The amino acid sequences of the VL CDR1s of the antibodies are shown in SEQ ID NOs: 16 and 36. The amino acid sequences of the VL CDR2s of the antibodies are shown in SEQ ID NOs: 17 and 37. The amino acid sequences of the VL CDR3s of the antibodies are shown in SEQ ID NOs: 18 and 38.

Alternatively, as defined using the Combined system, the amino acid sequences of the VH CDR1 of the antibodies are shown in SEQ ID NO: 46. The amino acid sequences of the VH CDR2 of the antibodies and are shown in SEQ ID NO: 4. The amino acid sequences of the VH CDR3 of the antibodies are shown in SEQ ID NO: 5. The amino acid sequences of the VL CDR1 of the antibodies are shown in SEQ ID NO: 33. The amino acid sequences of the VL CDR2 of the antibodies are shown in SEQ ID NO: 14. The amino acid sequences of the VL CDR3 of the antibodies are shown in SEQ ID NO: 15.

Alternatively, as defined using the IMGT numbering scheme, the amino acid sequences of the VH CDR1 of the antibodies are shown in SEQ ID NO: 43. The amino acid sequences of the VH CDR2 of the antibodies and are shown in SEQ ID NO: 44. The amino acid sequences of the VH CDR3 of the antibodies are shown in SEQ ID NO: 45. The amino acid sequences of the VL CDR1 of the antibodies are shown in SEQ ID NO: 47. The amino acid sequences of the VL CDR2 of the antibodies are shown in SEQ ID NO: 37. The amino acid sequences of the VL CDR3 of the antibodies are shown in SEQ ID NO: 15.

Given that each of these antibodies can bind to FXI and/or FXIa and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and matched, although each antibody preferably contains a VH CDR1, 2 and 3 and a VL CDR1, 2 and 3 to create other FXI and/or FXIa binding molecules of the invention. Such "mixed and matched" FXI and/or FXIa binding antibodies can be tested using the binding assays known in the art and those described in the Examples (e.g., ELISAs, SET, BIACORE™ assays). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present invention. In addition to the foregoing, in one embodiment, the antigen binding fragments of the antibodies described herein can comprise a VH CDR1, 2, and 3, or a VL CDR 1, 2, and 3, wherein the fragment binds to FXI and/or FXIa as a single variable domain.

In certain embodiments of the invention, the antibodies or antigen binding fragments thereof may have the heavy and light chain sequences of the Fabs described in Table 1. More specifically, the antibody or antigen binding fragments thereof may have the heavy and light sequence of NOV1090 and NOV1401.

In other embodiments of the invention the antibody or antigen binding fragment in that specifically binds FXI and/or FXIa comprises a heavy chain variable region CDR1, a heavy chain variable region CDR2, a heavy chain variable region CDR3, a light chain variable region CDR1, a light chain variable region CDR2, and a light chain variable region CDR3 as defined by Kabat and described in Table 1. In still other embodiments of the invention the antibody or antigen binding fragment in that specifically binds FXI and/or FXIa comprises a heavy chain variable region CDR1, a heavy chain variable region CDR2, a heavy chain variable region CDR3, a light chain variable region CDR1, a light chain variable region CDR2, and a light chain variable region CDR3 as defined by Chothia and described in Table 1. In other embodiments, the antibody or antigen binding fragment in that specifically binds FXI and/or FXIa comprises a heavy chain variable region CDR1, a heavy chain variable region CDR2, a heavy chain variable region CDR3, a light chain variable region CDR1, a light chain variable region CDR2, and a light chain variable region CDR3 as defined by the Combined system and described in Table 1. In still other embodiments of the invention the antibody or antigen binding fragment in that specifically binds FXI and/or FXIa comprises a heavy chain variable region CDR1, a heavy chain variable region CDR2, a heavy chain variable region CDR3, a light chain variable region CDR1, a light chain variable region CDR2, and a light chain variable region CDR3 as defined by IMGT and described in Table 1.

In a specific embodiment, the invention includes an antibody that specifically binds to FXI and/or FXIa comprising a heavy chain variable region CDR1 of SEQ ID NO: 3; a heavy chain variable region CDR2 of SEQ ID NO: 4; a heavy chain variable region CDR3 of SEQ ID NO: 5; a light chain variable region CDR1 of SEQ ID NO: 13; a light chain variable region CDR2 of SEQ ID NO: 14; and a light chain variable region CDR3 of SEQ ID NO: 15.

In a specific embodiment, the invention includes an antibody that specifically binds to FXI and/or FXIa comprising a heavy chain variable region CDR1 of SEQ ID NO: 23; a heavy chain variable region CDR2 of SEQ ID NO: 24; a heavy chain variable region CDR3 of SEQ ID NO: 25; a light chain variable region CDR1 of SEQ ID NO: 33; a light chain variable region CDR2 of SEQ ID NO: 34; and a light chain variable region CDR3 of SEQ ID NO: 35.

In a specific embodiment, the invention includes an antibody that specifically binds to FXI and/or FXIa comprising a heavy chain variable region CDR1 of SEQ ID NO: 6; a heavy chain variable region CDR2 of SEQ ID NO: 7; a heavy chain variable region CDR3 of SEQ ID NO: 8; a light chain variable region CDR1 of SEQ ID NO: 16; a light chain variable region CDR2 of SEQ ID NO: 17; and a light chain variable region CDR3 of SEQ ID NO: 18.

In a specific embodiment, the invention includes an antibody that specifically binds to FXI and/or FXIa comprising a heavy chain variable region CDR1 of SEQ ID NO: 26; a heavy chain variable region CDR2 of SEQ ID NO: 27; a heavy chain variable region CDR3 of SEQ ID NO: 28; a light chain variable region CDR1 of SEQ ID NO: 36; a light chain variable region CDR2 of SEQ ID NO: 37; and a light chain variable region CDR3 of SEQ ID NO: 38.

In a specific embodiment, provided herein is an antibody that specifically binds to FXI and/or FXIa comprising a heavy chain variable region CDR1 of SEQ ID NO: 43; a heavy chain variable region CDR2 of SEQ ID NO: 44; a heavy chain variable region CDR3 of SEQ ID NO: 45; a light chain variable region CDR1 of SEQ ID NO: 47; a light chain variable region CDR2 of SEQ ID NO: 37 and a light chain variable region CDR3 of SEQ ID NO: 15.

In a specific embodiment, provided herein is an antibody that specifically binds to FXI and/or FXIa comprising a heavy chain variable region CDR1 of SEQ ID NO: 46; a heavy chain variable region CDR2 of SEQ ID NO: 4; a heavy chain variable region CDR3 of SEQ ID NO: 5; a light chain variable region CDR1 of SEQ ID NO: 33; a light chain variable region CDR2 of SEQ ID NO: 14 and a light chain variable region CDR3 of SEQ ID NO: 15.

In certain embodiments, the invention includes antibodies or antigen binding fragments that specifically bind to FXI and/or FXIa as described in Table 1. In a preferred embodiment, the antibody, or antigen binding fragment, that binds FXI and/or FXIa is NOV1090 and NOV1401.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody.

A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene.

Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene. Examples of human germline immunoglobulin genes include, but are not limited to the variable domain germline fragments described below, as well as DP47 and DPK9.

Homologous Antibodies

In yet another embodiment, the present invention provides an antibody, or an antigen binding fragment thereof, comprising amino acid sequences that are homologous to the sequences described in Table 1 (e.g., SEQ ID NOs: 29, 31, 39, or 41), and the antibody binds to an FXI and/or FXIa protein (e.g., human, rabbit, and cynomolgus monkey FXIa), and retains the desired functional properties of those antibodies described in Table 1 such as NOV1090 and NOV1401. In specific aspects, such homologous antibodies retain the CDR amino acid sequences described in Table 1 (e.g., Kabat CDRs, Chothia CDRs, IMGT CDRs, or Combined CDRs).

For example, the invention provides an isolated antibody, or a functional antigen binding fragment thereof, comprising a heavy chain variable domain and a light chain variable domain, wherein the heavy chain variable domain comprises an amino acid sequence that is at least 80%, at least 90%, or at least 95% identical to an amino acid sequence selected from the group consisting of SEQ ID NOs: 9 and 29; the light chain variable domain comprises an amino acid sequence that is at least 80%, at least 90%, or at least 95% identical to an amino acid sequence selected from the group consisting of SEQ ID NOs: 19 and 39; and the antibody specifically binds to FXI and/or FXIa (e.g., human, rabbit, and cynomolgus monkey FXIa). In one embodiment, an isolated antibody, or a functional antigen binding fragment thereof, comprises a heavy chain variable domain and a light chain variable domain, wherein the heavy chain variable domain comprises an amino acid sequence that is at least 80%, at least 90%, or at least 95% identical to the amino acid sequence of SEQ ID NO: 9; the light chain variable domain comprises an amino acid sequence that is at least 80%, at least 90%, or at least 95% identical to the amino acid sequence of SEQ ID NO: 19; and the antibody specifically binds to FXI and/or FXIa (e.g., human, rabbit, and cynomolgus monkey FXIa). In one embodiment, an isolated antibody, or a functional antigen binding fragment thereof, comprises a heavy chain variable domain and a light chain variable domain, wherein the heavy chain variable domain comprises an amino acid sequence that is at least 80%, at least 90%, or at least 95% identical to the amino acid sequence of SEQ ID NO: 29; the light chain variable domain comprises an amino acid sequence that is at least 80%, at least 90%, or at least 95% identical to the amino acid sequence of SEQ ID NO: 39; and the antibody specifically binds to FXI and/or FXIa (e.g., human, rabbit, and cynomolgus monkey FXIa). In certain aspects of the invention the heavy and light chain sequences further comprise HCDR1, HCDR2, HCDR3, LCDR1, LCDR2, and LCDR3 sequences as defined by Kabat, for example SEQ ID NOs: 3, 4, 5, 13, 14, and 15, respectively. In certain other aspects of the invention the heavy and light chain sequences further comprise HCDR1, HCDR2, HCDR3, LCDR1, LCDR2, and LCDR3 sequences as defined by Chothia, for example SEQ ID NOs: 6, 7, 8, 16, 17, and 18, respectively. In certain other aspects, the heavy and light chain sequences further comprise HCDR1, HCDR2, HCDR3, LCDR1, LCDR2, and LCDR3 sequences as defined by the Combined system, for example SEQ ID NOs: 46, 4, 5, 33, 14, and 15, respectively. In certain other aspects, the heavy and light chain sequences further comprise HCDR1, HCDR2, HCDR3, LCDR1, LCDR2, and LCDR3 sequences as defined by IMGT, for example SEQ ID NOs: 43, 44, 45, 47, 37, and 15, respectively.

In other embodiments, the VH and/or VL amino acid sequences may be 50%, 60%, 70%, 80%, 90%, 95%, 96%, 97%, 98% or 99% identical to the sequences set forth in Table 1. In other embodiments, the VH and/or VL amino acid sequences may be identical except for an amino acid substitution in no more than 1,2,3,4 or 5 amino acid positions. An antibody having VH and VL regions having high (i. e., 80% or greater) identity to the VH and VL regions of those described in Table 1 can be obtained by mutagenesis (e.g., site-directed or PCR-mediated mutagenesis) of nucleic acid molecules encoding SEQ ID NOs: 10 or 30 and SEQ ID NOs: 20 and 40, respectively, followed by testing of the encoded altered antibody for retained function using the functional assays described herein.

In other embodiments, the full length heavy chain and/or full length light chain amino acid sequences may be 50° 60%, 70%, 80%, 90%, 95%, 96%, 97%, 98% or 99% identical to the sequences set forth in Table 1 (e.g., SEQ ID NOs: 11 and/or 21, or 31 and/or 41). An antibody having a full length heavy chain and full length light chain having high (i.e., 80% or greater) identity to the full length heavy chains of any of SEQ ID NOs: 11 or 31, and full length light chains of any of SEQ ID NOs: 21 or 41, can be obtained by mutagenesis (e.g., site-directed or PCR-mediated mutagenesis) of nucleic acid molecules encoding such polypeptides, followed by testing of the encoded altered antibody for retained function using the functional assays described herein.

In one aspect, provided herein is an isolated antibody, or a functional antigen binding fragment thereof, comprising a heavy chain and a light chain, wherein the heavy chain comprises an amino acid sequence that is at least 80%, at least 90%, or at least 95% identical to an amino acid sequence selected from the group consisting of SEQ ID NOs: 11 and 31; the light chain comprises an amino acid sequence that is at least 80%, at least 90%, or at least 95% identical to an amino acid sequence selected from the group consisting of SEQ ID NOs: 21 and 41; and the antibody specifically binds to FXI and/or FXIa (e.g., human, rabbit, and cynomolgus monkey FXIa). In one embodiment, an isolated antibody, or a functional antigen binding fragment thereof, comprises a heavy chain and a light chain, wherein the heavy chain comprises an amino acid sequence that is at least 80%, at least 90%, or at least 95% identical to the amino acid sequence of SEQ ID NO: 11; the light chain comprises an amino acid sequence that is at least 80%, at least 90%, or at least 95% identical to the amino acid sequence of SEQ ID NO: 21; and the antibody specifically binds to FXI and/or FXIa (e.g., human, rabbit, and cynomolgus monkey FXIa). In one embodiment, an isolated antibody, or a functional antigen binding fragment thereof, comprises a heavy chain and a light chain, wherein the heavy chain comprises an amino acid sequence that is at least 80%, at least 90%, or at least 95% identical to the amino acid sequence of SEQ ID NO: 31; the light chain comprises an amino acid sequence that is at least 80%, at least 90%, or at least 95% identical to the amino acid sequence of SEQ ID NO: 41; and the antibody specifically binds to FXI and/or FXIa (e.g., human, rabbit, and cynomolgus monkey FXIa). In certain aspects of the invention the heavy and light chain sequences further comprise HCDR1, HCDR2, HCDR3, LCDR1, LCDR2, and LCDR3 sequences as defined by Kabat, for example SEQ ID NOs: 3, 4, 5, 13, 14, and 15, respectively. In certain other aspects of the invention the heavy and light chain sequences further comprise HCDR1, HCDR2, HCDR3, LCDR1, LCDR2, and LCDR3 sequences as defined by Chothia, for example SEQ ID NOs: 6, 7, 8, 16, 17, and 18, respectively. In certain other aspects, the heavy and light chain sequences further comprise HCDR1, HCDR2, HCDR3, LCDR1, LCDR2, and LCDR3 sequences as defined by the Combined system, for example SEQ ID NOs: 46, 4, 5, 33, 14, and 15, respectively. In certain other aspects, the heavy and light chain sequences further comprise HCDR1, HCDR2, HCDR3, LCDR1, LCDR2, and LCDR3 sequences as defined by IMGT, for example SEQ ID NOs: 43, 44, 45, 47, 37, and 15, respectively.

In other embodiments, the full length heavy chain and/or full length light chain nucleotide sequences may be 60%, 70%, 80%, 90%, 95%, 98%, 97%, 98% or 99% identical to the sequences set forth in Table 1 (e.g., SEQ ID NOs: 12 and/or 22, or 32 and/or 42).

In other embodiments, the variable regions of heavy chain and/or the variable regions of light chain nucleotide sequences may be 60%, 70%, 80%, 90%, 95%, 98%, 97%, 98% or 99% identical to the sequences set forth in Table 1 (e.g., SEQ ID NOs: 10 and/or 20, or 30 and/or 40).

As used herein, the percent identity between the two sequences is a function of the number of identical positions shared by the sequences (i.e., % identity equals number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Additionally or alternatively, the protein sequences of the present invention can further be used as a "query sequence" to perform a search against public databases to, for example, identify related sequences. For example, such searches can be performed using the BLAST program (version 2.0) of Altschul, et al., 1990 J. Mol. Biol. 215:403-10.

Antibodies with Conservative Modifications

In certain embodiments, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the FXIa-binding antibodies of the invention.

Accordingly, the invention provides an isolated antibody, or an antigen binding fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 3 and 23, and conservative modifications thereof; the heavy chain variable region CDR2 amino acid sequences are selected from the group consisting of SEQ ID NOs: 4 and 24, and conservative modifications thereof; the heavy chain variable region CDR3 amino acid sequences are selected from the group consisting of SEQ ID NOs: 5 and 25, and conservative modifications thereof; the light chain variable regions CDR1 amino acid sequences are selected from the group consisting of SEQ ID NOs: 13 and 33, and conservative modifications thereof; the light chain variable regions CDR2 amino acid sequences are selected from the group consisting of SEQ ID NOs: 14 and 34, and conservative modifications thereof; the light chain variable regions of CDR3 amino acid sequences are selected from the group consisting of SEQ ID NOs: 15 and 35, and conservative modifications thereof; and the antibody or antigen binding fragments thereof specifically binds to FXIa.

In one aspect, provided herein is an isolated antibody, or an antigen binding fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of those described in Table 1, and conservative modifications thereof; the heavy chain variable region CDR2 amino acid sequences are selected from the group consisting of those described in Table 1, and conservative modifications thereof; the heavy chain variable region CDR3 amino acid sequences are selected from the group consisting of those described in Table 1, and conservative modifications thereof; the light chain variable regions CDR1 amino acid sequences are selected from the group consisting of those described in Table 1, and conservative modifications thereof; the light chain variable regions CDR2 amino acid sequences are selected from the group consisting of those described in Table 1, and conservative modifications thereof; the light chain variable regions of CDR3 amino acid sequences are selected from the group consisting of those described in Table 1, and conservative modifications thereof; and the antibody or antigen binding fragments thereof specifically binds to FXIa.

In other embodiments, the antibody of the invention is optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the FXIa binding antibodies of the invention. Accordingly, the invention provides an isolated antibody optimized for expression in a mammalian cell consisting of a full length heavy chain and a full length light chain wherein the full length heavy chain has amino acid sequences selected from the group of SEQ ID NOs: 11 or 31, and conservative modifications thereof; and the full length light chain has amino acid sequences selected from the group of SEQ ID NOs: 21 or 41, and conservative modifications thereof; and the antibody specifically binds to FXI and/or FXIa (e.g., human, rabbit, and cynomolgus monkey FXIa).

Antibodies that Bind to the Same Epitope

The present invention provides antibodies that bind to the same epitope as the FXI and/or FXIa binding antibodies described in Table 1. Additional antibodies can therefore be identified based on their ability to compete (e.g., to competitively inhibit the binding of, in a statistically significant manner, by binding to the same or overlapping epitope) with other antibodies of the invention in FXI and/or FXIa binding assays (such as those described in the Examples Section). The ability of a test antibody to inhibit the binding of antibodies of the present invention to a FXI and/or FXIa protein demonstrates that the test antibody can compete with that antibody for binding to FXI and/or FXIa; such an antibody may, according to non-limiting theory, bind to the same or a related (e.g., a structurally similar or spatially proximal) epitope on the FXI and/or FXIa protein as the antibody with which it competes. In a certain embodiment, the antibody that binds to the same epitope on FXI and/or FXIa as the antibodies of the present invention is a human monoclonal antibody. Such human monoclonal antibodies can be prepared and isolated as described herein.

As used herein, an antibody "competes" for binding when the competing antibody binds to the same FXI and/or FXIa epitope as an antibody or antigen binding fragment of the invention (e.g., NOV1401 or NOV1090) and inhibits FXI and/or FXIa binding of an antibody or antigen binding fragment of the invention by more than 50% (for example, 80%, 85%, 90%, 95%, 98% or 99%) in the presence of an equimolar concentration of competing antibody. This may be determined, for instance, in a competitive binding assay, by any of the methods well known to those of skill in the art.

As used herein, an antibody or antigen binding fragment thereof does not "compete" with an FXI and/or FXIa antibody or antigen binding fragment of the invention (e.g., NOV1401 or NOV1090) unless said competing antibody or antigen binding fragment thereof binds the same FXI and/or FXIa epitope, or an overlapping FXI and/or FXIa epitope, as an antibody or antigen binding fragment of the invention. As used herein, a competing antibody or antigen binding fragment thereof does not include one which (i) sterically blocks an antibody or antigen binding fragment of the invention from binding its target (e.g., if said competing antibody binds to a nearby, non-overlapping FXI and/or FXIa epitope and physically prevents an antibody or antigen binding fragment of the invention from binding its target); and/or (ii) binds to a different, non-overlapping FXI and/or FXIa epitope and induces a conformational change to the FXI and/or FXIa protein such that said protein can no longer be bound by an FXI and/or FXIa antibody or antigen binding fragment of the invention in a way that would occur absent said conformational change.

Engineered and Modified Antibodies

An antibody of the invention further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i. e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated antibody, or an antigen binding fragment thereof, comprising a heavy chain variable region comprising CDR1 sequences having an amino acid sequence selected from the group consisting of SEQ ID NOs: 3 and 23; CDR2 sequences having an amino acid sequence selected from the group consisting of SEQ ID NOs: 4 and 24; CDR3 sequences having an amino acid sequence selected from the group consisting of SEQ ID NOs: 5 and 25, respectively; and a light chain variable region having CDR1 sequences having an amino acid sequence selected from the group consisting of SEQ ID NOs: 13 and 33; CDR2 sequences having an amino acid sequence selected from the group consisting of SEQ ID NOs: 14 and 34; and CDR3 sequences consisting of an amino acid sequence selected from the group consisting of SEQ ID NOs: 15 and 35, respectively. Thus, such antibodies contain the VH and VL CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the world wide web at mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. Mol. Biol. 227:776-798; and Cox, J. P. L. et al., 1994 Eur. J Immunol. 24:827-836; the contents of each of which are expressly incorporated herein by reference.

An example of framework sequences for use in the antibodies of the invention are those that are structurally similar to the framework sequences used by selected antibodies of the invention, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al). Frameworks that can be utilized as scaffolds on which to build the antibodies and antigen binding fragments described herein include, but are not limited to VH1A, VH1B, VH3, Vk1, VI2, and Vk2. Additional frameworks are known in the art and may be found, for example, in the vBase data base on the world wide web at vbase.mrc-cpe.cam.ac.uk/index.php?&MMN_position=1:1.

Accordingly, an embodiment of the invention relates to isolated FXIa binding antibodies, or antigen binding fragments thereof, comprising a heavy chain variable region comprising an amino acid sequence selected from the group consisting of SEQ ID NOs: 9 and 29, or an amino acid sequence having one, two, three, four or five amino acid substitutions, deletions or additions in the framework region of such sequences, and further comprising a light chain variable region having an amino acid sequence selected from the group consisting of SEQ ID NOs: 19 or 39, or an amino acid sequence having one, two, three, four or five amino acid substitutions, deletions or additions in the framework region of such sequences.

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples Section. Conservative modifications (as discussed above) can be introduced. The mutations may be amino acid substitutions, additions or deletions. Moreover, typically no more than one, two, three, four or five residues within a CDR region are altered.

Accordingly, in another embodiment, the invention provides isolated FXIa-binding antibodies, or antigen binding fragments thereof, consisting of a heavy chain variable region having a VH CDR1 region consisting of an amino acid sequence selected from the group having SEQ ID NOs: 3 and 23 or an amino acid sequence having one, two, three, four or five amino acid substitutions, deletions or additions as compared to SEQ ID NOs: 3 and 23; a VH CDR2 region having an amino acid sequence selected from the group consisting of SEQ ID NOs: 4 and 24 or an amino acid sequence having one, two, three, four or five amino acid substitutions, deletions or additions as compared to SEQ ID NOs: 4 and 24; a VH CDR3 region having an amino acid sequence selected from the group consisting of SEQ ID NOs: 5 and 25, or an amino acid sequence having one, two, three, four or five amino acid substitutions, deletions or additions as compared to SEQ ID NOs: 5 and 25; a VL CDR1 region having an amino acid sequence selected from the group consisting of SEQ ID NOs: 13 and 33, or an amino acid sequence having one, two, three, four or five amino acid substitutions, deletions or additions as compared to SEQ ID NOs: 13 and 33; a VL CDR2 region having an amino acid sequence selected from the group consisting of SEQ ID NOs: 14 and 34, or an amino acid sequence having one, two, three, four or five amino acid substitutions, deletions or additions as compared to SEQ ID NOs: 14 and 34; and a VL CDR3 region having an amino acid sequence selected from the group consisting of SEQ ID NOs: 15 and 35, or an amino acid sequence having one, two, three, four or five amino acid substitutions, deletions or additions as compared to SEQ ID NOs: 15 and 35.

Accordingly, in another embodiment, the invention provides isolated FXIa-binding antibodies, or antigen binding fragments thereof, consisting of a heavy chain variable region having a VH CDR1 region consisting of an amino acid sequence selected from the group having SEQ ID NOs: 6 and 26 or an amino acid sequence having one, two, three, four or five amino acid substitutions, deletions or additions as compared to SEQ ID NOs: 6 and 26; a VH CDR2 region having an amino acid sequence selected from the group consisting of SEQ ID NOs: 7 and 27 or an amino acid sequence having one, two, three, four or five amino acid substitutions, deletions or additions as compared to SEQ ID NOs: 7 and 27; a VH CDR3 region having an amino acid sequence selected from the group consisting of SEQ ID NOs: 8 and 28, or an amino acid sequence having one, two, three, four or five amino acid substitutions, deletions or additions as compared to SEQ ID NOs: 8 and 28; a VL CDR1 region having an amino acid sequence selected from the group consisting of SEQ ID NOs: 16 and 36, or an amino acid sequence having one, two, three, four or five amino acid substitutions, deletions or additions as compared to SEQ ID NOs: 16 and 36; a VL CDR2 region having an amino acid sequence selected from the group consisting of SEQ ID NOs: 17 and 37, or an amino acid sequence having one, two, three, four or five amino acid substitutions, deletions or additions as compared to SEQ ID NOs: 17 and 37; and a VL CDR3 region having an amino acid sequence selected from the group consisting of SEQ ID NOs: 18 and 38, or an amino acid sequence having one, two, three, four or five amino acid substitutions, deletions or additions as compared to SEQ ID NOs: 18 and 38.

Grafting Antigen-binding Domains into Alternative Frameworks or Scaffolds

A wide variety of antibody/immunoglobulin frameworks or scaffolds can be employed so long as the resulting polypeptide includes at least one binding region which specifically binds to FXIa. Such frameworks or scaffolds include the 5 main idiotypes of human immunoglobulins, or fragments thereof, and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target FXI and/or FXIa protein. Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of *Pieris Brassicae* has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

The present invention provides fully human antibodies that specifically bind to a FXIa protein. Compared to the chimeric or humanized antibodies, the human FXIa-binding antibodies of the invention have further reduced antigenicity when administered to human subjects.

Camelid Antibodies

Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitate drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present invention is a camelid antibody or nanobody having high affinity for FXI and/or FXIa. In certain embodiments herein, the camelid antibody or nanobody is naturally produced in the camelid animal, i.e., is produced by the camelid following immunization with FXI and/or FXIa or a peptide fragment thereof, using techniques described herein for other antibodies. Alternatively, the FXI and/or FXIa-binding camelid nanobody is engineered, i.e., produced by selection for example from a library of phage displaying appropriately mutagenized camelid nanobody proteins using panning procedures with FXI and/or FXIa, and/or domains and/or peptide fragments thereof, as a target as described in the examples herein. Engineered nanobodies can further be customized by genetic engineering to have a half-life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214.

Bispecific Molecules and Multivalent Antibodies

In another aspect, the present invention features bispecific or multispecific molecules comprising a FXI and/or FXIa-binding antibody, or a fragment thereof, of the invention. An antibody of the invention, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for FXI and/or FXIa and a second binding specificity for a second target epitope. For example, the second target epitope is another epitope of FXI and/or FXIa different from the first target epitope.

Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., a Fab, Fab', F(ab')2, Fv, or a single chain Fv. The antibody may also be a light chain or heavy chain dimer, or any minimal fragment thereof such as a Fv or a single chain Fv construct as described in Ladner et al. U.S. Pat. No. 4,946,778.

Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen binding sites (see e.g., Holliger et al., 1993 Proc. Natl. Acad. Sci. USA 90:6444-6448; Poljak et al., 1994 Structure 2:1121-1123). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer Immunol. Immunother., 45(3-4):128-30; Wu et al., 1996 Immunotechnology, 2(1):21-36). scDb can be expressed in bacteria in soluble, active monomeric form (see Holliger and Winter, 1997 Cancer Immunol. Immunother., 45(34): 128-30; Wu et al., 1996 Immunotechnology, 2(1):21-36; Pluckthun and Pack, 1997 Immunotechnology, 3(2): 83-105; Ridgway et al., 1996 Protein Eng., 9(7):617-21). A diabody can be fused to Fc to generate a "di-diabody" (see Lu et al., 2004 J. Biol. Chem., 279(4):2856-65).

Other antibodies which can be employed in the bispecific molecules of the invention are murine, chimeric and humanized monoclonal antibodies.

Bispecific molecules can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-I-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand×Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present invention provides multivalent compounds comprising at least two identical or different antigen-binding portions of the antibodies of the invention binding to FXIa. The antigen-binding portions can be linked together via protein fusion or covalent or noncovalent linkage. Alternatively, methods of linkage have been described for the bispecific molecules. Tetravalent compounds can be obtained for example by cross-linking antibodies of the antibodies of the invention with an antibody that binds to the constant regions of the antibodies of the invention, for example the Fc or hinge region.

Trimerizing domain are described for example in Borean patent EP 1 012 280131. Pentamerizing modules are described for example in PCT/EP97/05897.

Antibodies with Extended Half Life

The present invention provides for antibodies that specifically bind to FXIa protein which have an extended half-life in vivo.

Many factors may affect a protein's half-life in vivo. For examples, kidney filtration, metabolism in the liver, degradation by proteolytic enzymes (proteases), and immunogenic responses (e.g., protein neutralization by antibodies and uptake by macrophages and dendritic cells). A variety of strategies can be used to extend the half-life of the antibodies of the present invention. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nanocarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies of the invention. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in *E. coli*, yeast, and mammalian cells. The tRNA incorporates a nonnative amino acid any place an amber codon is positioned, converting the amber from a stop codon to one that signals incorporation of the chemically specified amino acid.

Recombinant pegylation technology (rPEG) can also be used for serum half life extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum half-life of the protein is greatly increased. In contrast to traditional PEGylation, which requires chemical conjugation and repurification, the manufacturing process is greatly simplified and the product is homogeneous.

Polysialyation is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology includes the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin (e.g., human serum albumin; HSA) in order to make the antibody or antibody fragment more stable in vivo or have a longer half life in vivo. The techniques are well-known in the art, see, e.g., International Publication Nos. WO 93/15199, WO 93/15200, and WO 01/77137; and European Patent No. EP 413,622. In addition, in the context of a bispecific antibody as described above, the specificities of the antibody can be designed such that one binding domain of the antibody binds to FXIa while a second binding domain of the antibody binds to serum albumin, preferably HSA.

The strategies for increasing half-life is especially useful in nanobodies, fibronectin-based binders, and other antibodies or proteins for which increased in vivo half-life is desired.

Antibody Conjugates

The present invention provides antibodies or fragments thereof that specifically bind to a FXIa protein recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antigen-binding fragment of an antibody described herein (e.g., a Fab fragment, Fd fragment, Fv fragment, F(ab)2 fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to a FXIa protein may be recombined with one or more components, motifs, sections, parts, domains, fragments, etc. of one or more heterologous molecules.

Moreover, the antibodies or fragments thereof can be fused to marker sequences, such as a peptide to facilitate purification. In preferred embodiments, the marker amino acid sequence is a hexa-histidine peptide (SEQ ID NO: 48), such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine (SEQ ID NO: 48) provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In other embodiments, antibodies of the present invention or fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidinlbiotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I,), carbon (14C), sulfur (35S), tritium (3H), indium (115In, 113In, 112In, and 111In,), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142 Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and noradioactive paramagnetic metal ions.

The present invention further encompasses uses of antibodies or fragments thereof conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine.

Moreover, an antibody can be conjugated to therapeutic moieties such as a radioactive metal ion, such as alph-emitters such as 213Bi or macrocyclic chelators useful for conjugating radiometal ions, including but not limited to, 131In, 131 LU, 131Y, 131 Ho, 131Sm, to polypeptides. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Olin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Methods of Producing Antibodies

Nucleic Acids Encoding the Antibodies

The invention provides substantially purified nucleic acid molecules which encode polypeptides comprising segments or domains of the FXIa-binding antibody chains described above. Some of the nucleic acids of the invention comprise the nucleotide sequence encoding the heavy chain variable region shown in SEQ ID NO: 10 or 30, and/or the nucleotide sequence encoding the light chain variable region shown in SEQ ID NO: 20 or 40. In a specific embodiment, the nucleic acid molecules are those identified in Table 1. Some other nucleic acid molecules of the invention comprise nucleotide sequences that are substantially identical (e.g., at least 65, 80%, 95%, or 99%) to the nucleotide sequences of those identified in Table 1. When expressed from appropriate expression vectors, polypeptides encoded by these polynucleotides are capable of exhibiting FXI and/or FXIa antigen binding capacity.

Also provided in the invention are polynucleotides which encode at least one CDR region and usually all three CDR regions from the heavy or light chain of the FXIa-binding antibody set forth above. Some other polynucleotides encode all or substantially all of the variable region sequence of the heavy chain and/or the light chain of the FXIa-binding antibody set forth above. Because of the degeneracy of the code, a variety of nucleic acid sequences will encode each of the immunoglobulin amino acid sequences.

The nucleic acid molecules of the invention can encode both a variable region and a constant region of the antibody. Some of nucleic acid sequences of the invention comprise nucleotides encoding a heavy chain sequence that is substantially identical (e.g., at least 80%, 90%, or 99%) to the heavy chain sequence set forth in SEQ ID NO: 11 or 31. Some other nucleic acid sequences comprising nucleotide encoding a light chain sequence that is substantially identical (e.g., at least 80%, 90%, or 99%) to the light chain sequence set forth in SEQ ID NO: 21 or 41.

The polynucleotide sequences can be produced by de novo solid-phase DNA synthesis or by PCR mutagenesis of an existing sequence (e.g., sequences as described in the Examples below) encoding a FXIa-binding antibody or its binding fragment. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the FXI and/or FXIa-binding antibodies described above. Various expression vectors can be employed to express the polynucleotides encoding the FXIa-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the FXIa-binding polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on 5V40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding a FXIa-binding antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a FXIa-binding antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted FXIa-binding antibody sequences. More often, the inserted FXI and/or FXIa-binding antibody sequences are linked to a signal sequences before inclusion in the vector. Vectors to be used to receive sequences encoding FXI and/or FXIa-binding antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the FXI and/or FXIa-binding antibody chains can be either prokaryotic or eukaryotic. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express FXIa-binding polypeptides of the invention. Insect cells in combination with baculovirus vectors can also be used.

In some preferred embodiments, mammalian host cells are used to express and produce the FXI and/or FXIa-binding polypeptides of the present invention. These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, and transformed B-cells. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences.

These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express FXIa-binding antibody chains or binding fragments can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Framework or Fc Engineering

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the mutations as described in U.S. Pat. No. 6,277,375 to Ward can be used. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In a specific embodiment, an anti-FXI/FXIa antibody described herein (e.g., antibody comprising VL CDRs and VH CDRs of NOV1401) comprises a human IgG (e.g., IgG1) Fc region comprising two amino acid substitutions, D265A and P329A, to reduce the likelihood for ADCC or CDC caused by any surface-associated FXI. These Alanine substitutions have been shown to reduce ADCC and CDC (see, e.g., Idosugie et al., J. Immunol. 164:4178-4184, 2000; Shields et al., J. Biol. Chem. 276:6591-6604, 2001).

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen". Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Methods of Engineering Altered Antibodies

As discussed above, the FXIa-binding antibodies having VH and VL sequences or full length heavy and light chain sequences shown herein can be used to create new FXIa-binding antibodies by modifying full length heavy chain and/or light chain sequences, VH and/or VL sequences, or the constant region(s) attached thereto. Thus, in another aspect of the invention, the structural features of a FXIa-binding antibody of the invention are used to create structurally related FXIa-binding antibodies that retain at least one functional property of the antibodies of the invention, such as binding to human FXIa and also inhibiting one or more functional properties of FXIa (e.g., inhibit FXIa binding to the FXIa receptor, inhibit FXIa-dependent cell proliferation).

For example, one or more CDR regions of the antibodies of the present invention, or mutations thereof, can be combined recombinantly with known framework regions and/or other CDRs to create additional, recombinantly-engineered, FXIa-binding antibodies of the invention, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing a FXIa-binding antibody consisting of a heavy chain variable region antibody sequence having a CDR1 sequence selected from the group consisting of SEQ ID NOs: 3 and 23, a CDR2 sequence selected from the group consisting of SEQ ID NOs: 4 and 24, and/or a CDR3 sequence selected from the group consisting of SEQ ID NOs: 5 and 25; and a light chain variable region antibody sequence having a CDR1 sequence selected from the group consisting of SEQ ID NOs: 13 and 33, a CDR2 sequence selected from the group consisting of SEQ ID NOs: 14 and 34, and/or a CDR3 sequence selected from the group consisting of SEQ ID NOs: 15 and 35; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing a FXIa-binding antibody consisting of a heavy chain variable region antibody sequence having a CDR1 sequence selected from the group consisting of SEQ ID NOs: 6 and 26, a CDR2 sequence selected from the group consisting of SEQ ID NOs: 7 and 27, and/or a CDR3 sequence selected from the group consisting of SEQ ID NOs: 8 and 28; and a light chain variable region antibody sequence having a CDR1 sequence selected from the group consisting of SEQ ID NOs: 16 and 36, a CDR2 sequence selected from the group consisting of SEQ ID NOs: 17 and 37, and/or a CDR3 sequence selected from the group consisting of SEQ ID NOs: 18 and 38; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing a FXIa-binding antibody optimized for expression in a mammalian cell consisting of: a full length heavy chain antibody sequence having a sequence selected from the group of SEQ ID NOs: 11 or 31; and a full length light chain antibody sequence having a sequence selected from the group of 21 or 41; altering at least one amino acid residue within the full length heavy chain antibody sequence and/or the full length light chain antibody sequence to create at least one altered antibody sequence; and expressing the altered antibody sequence as a protein. In one embodiment, the alteration of the heavy or light chain is in the framework region of the heavy or light chain.

The altered antibody sequence can also be prepared by screening antibody libraries having fixed CDR3 sequences or minimal essential binding determinants as described in US2005/0255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the FXIa-binding antibodies described herein, which functional properties include, but are not limited to, specifically binding to human, cynomolgus, rat, and/or mouse FXIa; and the antibody inhibit FXIa-dependent cell proliferation in a F36E and/or Ba/F3-FXIaR cell proliferation assay.

In certain embodiments of the methods of engineering antibodies of the invention, mutations can be introduced randomly or selectively along all or part of an FXIa-binding antibody coding sequence and the resulting modified FXIa-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

In certain embodiments of the invention antibodies have been engineered to remove sites of deamidation. Deamidation is known to cause structural and functional changes in a peptide or protein. Deamindation can result in decreased bioactivity, as well as alterations in pharmacokinetics and antigenicity of the protein pharmaceutical. (*Anal Chem.* 2005 Mar. 1; 77(5):1432-9).

In certain embodiments of the invention the antibodies have been engineered to increase pI and improve their drug-like properties. The pI of a protein is a key determinant of the overall biophysical properties of a molecule. Antibodies that have low pIs have been known to be less soluble, less stable, and prone to aggregation. Further, the purification of antibodies with low pI is challenging and can be problematic especially during scale-up for clinical use. Increasing the pI of the anti-FXI/FXIa antibodies, or Fabs, of the invention improved their solubility, enabling the antibodies to be formulated at higher concentrations (>100 mg/ml). Formulation of the antibodies at high concentrations (e.g. >100 mg/ml) offers the advantage of being able to administer higher doses of the antibodies, which in turn may enable reduced dosing frequency, a significant advantage for treatment of chronic diseases including thrombotic and/or thromboembolic disorders. Higher pIs may also increase the FcRn-mediated recycling of the IgG version of the antibody thus enabling the drug to persist in the body for a longer duration, requiring fewer injections. Finally, the overall stability of the antibodies is significantly improved due to the higher pI resulting in longer shelf-life and bioactivity in vivo. Preferably, the pI is greater than or equal to 8.2.

The functional properties of the altered antibodies can be assessed using standard assays available in the art and/or described herein, such as those set forth in the Examples (e.g., ELISAs).

Prophylactic and Therapeutic Uses

Antibodies that bind FXI and/or FXIa as described herein (e.g., antibodies described in Table 1, such as, anti-FXI/FXIa antibodies comprising VL CDRs and VHCDRs of NOV1401), can be used at a therapeutically useful concentration for the treatment of a thromboembolic disease or disorder (e.g., thrombic stroke, atrial fibrillation, stroke prevention in atrial fibrillation (SPAF), deep vein thrombosis, venous thromboembolism, pulmonary embolism, acute coronary syndromes (ACS), ischemic stroke, acute limb ischemia, chronic thromboembolic pulmonary hypertension, or systemic embolism) by administering to a subject in need thereof an effective amount of the antibodies or antigen binding fragments of the invention. The present invention provides a method of treating thromboembolic disorder (e.g., thrombotic disorders) by administering to a subject in need thereof an effective amount of the antibodies of the invention. The present invention provides a method of treating thromboembolic disorders (e.g., thrombic stroke, atrial fibrillation, stroke prevention in atrial fibrillation (SPAF), deep vein thrombosis, venous thromboembolism, pulmonary embolism, acute coronary syndromes (ACS), ischemic stroke, acute limb ischemia, chronic thromboembolic pulmonary hypertension, or systemic embolism) by administering to a subject in need thereof an effective amount of the antibodies of the invention.

The antibodies described herein (e.g., antibodies described in Table 1, such as, NOV1401 or anti-FXI/FXIa antibodies comprising VL CDRs and VHCDRs of NOV1401) can be used, inter alia, to prevent treat, prevent, and improve thromboembolic conditions or disorders, including but not limited to thrombotic disorders, as described in greater detail herein.

The antibodies provided herein (e.g., antibodies described in Table 1, such as, anti-FXI/FXIa antibodies comprising VL CDRs and VHCDRs of NOV1401) can also be used in combination with other agents for the prevention, treatment, or improvement of thromboembolic disorders. For example, statin therapies may be used in combination with the FXIa antibodies and antigen binding fragments of the invention for the treatment of patients with thrombotic and/or thromboembolic disorders.

In a specific embodiment, provided herein is a method of treating or preventing stroke in a patient with atrial fibrillation, comprising administering to the patient in need hereof an effective amount of an anti-FXI/FXIa antibody described herein, for example, an anti-FXI/FXIa antibody described in Table 1, such as, NOV1401 or anti-FXI/FXIa antibodies comprising VL CDRs and VHCDRs of NOV1401.

In a specific embodiment, provided herein is a method of managing or preventing risks or conditions associated with atrial fibrillation (AF), such as embolic stroke and systemic embolism, in a patient with atrial fibrillation, comprising administering to the patient in need hereof an effective amount of an anti-FXI/FXIa antibody described herein, for example, an anti-FXI/FXIa antibody described in Table 1, such as, NOV1401 or anti-FXI/FXIa antibodies comprising VL CDRs and VHCDRs of NOV1401.

In a specific embodiment, provided herein is a method of treating, managing or preventing conditions associated with atrial fibrillation (AF), such as embolic stroke and systemic embolism, in a patient with atrial fibrillation, comprising administering to the patient in need hereof an effective amount of an anti-FXI/FXIa antibody described herein, for example, an anti-FXI/FXIa antibody described in Table 1, such as, NOV1401 or anti-FXI/FXIa antibodies comprising VL CDRs and VHCDRs of NOV1401. In particular embodiments, an AF patient has a high bleeding risk.

In a specific embodiment, provided herein is a method of treating, managing or preventing deep vein thrombosis or conditions associated therewith, in a subject (e.g., a subject with, or at risk of developing, deep vein thrombosis), comprising administering to the subject in need hereof an effective amount of an anti-FXI/FXIa antibody described herein, for example, an anti-FXI/FXIa antibody described in Table 1, such as, NOV1401 or anti-FXI/FXIa antibodies comprising VL CDRs and VHCDRs of NOV1401.

In a specific embodiment, provided herein is a method of treating, managing or preventing venous thromboembolism (VIE) or conditions associated therewith, in a subject (e.g., a subject with, or at risk of developing, venous thromboembolism), comprising administering to the subject in need hereof an effective amount of an anti-FXI/FXIa antibody described herein, for example, an anti-FXI/FXIa antibody described in Table 1, such as, NOV1401 or anti-FXI/FXIa antibodies comprising VL CDRs and VHCDRs of NOV1401. In particular embodiments, subjects being treated with an anti-FXI/FXIa antibody provided herein have experienced 1) a first unprovoked VIE with low risk for bleeding, 2) recurrence of unprovoked VIE, or 3) VIE associated with thrombophilia including cancer patients.

In a specific embodiment, provided herein is a method of treating, managing or preventing pulmonary embolism or conditions associated therewith, in a subject (e.g., a subject with, or at risk of developing, pulmonary embolism), comprising administering to the subject in need hereof an effective amount of an anti-FXI/FXIa antibody described herein, for example, an anti-FXI/FXIa antibody described in Table 1, such as, NOV1401 or anti-FXI/FXIa antibodies comprising VL CDRs and VHCDRs of NOV1401.

In a specific embodiment, provided herein is a method of treating, managing or preventing acute coronary syndromes (ACS) or conditions associated therewith, in a subject, comprising administering to the subject in need hereof an effective amount of an anti-FXI/FXIa antibody described herein, for example, an anti-FXI/FXIa antibody described in Table 1, such as, NOV1401 or anti-FXI/FXIa antibodies comprising VL CDRs and VHCDRs of NOV1401.

In a specific embodiment, provided herein is a method of treating, managing or preventing ischemic stroke, in a subject (e.g., a subject with, or at risk of developing, ischemic stroke), comprising administering to the subject in need hereof an effective amount of an anti-FXI/FXIa antibody described herein, for example, an anti-FXI/FXIa antibody described in Table 1, such as, NOV1401 or anti-FXI/FXIa antibodies comprising VL CDRs and VHCDRs of NOV1401.

In a specific embodiment, provided herein is a method of treating, managing or preventing acute limb ischemia, in a subject, comprising administering to the subject in need hereof an effective amount of an anti-FXI/FXIa antibody described herein, for example, an anti-FXI/FXIa antibody described in Table 1, such as, NOV1401 or anti-FXI/FXIa antibodies comprising VL CDRs and VHCDRs of NOV1401.

In a specific embodiment, provided herein is a method of treating, managing or preventing chronic thromboembolic pulmonary hypertension, in a subject, comprising administering to the subject in need hereof an effective amount of an anti-FXI/FXIa antibody described herein, for example, an anti-FXI/FXIa antibody described in Table 1, such as, NOV1401 or anti-FXI/FXIa antibodies comprising VL CDRs and VHCDRs of NOV1401.

In a specific embodiment, provided herein is a method of treating, managing or preventing systemic embolism, in a subject (e.g., a subject with, or at risk of developing, systemic embolism), comprising administering to the subject in need hereof an effective amount of an anti-FXI/FXIa antibody described herein, for example, an anti-FXI/FXIa antibody described in Table 1, such as, NOV1401 or anti-FXI/FXIa antibodies comprising VL CDRs and VHCDRs of NOV1401.

In a certain embodiment, provided herein is a method of treating, managing, or preventing thromboembolic conditions that are catheter-related conditions (e.g., Hickman catheter in cancer patients) in which catheters become thrombosed, or extracorporeal membrane oxygenation (ECMO), in which the tubing develops clots, comprising administering to the subject in need hereof an effective amount of an anti-FXI/FXIa antibody described herein, for example, an anti-FXI/FXIa antibody described in Table 1, such as, NOV1401 or anti-FXI/FXIa antibodies comprising VL CDRs and VHCDRs of NOV1401.

In particular embodiments, subjects in need of treatment with an anti-FXI/FXIa antibody described herein, for example, an anti-FXI/FXIa antibody described in Table 1, such as, NOV1401 or anti-FXI/FXIa antibodies comprising VL CDRs and VHCDRs of NOV1401, may include:
  Subjects with indications for chronic anticoagulation therapy (e.g., AF, left ventricular thrombus, prior cardioembolic stroke)
  subjects at intermediate-to-high risk for major bleeding;
  subjects undergoing elective or primary percutaneous coronary intervention (PCI) with stenting which may be require to receive dual antiplatelet therapy (aspirin and P2Y12 receptor antagonists) to prevent stent thrombosis.

In particular embodiments, one of the following conditions can be treated or managed with an anti-FXI/FXIa antibody described herein, for example, an anti-FXI/FXIa antibody described in Table 1, such as, NOV1401 or anti-FXI/FXIa antibodies comprising VL CDRs and VHCDRs of NOV1401:
  thromboembolism in subjects with suspected or confirmed cardiac arrhythmia such as paroxysmal, persistent or permanent atrial fibrillation or atrial flutter;
  stroke prevention in atrial fibrillation (SPAF), a subpopulation of which is AF patients undergoing percutaneous coronary interventions (PCI);
  acute venous thromboembolic events (VTE) treatment and extended secondary VTE prevention in patients at high risk for bleeding;
  cerebral and cardiovascular events in secondary prevention after transient ischemic attack (TIA) or non-disabling stroke and prevention of thromboembolic events in heart failure with sinus rhythm;
  clot formation in left atrium and thromboembolism in subjects undergoing cardioversion for cardiac arrhythmia;
  thrombosis before, during and after ablation procedure for cardiac arrhythmia;
  venous thrombosis, this includes but not exclusively, treatment and secondary prevention of deep or superficial veins thrombosis in the lower members or upper member, thrombosis in the abdominal and thoracic veins, sinus thrombosis and thrombosis of jugular veins;
  thrombosis on any artificial surface in the veins like catheter or pacemaker wires;
  pulmonary embolism in patients with or without venous thrombosis;
  Chronic Thromboembolic Pulmonary Hypertension (CTEPH);
  arterial thrombosis on ruptured atherosclerotic plaque, thrombosis on intra-arterial prosthesis or catheter and thrombosis in apparently normal arteries, this includes but not exclusively acute coronary syndromes, ST elevation myocardial infarction, non ST elevation myocardial infarction, unstable angina, stent thrombosis, thrombosis of any artificial surface in the arterial system and thrombosis of pulmonary arteries in subjects with or without pulmonary hypertension;
  thrombosis and thromboembolism in patients undergoing percutaneous coronary interventions (PCI);
  cardioembolic and cryptogenic strokes;
  thrombosis in patients with invasive and non-invasive cancer malignancies;
  thrombosis over an indwelling catheter;
  thrombosis and thromboembolism in severely ill patients;
  cardiac thrombosis and thromboembolism, this includes but not exclusively cardiac thrombosis after myocardial infarction, cardiac thrombosis related to condition such as cardiac aneurysm, myocardial fibrosis, cardiac enlargement and insufficiency, myocarditis and artificial surface in the heart;
  thromboembolism in patients with valvular heart disease with or without atrial fibrillation;
  thromboembolism over valvular mechanic or biologic prostheses;
  injuries or trauma in patients who had native or artificial cardiac patches, arterial or venous conduit tubes after heart repair of simple or complex cardiac malformations;
  venous thrombosis and thromboembolism after knee replacement surgery, hip replacement surgery, and orthopedic surgery, thoracic or abdominal surgery;
  arterial or venous thrombosis after neurosurgery including intracranial and spinal cord interventions;
  congenital or acquired thrombophilia including but not exclusively factor V Leiden, prothrombin mutation, antithrombin III, protein C and protein S deficiencies, factor XIII mutation, familial dysfibrinogenemia, congenital deficiency of plasminogen, increased levels of factor XI, sickle cell disease, antiphospholipid syndrome, autoimmune disease, chronic bowel disease, nephrotic syndrome, hemolytic uremia, myeloproliferative disease, disseminated intra vascular coagulation, paroxysmal nocturnal hemoglobinuria and heparin induced thrombopenia;
  thrombosis and thromboembolism in chronic kidney disease; and thrombosis and thromboembolism in patients undergoing hemodialysis and extra-corporal membrane oxygenation.

In a specific aspect, provided herein are methods of managing bleeding in a patient being treated or administered an anti-FXI/FXIa antibody provided herein (e.g., an antibody described in Table 1, such as, an anti-FXI/FXIa antibody comprising VL CDRs and VHCDRs of NOV1401), for example, bleeding associated with trauma, surgery menstruation or post-delivery, said method comprises reversing of the anticoagulant effect. FXI deficiency is rarely associated with spontaneous bleeding manifestations; in specific aspects, bleeding is most typically associated with trauma, surgery, menstruation or post-delivery. Prolonged bleeding may occur after a major trauma or after surgery involving organs with high fibrinolytic area such as buccal, nasal, genital or urinary mucosa. Tooth extraction, tonsillectomy and ablation of the uterus or prostate are examples of surgeries that entail a high risk of bleeding. People with the disorder also have a strong tendency to develop epistaxis and ecchymoses, and more rarely, bleeding into the urine or intestines. Spontaneous muscle or joint and intracranial bleeding frequency is not increased in patients with FXI deficiency. Venous puncture is not usually associated with an extended bleeding. Other genetic mutations associated with FXI deficiency may contribute to the heterogeneous and unpredictable bleeding tendency in patients with severe FXI deficiency. Concomitant use of antiplatelets, other anticoagulants and fibrinolytic agents can increase the risk of bleeding.

In particular embodiments, provided herein is a method of managing bleeding in a patient being treated with an anti-FXI/FXIa antibody provided herein (e.g., an antibody described in Table 1, such as, an anti-FXI/FXIa antibody comprising VL CDRs and VHCDRs of NOV1401), said method comprises temporarily reversing of the anticoagulant effect for a sufficient time to manage the bleeding. In specific embodiments, the step of reversing of the anticoagulant effect comprises (i) fluid replacement using colloids, crystalloids, human plasma or plasma proteins such as albumin; or (ii) transfusion with packed red blood or whole blood. In a particular embodiment, therapeutic agents for reversal of the effect of anticoagulants, for example, in cases of severe emergency, include, but are not limited to, prohemostasis blood components such as fresh frozen plasma (FFP), prothrombin complex concentrates (PCC) and activated PCC [(APCC); e.g. factor VIII inhibitor bypass activity (FEIBA)] and recombinant activated factor VII (rFVIIa). In one embodiment, a regimen comprising administration of rFVIIa at a dose of 30 µg/kg followed by administration of rFVIIa at a dose of 15-30 µg/kg every 2-4 hours for 24-48 hours in addition to tranexamic acid 1 g every 6 hours for 5 to 7 days may have potential to recover hemostasis and stop bleeding in subjects treated with an anti-FXI/FXIa antibody provided herein (e.g., NOV1401 or an antibody comprising VL CDRs and VH CDRs of NOV1401) who are undergoing major surgery and in patients with an active non-accessible bleeding site. For instance, Riddell et al reported experience in 4 patients with severe FXI deficiency without inhibitor undergoing surgery (Riddell et al., 2011, Thromb. Haemost.; 106: 521-527); patients were administered rFVIIa 30 µg/kg and tranexamic acid 1 g i.v. at induction of anesthesia. Subsequent bolus doses of rFVIIa 15-30 µg/kg were administered at 2 to 4 hourly intervals as guided by rotational thromboelastometry (ROTEM) results. Patients were treated with rFVIIa at above mentioned doses for 24-48 hours. Tranexamic acid 1 g every six-hourly was continued for five days. In this small series, rFVIIa at doses as low as 15-30 µg/kg in combination with tranexamic acid was safe and effective in correcting the hemostatic defect in severe FXI deficiency in this study. In another study comprising 4 patients with severe FXI deficiency with inhibitor (autologous neutralizing FXI antibodies usually acquired after transfusion or administration of blood products to patients with severe FXI deficiency) who experienced 5 surgeries, the authors (Livnat et al., 2009, Thromb. Haemost.; 102: 487-492) applied the following protocol: 1 g of tranexamic acid orally two hours before surgery, then patients received immediately prior to the interventions another 1 g tranexamic acid i.v. Recombinant FVIIa at doses ranging from 15 to 30 µg/kg was infused at the completion of surgery. Subsequently, oral tranexamic acid 1 g was given every 6 hour for at least 7 days. Fibrin glue was sprayed at the bed of the extirpated gallbladder in one patient. This protocol secured normal hemostasis in patients with severe FXI deficiency with inhibitor.

In one aspect, fibrin glue can be used to restore local hemostasis during dental surgery in patients with FXI deficiency (Bolton-Maggs (2000) Haemophilia; 6 (S1):100-9). In a certain embodiment with respect to methods to manage bleeding in patients being treated with an anti-FXI/FXIa antibody provided herein (e.g., NOV1401), a regimen consisting of tranexamic acid 1 g every 6 hours for 5 to 7 days associated with the use of fibrin glue could be used to establish local hemostasis in subjects undergoing minor surgery and in subjects with accessible bleeding site, including oral and nasal bleeding events.

Pharmaceutical Compositions

The invention provides pharmaceutical compositions comprising the FXIa-binding antibodies (intact or binding fragments) formulated together with a pharmaceutically acceptable carrier. The compositions can additionally contain one or more other therapeutic agents that are suitable for treating or preventing, for example, thromboembolic disorders (e.g., thrombotic disorders). Pharmaceutically acceptable carriers enhance or stabilize the composition, or can be used to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravenous (i.v.), intramuscular (i.m.), intraperitoneal (i.p.), or subcutaneous (s.c.), or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

In particular aspects, anti-FXI/FXIa antibodies described herein (e.g., antibodies described in Table 1, such as NOV1401 or antibodies comprising LCDRs and HCDRs of NOV1401) are formulated at approximately 75 mg/1 mL to approximately 200 mg/1 mL concentration, in liquid vials for subcutaneous injections. In particular embodiments, the pharmaceutical composition comprises a pharmaceutical carrier or excipient, for example, sucrose, and polysorbate 20. In particular embodiments, the pharmaceutical composition comprises L-histidine and/or histidine HCl monohydrate. In certain embodiments, the pharmaceutical composition has a pH of approximately 4 to 7, or 5 to 6.

In particular aspects, anti-FXI/FXIa antibodies described herein (e.g., antibodies described in Table 1, such as NOV1401 or antibodies comprising LCDRs and HCDRs of NOV1401) are formulated at 150 mg/1 mL concentration, in liquid vials for subcutaneous injections. In one embodiment, the 150 mg/mL liquid formulation contains 150 mg anti-FXI/FXIa antibody, L-histidine, histidine HCl monohydrate, sucrose, and polysorbate 20, with a pH=5.5±0.5. The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the FXIa-binding antibody is employed in the pharmaceutical compositions of the invention. The FXIa-binding antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician can start doses of the antibodies of the invention employed in the pharmaceutical composition at levels lower than that required to achieve the desired therapeutic effect and gradually increase the dosage until the desired effect is achieved. In general, effective doses of the compositions of the present invention, for the treatment of a thrombotic and/or thromboembolic disorders described herein vary depending upon many different factors, including means of administration, target site, physiological state of the patient, other medications administered, and whether treatment is prophylactic or therapeutic. Treatment dosages need to be titrated to optimize safety and efficacy. For systemic administration with an antibody, the dosage ranges from about 0.01 to 15 mg/kg of the host body weight. For administration (e.g., subcutaneous administration) with an antibody, the dosage may range from 0.1 mg to 5 mg or from 1 mg to 600 mg. For example, an anti-FXI/FXIa antibody described herein can be administered at a dose of 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, or 5.0 mg/kg. An exemplary treatment regime entails systemic administration once per every two weeks or once a month or once every 3 to 6 months. An exemplary treatment regime entails systemic administration once per week, once per every two weeks, once per every three weeks, once a month, or once every 3 to 6 months, or as needed (PRN).

In a certain embodiment, an anti-FXI/FXIa antibody described herein (e.g., an antibody described in Table 1, such as NOV1401 or an antibody comprising VL CDRs and VH CDRs of NOV1401) is administered, for example by i.v. or s.c., at a dose of 3 mg/kg.

In a certain embodiment, an anti-FXI/FXIa antibody described herein (e.g., an antibody described in Table 1, such as NOV1401 or an antibody comprising VL CDRs and VH CDRs of NOV1401) is administered, for example by i.v. or s.c., at a dose of 10 mg/kg.

In a certain embodiment, an anti-FXI/FXIa antibody described herein (e.g., an antibody described in Table 1, such as NOV1401 or an antibody comprising VL CDRs and VH CDRs of NOV1401) is administered, for example by i.v. or s.c., at a dose of 30 mg/kg.

In a certain embodiment, an anti-FXI/FXIa antibody described herein (e.g., an antibody described in Table 1, such as NOV1401 or an antibody comprising VL CDRs and VH CDRs of NOV1401) is administered, for example by i.v. or s.c., at a dose of 50 mg/kg.

In a certain embodiment, an anti-FXI/FXIa antibody described herein (e.g., an antibody described in Table 1, such as NOV1401 or an antibody comprising VL CDRs and VH CDRs of NOV1401) is administered, for example by i.v. or s.c., at a dose of 100 mg/kg.

In a certain embodiment, an anti-FXI/FXIa antibody described herein (e.g., an antibody described in Table 1, such as NOV1401 or an antibody comprising VL CDRs and VH CDRs of NOV1401) is administered, for example by i.v. or s.c. route, at a dose in the range of 5 mg to 600 mg.

In a certain embodiment, an anti-FXI/FXIa antibody described herein (e.g., an antibody described in Table 1, such as NOV1401 or an antibody comprising VL CDRs and VH CDRs of NOV1401) is administered, for example by i.v. or s.c. route, at a dose of approximately 5 mg, 10 mg, 15 mg, 20 mg, 30 mg, 40 mg, 50 mg, 60 mg, 90 mg, 100 mg, 120 mg, 150 mg, 180 mg, 200 mg, 210 mg, 240 mg, 250 mg, 270 mg, 300 mg, 330 mg, 350 mg, 360 mg, 390 mg, 400 mg, 420 mg, 450 mg, 480 mg, 500 mg, 510 mg, 540 mg, 550 mg, 570 mg, or 600 mg.

In a certain embodiment, an anti-FXI/FXIa antibody described herein (e.g., an antibody described in Table 1, such as NOV1401 or an antibody comprising VL CDRs and VH CDRs of NOV1401) is administered, for example by s.c. route, at a dose of 5 mg.

In a certain embodiment, an anti-FXI/FXIa antibody described herein (e.g., an antibody described in Table 1, such as NOV1401 or an antibody comprising VL CDRs and VH CDRs of NOV1401) is administered, for example by s.c. route, at a dose of 15 mg.

In a certain embodiment, an anti-FXI/FXIa antibody described herein (e.g., an antibody described in Table 1, such as NOV1401 or an antibody comprising VL CDRs and VH CDRs of NOV1401) is administered, for example by s.c. route, at a dose of 50 mg.

In a certain embodiment, an anti-FXI/FXIa antibody described herein (e.g., an antibody described in Table 1, such as NOV1401 or an antibody comprising VL CDRs and VH CDRs of NOV1401) is administered, for example by s.c. route, at a dose of 150 mg.

In a certain embodiment, an anti-FXI/FXIa antibody described herein (e.g., an antibody described in Table 1, such as NOV1401 or an antibody comprising VL CDRs and VH CDRs of NOV1401) is administered, for example by s.c. route, at a dose of 300 mg.

In a certain embodiment, an anti-FXI/FXIa antibody described herein (e.g., an antibody described in Table 1, such as NOV1401 or an antibody comprising VL CDRs and VH CDRs of NOV1401) is administered, for example by s.c. route, at a dose of 600 mg.

In a certain embodiment, an anti-FXI/FXIa antibody described herein (e.g., an antibody described in Table 1, such as NOV1401 or an antibody comprising VL CDRs and VH CDRs of NOV1401) is administered, for example by i.v. or s.c. route, at a dose sufficient to achieve a mean duration of aPTT prolongation of 2-fold or greater for a period no longer than 30 days, 35 days, 36 days, 37 days, 38 days, 39 days, 40 days, 41 days, 42 days, 43 days, 44 days, 45 days, or 50 days.

In a certain embodiment, an anti-FXI/FXIa antibody described herein (e.g., an antibody described in Table 1, such as NOV1401 or an antibody comprising VL CDRs and VH CDRs of NOV1401) is administered, for example by i.v. or s.c. route, at a dose sufficient to achieve a mean duration of aPTT prolongation of 2-fold or greater for a period no longer than 42 days.

Antibody is usually administered on multiple occasions. Intervals between single dosages can be weekly, biweekly, monthly or yearly. Intervals can also be irregular as indicated by measuring blood levels of FXI- and/or FXIa-binding antibody in the patient. In addition alternative dosing intervals can be determined by a physician and administered monthly or as necessary to be efficacious. In some methods of systemic administration, dosage is adjusted to achieve a plasma antibody concentration of 1-1000 μg/mL or 1-1200 μg/mL, and in some methods 25-500 μg/mL. Alternatively, antibody can be administered as a sustained release formulation, in which case less frequent administration is required. Dosage and frequency vary depending on the half-life of the antibody and its target in the patient. In general, human and humanized antibodies show longer half-life, in humans, than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regimen.

EXAMPLES

The following examples are provided to further illustrate the invention but not to limit its scope. Other variants of the invention will be readily apparent to one of ordinary skill in the art and are encompassed by the appended claims.

Example 1

Human Fab Phage Library Panning

For the selection of antibodies recognizing human Factor XI, multiple panning strategies were utilized. Therapeutic antibodies against different variants of human Factor XI and rabbit Factor XIa catalytic domain protein were generated by the selection of clones that bound to Factor XI using as a source of antibody a commercially available phage display library, the Morphosys HuCAL PLATINUM® library. The phagemid library is based on the HuCAL® concept (Knappik et al., 2000, J Mol Biol 296: 57-86) and employs the CysDisplay™ technology for displaying the Fab on the phage surface (WO01/05950). For the isolation of anti-Factor XI antibodies liquid phase panning strategies were employed.

Cross-reactivity Analysis

Purified Fabs were tested in ELISA for binding to the different variants of human Factor XI (Factor XI, Factor XIa & Factor XIa catalytic domain) and Rabbit Factor XIa catalytic domain biotinylated proteins. For this purpose Maxisorp™ (Nunc) 384 well plates were coated with 10 ug/ml of NeutrAvidin in PBS overnight at 4° C. Antigens were captured on the NeutrAvidin via the biotin at room temperature (RT) for 30 minutes. Binding of Fabs at different concentrations was detected by $F(ab)_2$ specific goat anti-human IgG conjugated to alkaline phosphatase (diluted 1:5000) using Attophos fluorescence substrate (Roche, catalog #11681982001). Fluorescence emission at 535 nm was recorded with excitation at 430 nm.

Conversion to IgG and IgG Expression

In order to express full length IgG in CAP-T cells, variable domain fragments of heavy (VH) and light chains (VL) were subcloned from Fab expression vectors into appropriate pMorph®_hIg vectors for human IgG1. Two amino acid substitutions (D265A and P329A) were introduced in the Fc portion to reduce the likelihood for ADCC or CDC caused by any surface-associated FXI. These Alanine substitutions have been shown to reduce ADCC and CDC (see, e.g., Idosugie et al., J. Immunol. 164:4178-4184, 2000; Shields et al., J. Biol. Chem. 276:6591-6604, 2001). The cell culture supernatant was harvested 7 days post transfection. After sterile filtration, the solution was subjected to Protein A affinity chromatography using a liquid handling station. Samples were eluted in a 50 nM Citrate, 140 nM NaOH and pH neutralized with 1M Tris buffer and sterile filtered (0.2 μm pore size). Protein concentrations were determined by UV-spectrophotometry at 280 nm and purity of IgGs was analyzed under denaturing, reducing conditions in SDS-PAGE.

Example 2

Binding Data

Surface Plasmon Resonance (SPR) Analysis for the FXI Catalytic Domain.

The SPR measurements were performed on a BIACORE™ T200 surface plasmon resonance based optical biosensor (BIACORE™, GE Healthcare, Uppsala). Series S sensor chips (CM5), immobilization kits and regeneration buffer were purchased from GE Healthcare (Uppsala). Two different assay setups were performed depending on the ligand format, IgG or Fab. First, the surface was activated by N-hydroxysuccinimide (NHS) and N-(3-dimethylaminopropyl)-N-ethylcarbodiimide hydrochloride (EDC). The NOV1401-Fab was covalently attached to the activated dextran matrix on a CM5 chip by the standard amine-coupling method (GE Healthcare, Uppsala). For the NOV1401-IgG a capture assay was performed and a goat anti-human IgG-Fc antibody (JIR) was immobilized on the chip at 14000 RUs. Remaining active surface groups were inactivated with Ethanolamine (EA). A reference cell without immobilized ligand was prepared and the system equilibrated with 1×HBS-EP+buffer (10 mM HEPES, 150 mM NaCl, 3 mM EDTA, 0.05% P20, pH 7.4, Teknova H8022).

All binding experiments were performed at 25° C. at a flow rate of 50 µl/min using HBS-EP+buffer. For the capture assay NOV1401-IgG was captured until reaching an RU level of 80. For kinetic studies a dilution series of the FXI catalytic domain with concentrations ranging from 0-200 nM in HBS-EP+buffer was used. Association time was 120 s and the dissociation time 180 s. The surface was regenerated with a single injection of 10 mM Glycine pH 1.5 (contact time 60 s, stabilization time 120 s). Data processing as well as $k_{on}$, $k_{off}$ and $K_D$ determination were accomplished with the T200 BiaEvaluation software version 1.0. Double referencing (subtraction of reference and blank injection) was applied to correct for bulk effects and other systematic artefacts. Sensograms were fitted by applying a 1:1 binding model ($R_{max}$ set at global).

Solution Equilibrium Titration (SET) for FXI and FXIa 22 serial 1.6n dilutions of the antigens were prepared in sample buffer (PBS pH 7.4 containing 0.5% BSA and 0.02% Tween 20) and a constant concentration of NOV1401-Fab (200 pM for huFXI and 500 pM for huFXIa) or NOV1401-Antibody (10 pM for huFXI and huFXIa) was added to each antigen concentration. Starting concentrations for the antigen dilution series were 100 nM for huFXIa and 20 nM huFXI (Fab assay) or 1 nM (IgG assay). 60 µl/well of each dilution mix was distributed in duplicates to a 384-well polypropylene MTP. Sample buffer served as negative control and a sample containing no antigen as positive control (Bmax). The plate was sealed and incubated overnight at RT on a shaker. A standard 384-well MSD array MTP was coated with 30 µl/well of 0.1 µg/ml huFXIa (for huFXIa and huFXI) diluted in PBS, sealed and incubated overnight at 4° C.

After incubation and three times washing with TBST (TBS containing 0.05% Tween 20) the antigen-coated MSD plate was blocked with 50 µl/well blocking buffer (PBS containing 5% BSA) and incubated for 1 h at RT on a shaker. The wash step was repeated and 30 µl/well of the Fab-/IgG-antigen preparation was transferred from the polypropylene MTP to the antigen coated MSD plate and incubated for 20 min at RT on a shaker. After an additional wash step, 30 µl of 0.5 µg/ml ECL-labeled goat anti-human-IgG/Fab detection antibody (MSD) diluted in sample buffer was added to each well and incubated for 30 min at RT with shaking. After washing the plate again three times, 35 µl of read buffer (MSD) was added to each well. Electrochemiluminescence (ECL) signals were generated and detected with the MSD Sector Imager 6000.

Average ECL-signals were calculated from duplicate measurements within each assay. Data were baseline adjusted by subtracting the lowest value from all data points and plotted against the corresponding antigen concentration. $K_D$ values were determined by fitting the plot with the following 1:1 (for Fab) or 1:2 (for IgG) fit model (according to Piehler et al., 1997).

Results

The results are summarized in Tables 3 and 4. For both NOV1401 formats, Fab and IgG, $K_D$ values of approximately 20 nM were obtained for the FXI catalytic domain as determined by BIACORE™. Affinities of the Fab to both the activated and zymogen FXI were in the pM range and were 66 and 300 times higher than the affinity to the catalytic domain, respectively. Based on their high affinities these interactions were measured by SET assays. The NOV1401-Fab exhibited a five-fold higher affinity to the zymogen FXI (62 pM) than to the activated FXI (305 pM). Affinities of the NOV1401-IgG to both the dimeric zymogen and activated FXI are marked as apparent $K_D$ values since the interaction might influenced by avidity effects.

To confirm that NOV2401 also binds to cynomolgus monkey FXI, SET experiments were performed with activated cynomolgus monkey FXI and cynomolgus monkey FXI zymogen resulting in apparent $K_D$ values of 12.5±6.6 pM (N=2) and 5.0±0.7 pM (N=2), respectively. Hence, the affinities of NOV1401 to cynomolgus monkey FXI proteins (active form and zymogen) are comparable to those for binding to human FXI (Table 3).

TABLE 2

$K_D$ values and kinetic binding parameters of NOV1401-Fab/IgG for human FXI catalytic domain as determined by BIACORE™.

| Catalytic domain | $k_a$ (1/Ms) | $k_d$ (1/s) | $K_D$ (nM) | n |
|---|---|---|---|---|
| NOV1401-Fab | 3.2 ± 0.5E+4 | 6.1 ± 1.8E−4 | 19 ± 6 | 3 |
| NOV1401-IgG | 4.2 ± 1.6E+4 | 8.8 ± 2.2E−4 | 21 ± 3 | 2 |

TABLE 3

$K_D$ values of NOV1401-Fab/IgG for human FXI activated and zymogen determined by the in solution equilibrium titration (SET). *Only apparent $K_D$ values reported, since the interaction might be influenced by avidity effects.

|  | $K_D$ [pM] | n |
|---|---|---|
| NOV1401-Fab |  |  |
| Human FXI activated | 305 ± 8 | 3 |
| Human FXI zymogen | 62 ± 18 | 3 |
| NOV1401-IgG |  |  |
| Human FXI activated | 4.7 ± 2.1* | 3 |
| Human FXI zymogen | 1.3 ± 0.3* | 3 |

Reference: Piehler et al. Assessment of affinity constants by rapid solid phase detection of equilibrium binding in a flow system, J. Immunol. Meth. 1997. 189-206

Example 3

Biochemical Assay: Inhibition of FXIa in Activity Assay Using Fluorescent Peptide as Substrate The activity of human FXIa (Kordia Life Science NL, catalogue number HFXIa 1111a) is determined by monitoring the cleavage of a fluorescently labelled peptide with the sequence D-Leu-Pro-Arg*Rh110-D-Pro (product number BS-2494; Biosyntan GmbH, Berlin, Germany). In the substrate sequence written above, * indicates the scissile bond, D-Leu: D-leucine, Pro: proline, Arg: arginine, Rh110: rhodamine 110, D-Pro: D-proline). FXIa mediated cleavage of the scissile bond of the peptide substrate leads to an increase of fluorescence intensity of the rhodamine 110 when using excitation and emission wavelengths of 485 nm and 535 nm, respectively. Fluorescence intensity is continuously measured using the microtiter plate reader Safire2 (TECAN, Maennedorf, Switzerland) at room temperature (RT). The assay buffer contains 50 mM HEPES at pH 7.4, 125 mM NaCl, 5 mM $CaCl_2$ and 0.05% (w/v) CHAPS. In the final activity assay, human FXIa and the substrate BS-2494 have assay concentrations of 0.1 nM and 0.5 µM, respectively. Under these conditions, the increase of fluorescence intensity over time is linear for at least 60 minutes.

For testing the inhibitory activity of antibodies, serial dilutions of antibodies are prepared in PBS buffer (137 mM NaCl, 2.7 mM KCl, 10 mM $Na_2HPO_4$, 1.8 mM $KH_2PO_4$) containing 0.05% (w/v) CHAPS. Two µL of antibody solution are pre-incubated with 10 µL FXIa solution (in assay buffer) for 60 minutes at RT. After the pre-incubation step, 10 µL of substrate BS-2494 (diluted in assay buffer) is added, and the enzymatic reaction is allowed to proceed for 60 minutes, after which the fluorescence intensity is measured. The fluorescence intensity values are converted into percent inhibition by using control reactions (signal of uninhibited reactions is equivalent to 0% inhibition, and a reaction containing no enzyme is equivalent to 100% inhibition) and the following formula for transferring values:

$$y = 100\% - [Fl(x) - Fl(\min)]/[Fl(\max) - Fl(\min)],$$

where y is the %-inhibition at the antibody concentration x, Fl(x) is the fluorescence intensity measured at antibody concentration x, Fl(min) is the fluorescence intensity measured in the control reaction in absence of antibody and Fl(max) is the fluorescence intensity measured in the uninhibited control reaction. Data are analyzed using the program Origin 7.5SR6 (OriginLab Corporation, USA). IC50 values from averaged data are calculated using the logistics function:

$$y = A2 + (A1 - A2)/(1 + (x/IC50)^p),$$

where y is the %-inhibition at the antibody concentration x, A1 is the lowest inhibition value, and A2 the maximum inhibition value. The exponent, p, is the Hill coefficient.

Figure 6A:
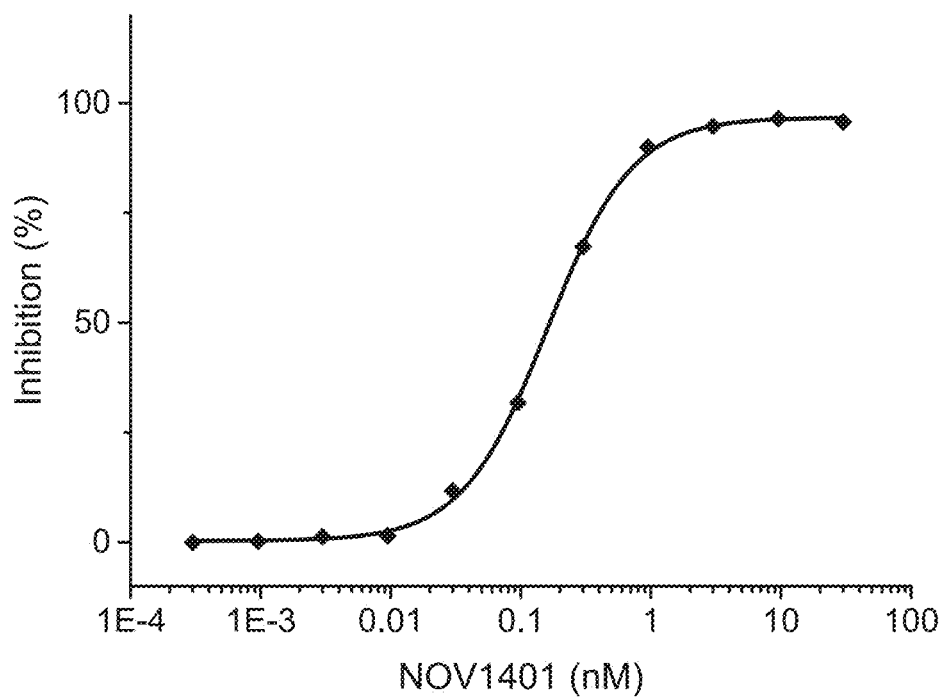
FIGS. 6A-C show compound response curves of an anti-FXI/FXIa antibody.

FIG. 6A shows a representative compound response curve of antibody NOV1401 inhibiting the enzymatic activity of full length human FXIa. The results show that NOV1401 inhibits the enzymatic activity of human full length FXIa in a concentration dependent manner (FIG. 6A). Fitting with the logistic fit model leads to an $IC_{50}$ value of approximately 160 pM.

Example 4

Anticoagulant Activity of Anti-FXIa Abs

The antithrombotic activity of the antibodies NOV1401 and NOV1090 were tested by using the activated partial thromboplastin time (aPTT) assay and the thrombin generation assay (TGA).

aPTT Assay:

Lyophilized normal human plasma 'Coagulation Control N' (reference no 5020050) was purchased from Technoclone GmbH (Vienna, Austria). It was pooled from citrated plasma of selected healthy donors. The clotting time obtained with this normal plasma reflects normal concentrations of the coagulation factors involved in clotting. The lyophilized plasma was stored at 4° C. Prior to its use, the plasma was re-suspended in 1 mL of distilled water by carefully rotating the vial and then keeping it for 10 minutes at RT.

The intrinsic pathway triggering reagent 'aPTT-s' (reference no TE0350) was purchased from SYCOmed (Lemgo, Germany) and contains phospholipid and silicate (colloidal) in a buffered solution (sodium chloride, polyethylene glycol 20000; sucrose, sodium azide). The solution was stored at 4° C.

Calcium Chloride (reference no C1016-500G; Sigma-Aldrich Chemie GmbH, Steinheim, Germany) was prepared in bi-distilled water at a stock concentration of 25 mM.

UltraPure Tris/HCl buffer at pH 7.5 (reference no 15567-027; Life Technologies Corporation, NY, USA) and Phosphate Buffered Saline (PBS, reference no P4417-100TAB; Sigma-Aldrich Chemie GmbH, Steinheim, Germany) were compound dilution.

3-[(3-Cholamidopropyl)dimethylammonio]-1-propane-sulfonate hydrate (CHAPS, reference no C3023-25G) and anhydrous Dimethyl sulfoxide (DMSO, reference no 276855-100ML) were purchased from Sigma-Aldrich Chemie GmbH (Steinheim, Germany).

The measurements of the clotting time were performed in an Amelung ball coagulometer model KC4A (purchased through SYCOmed, Lemgo, Germany), which is a semi-automated mechanical clot detection system. The system utilizes a special cuvette (reference no AI4000; SYCOmed) in which a stainless steel ball (reference no AI5000; SYCOmed) was placed.

The sample is added to the cuvette. After an appropriate incubation period, the cuvette is placed into the measuring well of the ball coagulometer. The measuring well rotates slowly causing the cuvette to rotate along its longitudinal axis. Because the cuvette is positioned at a slight angle, gravity and inertia always position the ball at the lowest point of the cuvette. Exactly opposite the ball-position is a magnetic sensor. With the addition of the trigger reagent, a timer is started. As coagulation takes place fibrin strands form in the reaction mixture. The fibrin strands pull the ball away from its inertia position that triggers an impulse in the magnetic sensor. This impulse electronically stops the timer. The pipetting scheme was as follows (Table 4a):

TABLE 4a

| Assay step | Solution | aPTT assay Volume [µL] |
|---|---|---|
| 1 | compound dilution or diluent | 50 |
| 2 | human blood plasma | 50 |
| 3 | aPTT-s reagent | 50 |
| 4 | | Incubate 3 minutes at 37° C. under rotation |
| 5 | 25 mM Calcium Chloride | 50 |
| 6 | | Immediately start the timer |
| 7 | | The timer stops when the clot is formed |

The samples were measured in duplicates at a temperature of 37° C. in the Amelung ball coagulometer.

Figure 6B:
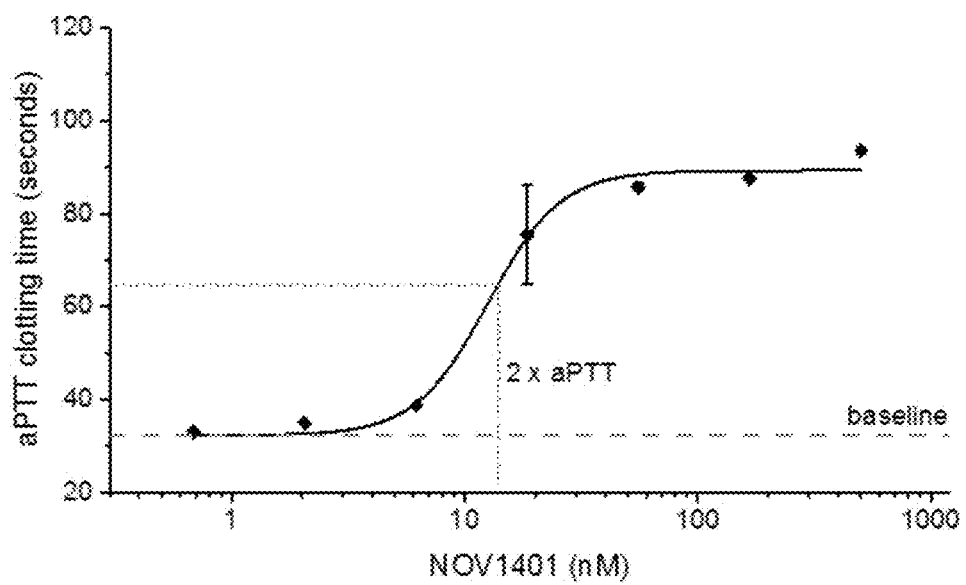

FIG. 6B shows a representative compound response curve of antibody NOV1401, leading to the concentration dependent prolongation of aPTT clotting times. The results suggest that NOV1401 leads to the prolongation of aPTT clotting times of human plasma in a concentration dependent manner. The aPTT clotting time is doubled compared to baseline at a NOV1401 concentration of approximately 14 nM. The $IC_{50}$ value was calculated to be approximately 13 nM.

Thrombin Generation Assay (TGA):

For the TGA lyophilized normal human plasma (Coagulation control N) was purchased from Technoclone GmbH, (reference number 5020040, Lot#1P37600) and reconstituted in distilled water in a the volume suggested by the manufacturer.

The substrate solution was prepared using the fluorogenic substrate Z-Gly-Gly-Arg-AMC from Technoclone GmbH (reference number 5006230, Lot#8F41600). Aliquots of the lyophilized substrate were kept at 4° C. The substrate was dissolved freshly in the volume of distilled water indicated on the vial 20 minutes prior its use in the assay. The reconstituted substrate solution contains the fluorogenic peptide at a concentration of 1 mM and $CaCl_2$ at a concentration of 15 mM.

Two different reagents TGA RD' (reference no 500622) and 'TGA RC low' (reference no 5006213) for triggering the intrinsic and the extrinsic pathway, respectively, were purchased from Technoclone GmbH (Vienna, Austria). The trigger reagent 'platelet poor plasma (PPP)-reagent low' was purchased from Thrombinoscope (TS31.00, Lot# PPL1409/01) and reconstituted in distilled water as indicated on the vial. PPP-reagent low' contains a mixture of phospholipids and tissue factor at very low concentration. The reagent was 8-fold diluted in 80 mM Tris/HCl at pH7.4, 0.05% (w/v) CHAPS immediately before use.

The samples were aliquoted and measured in 96 well black/clear bottom plates purchased from Costar (product no 3603). For automation transfer samples were placed in V-bottom 96 well plate (Costar, 3894) and transferred using a CyBio automation system (Analytik Jena US, Woburn, Mass., USA).

The reconstituted human blood plasma, trigger reagent 'PPP-reagent low' and substrate were pre-warmed for 10 minutes in a water bath at 37° C. Serial 1:3 antibody dilutions in PBS were prepared in a 96 well plate starting with a NOV1401 concentration of 5 µM (5× the highest final concentration of 1 µM) for a total of 8 dilutions. 222 µl of trigger reagent was mixed with 1108 µl of substrate solution to generate the 10+50 trigger reagent substrate mix. 80 µl per well was added into a V-bottom 96 well plate for later transfer using an automation system. The plate was kept at 37° C. The reagents were added according to the scheme given in Table 4b.

TABLE 4b

| Assay step | Solution | Volume [ul] |
|---|---|---|
| 1 | Antibody solutions (8 dilutions) | 20 |
| 2 | Plasma stock solution | 20 |
| | 5 minutes incubation at 37° C. in a thermomixer at 300 rpm. | |
| 3 | Trigger reagent/substrate mixture | 10 + 50 |

Trigger/substrate mixtures were transferred using automation. After adding the mixtures, excitation and emission at 360 nm at 460 nm, respectively, were recorded immediately using a Synergy Neo instrument (BioTek Instrument Inc., Winooski, Vt., USA). The samples were measured in duplicates at a temperature of 37° C. in the plate reader for 90 minutes at intervals of 55 seconds.

To generate peak thrombin concentration values data were processed using the TGA evaluation software file provided by Tech noclone. To generate plots for peak thrombin concentration vs antibody concentration data were fit using GraphPad software. These data were fit to a non-linear regression model in the GraphPad Prism5 software (GraphPad Software Inc., La Jolla, Calif., USA). The $IC_{50}$ value was determined using the built-in four-parameter dose-response curve equation (variable slope): y=Bottom+(Top−Bottom)/(1+10^((LogIC50−x)*HillSlope)) where y is the maximal concentration of thrombin formed at the inhibitor concentration, x, and top and bottom represent the concentration of thrombin without inhibitor and at the highest concentration of inhibitor, respectively.

Figure 6C:
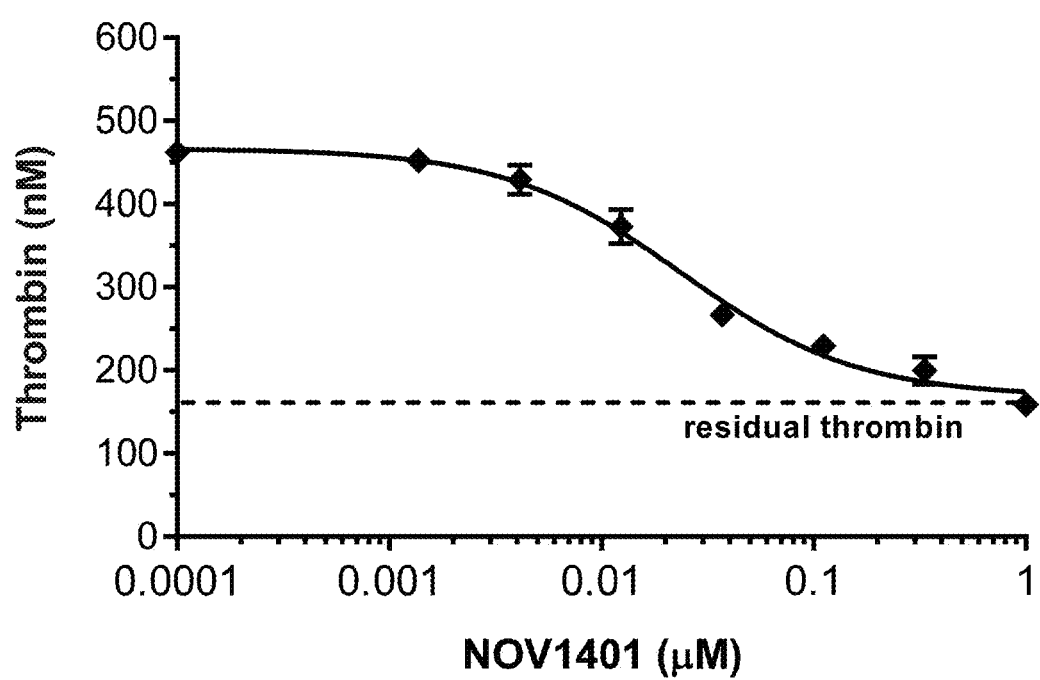

FIG. 6C shows a representative compound response curve of antibody NOV1401, displaying the concentration-dependent inhibition of thrombin generation in the TGA. An $IC_{50}$ value of 24 nM and a residual thrombin concentration of 159 nM (dotted line) were calculated for this compound response curve.

Example 5

Protein Expression, Complex Formation, Crystallization and Structure Determination of NOV1401 (Fab)-FXI (Catalytic Domain)

The structure of the Fab portion of the antibody NOV1401, obtained by papain cleavage in complex with the factor XI catalytic domain was obtained by cocrystallization at a resolution of 2.04 Å.

Protein Expression:

The expression construct for the FXI catalytic domain consisted of amino acid residues 388-625 (Swissprot P03951) with the unpaired cysteine, 0500, mutated to cysteine, with an N-terminal extension comprised of the amino acids MGSS (SEQ ID NO:49), an octa-histidine tag (SEQ ID NO: 50), a PreScission™ cleavage site followed by an enterokinase cleavage site. The construct was assembled by gene synthesis, cloned into the pET24a expression vector and expressed as inclusion bodies in E. coli strain BL21 (DE3) grown in LB-medium. The inclusion bodies were solubilized in 50 mM Tris/HCl pH 8.0, 6.0 M Guanidinium Chloride, 50 mM DTT for 2 hr., fully denaturing the recombinant protein. A large excess of refolding buffer (0.5 M Tris pH 8.0, 0.9 M Arginine HCl, 5 mM GSH, 0.5 mM GSSG, 1 mM EDTA was added rapidly to the IB solution to give a final protein concentration of 50 ug/ml and incubated at 4° C. for 5 days. Refolding and disulfide bridge formation were accomplished by dialysis with Buffer A (50 mM Tris pH 8.0) for three days.

The refolded protein was loaded onto an anion-exchange chromatography column containing Q-Sepharose® FF (GE Healthcare) equilibrated and washed with Buffer A. The unbound recombinant protein was collected from the flowthrough and wash fractions. The pH was adjusted to 7.4 by dialysis with 50 mM Tris pH 7.4 prior to removal of the N-terminal tag sequence using enterokinase (enterokinase: recombinant protein ratio 1:100, 2.5 h incubation time). The cleavage reaction was stopped by loading the sample onto a Benzamidine affinity column containing Benzamidine Sepharose 4 FF, high sub (GE Healthcare) equilibrated and washed with Buffer B (50 mM Tris pH 7.4, 0.5 M NaCl) and eluted with Buffer C (Buffer B containing 50 mM Benzamidine). The active FXI catalytic domain was loaded onto an XK 26/600 Superdex 75 size exclusion column (GE Healthcare) equilibrated with 20 mM Na-Acetate pH 5.3, 75 mM NaCl. The final protein concentration was 1.07 mg/ml.

The Fab portion of NOV1401 was obtained by papain cleavage of the IgG. Final Fab concentration was 11 mg/ml in PBS. The digestion was performed over night at 37° C. using papain (Roche Diagnostics 108 014; 10 mg/ml) added to the antibody at a 1:100 ratio (w/w) and in the presence of 1 mM cysteine (added to the original IgG solution) The digestion was stopped by addition of 50 µM of the specific papain inhibitor E64, (N—[N—(L-3-trans-carboxirane-2-carbonyl)-L-leucyl]-agmatine, and the digest was passed over a small protein A column (5 mL) in order to remove the Fc portion. The Fab was recovered in the flow-through, dialyzed against PBS, concentrated to its final concentration by ultrafiltration and sterile filtered (0.22 µm).

Complex Formation, Crystallization and Structure Solution:

The FXI catalytic domain and the Fab were mixed at equimolar ratio and concentrated to a final concentration of ca. 9 mg/ml.

The crystal used for data collection was obtained at 277K employing sitting drop vapor diffusion mixing 0.3 µL of reservoir solution (0.2 M ammonium-chloride, 20% PEG 3350), 0.2 µL Fab-FXI complex and 0.1 µL crystal seeds from crystals obtained in a first round of crystal screening.

For data collection crystals were directly flash frozen in liquid nitrogen. Data were collected at the Swiss Light Source beamline X10SA at a wavelength of 1.00002 Å using a Pilatus pixel detector (Dectris) at 100K. Data processing and scaling was performed with XDS and XSCALE (Kabsch, W. (2010) Acta Cryst. D66, 125-132). The crystal diffracted to a resolution of 2.04 Å with unit cell dimensions of a=191.27, b=53.22, c=65.164 alpha=90.0, beta=94.56, gamma=90.0 (Space group C2) with one copy of the complex per asymmetric unit.

The structure of the complex was solved by molecular replacement using structures of the FXI catalytic domain and a truncated Fab previously solved in-house as search models using PHASER (McCoy, A. J. et al. (2007) J. Appl. Cryst. 40, 658-674). Alternating cycles of refinement and rebuilding were performed using buster and coot rsp. (Bricogne, G. et al. (2010) BUSTER version 2.9. Cambridge, United Kingdom: Global Phasing Ltd.; Emsley, P. and Cowtan, K. (2004). Acta Crystallogr. D60, 2126-2132). The data collection and refinement statistics are summarized in Table 5.

TABLE 5

Data collection and refinement statistics

| Data collection | |
|---|---|
| Space group | C2 |
| Cell dimensions | |
| a, b, c (Å) | 191.27, 53.22, 65.16 |
| α, β, γ (°) | 90, 94.56, 90 |
| Resolution (Å) | 64.96-2.04 (2.09-2.04) |
| $R_{sym}$ | 0.099 (0.571) |
| I/σI | 10.8 (2.7) |
| Completeness (%) | 95.9 (98.4) |
| Redundancy | 3.2 |
| Refinement | |
| Resolution (Å) | 64.96-2.03 |
| No. reflections | 40088 |
| $R_{work}/R_{free}$ | 0.217/0.282 |

TABLE 5-continued

Data collection and refinement statistics

| No. atoms | |
|---|---|
| Protein | 5071 |
| Water | 413 |
| R.m.s. deviations | |
| Bond lengths (Å) | 0.01 |
| Bond angles (°) | 1.19 |

*Values in parentheses are for highest-resolution shell.

Description of the Structure:

The structure reveals the binding epitope of the antibody NOV1401 binds to the active site surface with the heavy chain CDR3 loop covering portions of the S3, S2, S1-beta and S1' subsites. The adjacent heavy chain CDR1 and CDR2 loops induce conformational changes in the FXI 145- and 220-loops (chymotrypsin numbering). In addition, four N-terminal FXI residues as well as residues surrounding Asp189 become disordered; both are portions with key functions for catalytic activity of FXI. The conformational change of the 145-loop leads to occlusion of the S1 pocket by Arg144 and of the S2' subsite by Tyr143. Antibody binding hence leads to an inhibited conformation of FXI through multiple mechanisms.

The observed inhibited form shares features described for the full-length zymogen form of FXI (PDB 2F83). The portions of the FXI catalytic domain that have changed conformation or have become disordered as a result of antibody binding are disordered in the zymogen also. This explains the strong binding of NOV1401 also to the zymogen form of FXI.

Figure 4A:
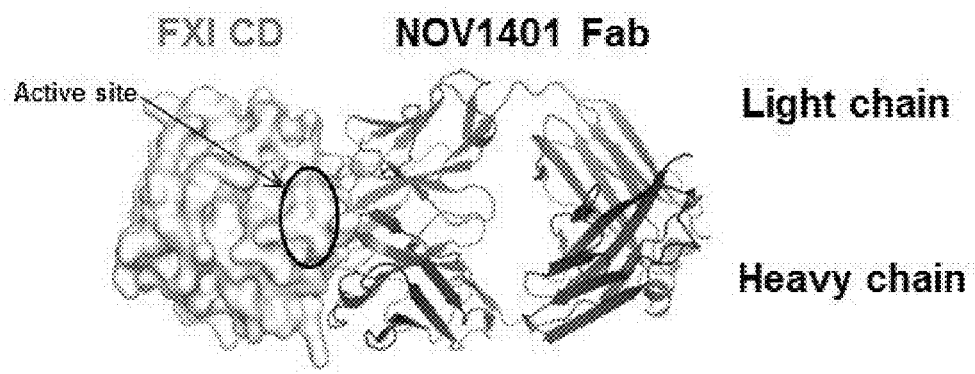
FIGS. 4A-B show the X-ray structure of the Fab of the NOV1401 antibody of the invention bound to FXI.
Figure 4B:
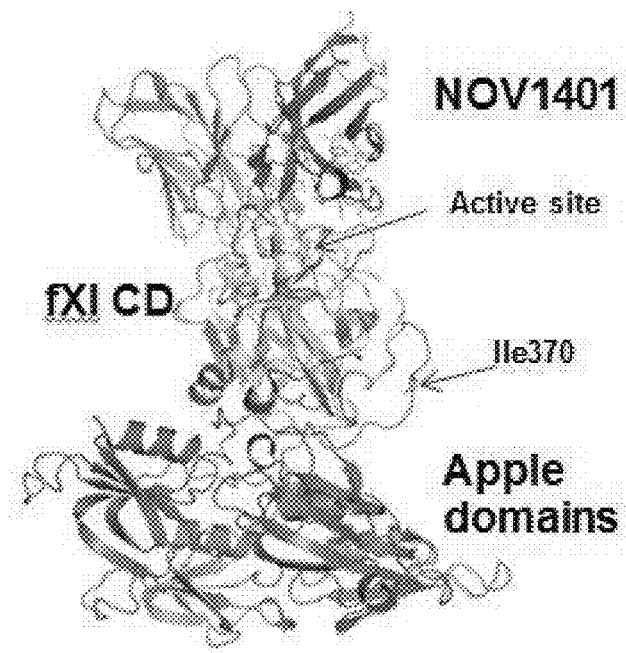
Figure 5A:
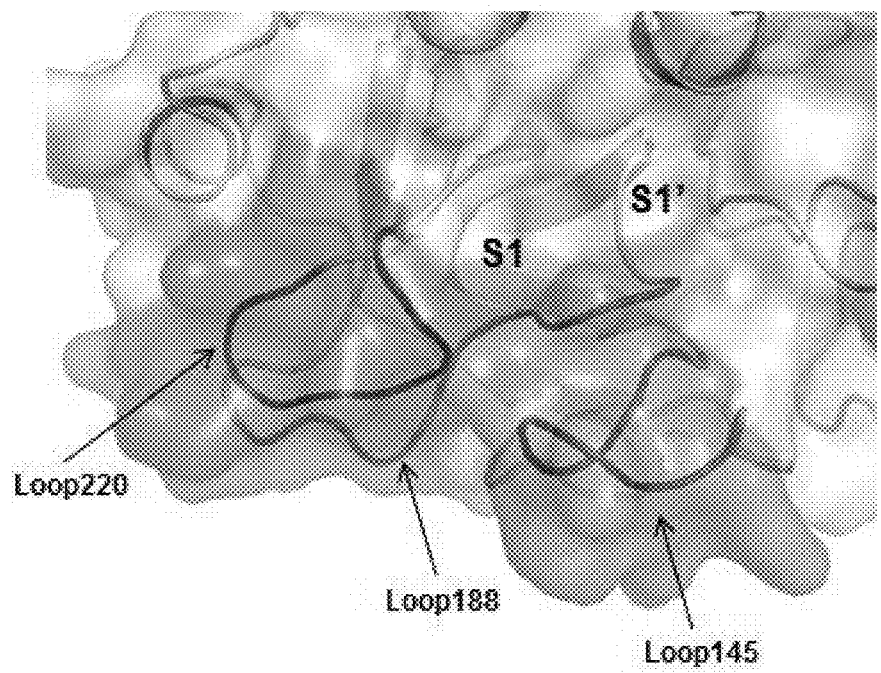
FIGS. 5A-B shows structural changes of FXIa upon NOV1401 Fab binding.
Figure 5B:
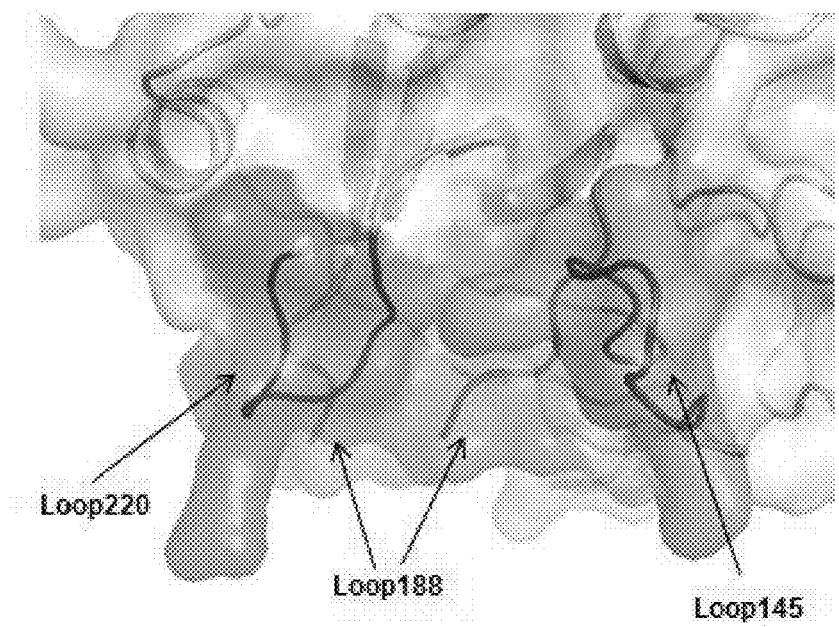

Our finding that NOV1401 does not inhibit FXI zymogen activation is in agreement with the distance of the binding epitope from the FXIa zymogen activation cleavage site. NOV1401 binds both to FXI and FXIa. The X-ray structure of the Fab-FXI CD complex reveals a unique binding mode and mechanism of inhibition of FXIa. NOV1401 binds to the active site of FXIa (FIG. 4) and induces conformational changes of the four N-terminal residues and catalytic domain loops leading to an inactive conformation. This inactive conformation shares features with the inactive catalytic domain structure in the zymogen (FIG. 5) providing an explanation how both FXI and FXIa can be bound with high affinity by NOV1401. For example, three catalytic site loops (e.g., look 220, loop 188, and loop 145) that are disordered in the zymogen structure are also disordered or shifted in the NOV1401 Fab-FXI CD complex structure, and an N-terminal salt bridge observed in the active confirmation is absent in both the zymogen and NOV1401 Fab-FXI CD complex structures (Table 6). Hence, NOV1401 seems to induce conformational changes within the CD leading to an inactive, zymogen-like conformation.

TABLE 6

Structural features of FXIa CD, FXIa CD complexed with NOV1401 and FXI-zymogen (CD):

| | FXIa CD | NOV1401-FXI CD complex | FXI zymogen |
|---|---|---|---|
| Salt-bridge Ile16-Asp194 | + | − | − |
| Loop145 | ordered | shifted | disordered |
| Loop188 | ordered | disordered | disordered |
| Loop220 | ordered | shifted | disordered |

Example 6

X-ray Structure Based Epitope Mapping

Residues of FXI in contact with the Fab were analyzed using AREAIMOL (Briggs, P. J. (2000) CCP4 Newsletter No. 38), determining the residue surface area difference when calculated without bound Fab and in complex with the Fab, described as follows in Table 7 and Table 8a (Swissprot numbering):

TABLE 7

FXI Epitope
Epitope (Underlined: light chain & heavy chain contacts):

| Light Chain Contacts | Heavy Chain Contacts |
| --- | --- |
| Pro410 | Leu415 |
| Arg413 | Cys416 |
| His431 | His431 |
| Tyr434 | Cys432 |
| Gly435 | Tyr434 |
| Glu437 | Tyr472 |
| Tyr472 | Met474 |
| Lys473 | Ala475 |
| Met474 | Glu476 |
| Glu476 | Tyr521 |
| Tyr521 | Arg522 |
| Leu524 | Lys523 |
| Arg525 | Leu524 |
| Asp526 | Arg525 |
| His552 | Asp526 |
|  | Lys527 |
|  | Arg548 |
|  | Ser575 |
|  | Ser594 |
|  | Trp595 |
|  | Gly596 |
|  | Glu597 |
|  | Arg602 |
|  | Glu603 |
|  | Arg604 |

The FXI epitope is formed of the following residues: Pro410, Arg413, Leu415, Cys416, His431, Cys432, Tyr434, Gly435, Glu437, Tyr472-Glu476, Tyr521-Lys527, Arg548, His552, Ser575, Ser594-Glu597, Arg602-Arg604.

TABLE 8a

| Residues of FXI In Contact with NOV1401 (Epitope) | |
| --- | --- |
| Residue | Area Difference |
| PRO A 410 | −11.0 |
| ARG A 413 | −36.3 |
| LEU A 415 | −3.6 |
| CYS A 416 | −2.1 |
| HIS A 431 | −36.5 |
| CYS A 432 | −0.6 |
| TYR A 434 | −108.1 |
| GLY A 435 | −31.6 |
| GLU A 437 | −3.7 |
| TYR A 472 | −13.0 |
| LYS A 473 | −40.1 |
| MET A 474 | −73.1 |
| ALA A 475 | −12.0 |
| GLU A 476 | −40.4 |
| TYR A 521 | −18.5 |
| ARG A 522 | −46.6 |
| LYS A 523 | −74.7 |
| LEU A 524 | −147.1 |
| ARG A 525 | −212.6 |
| ASP A 526 | −17.7 |
| LYS A 527 | −0.2 |
| ARG A 548 | −11.6 |
| HIS A 552 | −4.0 |
| SER A 575 | −7.7 |
| SER A 594 | −8.7 |
| TRP A 595 | −20.9 |
| GLY A 596 | −17.5 |
| GLU A 597 | −49.0 |
| ARG A 602 | −18.5 |
| GLU A 603 | −2.0 |
| ARG A 604 | −41.0 |

X-Ray Epitope Mapped on the Catalytic Domain Sequence (Residues Forming the Epitope Bolded and Underlined):

(SEQ ID NO: 51)

```
388
IVG

391
GTASVRGEWP WQVTLHTTSP TQRHLCGGSI IGNQWILTAA HCFYGVESPK

441
ILRVYSGILN QSEIKEDTSF FGVQEIIIHD QYKMAESGYD IALLKLETTV

491
NYTDSQRPIC LPSKGDRNVI YTDCWVTGWG YRKLRDKIQN TLQKAKIPLV

541
TNEECQKRYR GHKITHKMIC AGYREGGKDA CKGDSGGPLS CKHNEVWHLV 591                                     625
GITSWGEGCA QRERPGVYTN VVEYVDWILE KTQAV
```

Table 8b shows the residues of the antibody in contact with FXI (paratope).

TABLE 8b

Residues of NOV1401 In Contact with FXI (Paratope).
L, light chain; H, heavy chain

| Residue difference | Area |
|---|---|
| SER L 27 | −1.80 |
| GLY L 30 | −5.00 |
| SER L 31 | −52.60 |
| ASN L 32 | −21.00 |
| ASP L 33 | −22.00 |
| TYR L 50 | −36.00 |
| LYS L 51 | −54.20 |
| TYR L 53 | −41.40 |
| ASN L 54 | −25.50 |
| LYS L 67 | −6.90 |
| TRP L 92 | −44.30 |
| GLN L 94 | −72.00 |
| ARG L 95 | −5.70 |
| PHE L 97 | −54.70 |
| ASP L 98 | −2.70 |
| VAL L 99 | −0.10 |
| PHE H 27 | −2.00 |
| THR H 28 | −20.50 |
| SER H 30 | −13.80 |
| THR H 31 | −78.90 |
| ALA H 33 | −10.80 |
| TRP H 47 | −12.70 |
| SER H 52 | −2.20 |
| TYR H 59 | −62.00 |
| TYR H 60 | −0.80 |
| GLU H 99 | −1.70 |
| SER H 101 | −51.30 |
| TYR H 102 | −116.60 |
| LEU H 103 | −175.00 |
| TYR H 104 | −140.20 |
| SER H 105 | −1.30 |

Example 7

Effect of FXI Antibody on FeCl$_3$-induced Thrombosis in Mice

Mice deficient in FXI (FXI$^{-/-}$ mice) on a C57Bl background were bred at Novartis (E. Hanover, N.J.) and used to assess the anti-thrombotic efficacy of NOV1401. When reconstituted intravenously with human FXI (hFXI), these mice acquire a wild-type thrombophilic phenotype when exposed to a thrombogenic stimulus. In the studies herein, thrombosis was induced in the carotid artery by applying ferric chloride (FeCl$_3$) to the surface of the artery.

NOV1401 was injected as a bolus through the jugular vein of anesthetized mice 15 minutes prior to the induction of thrombosis. Doses of antibody ranged from 0.24 mg/kg-0.47 mg/kg. The FXI$^{-/-}$ mice were reconstituted with human FXI by injecting 0.47 mg/kg human FXI via the jugular vein 10 minutes prior to the FeCl$_3$ challenge. Two 1 mm×1.5 mm pieces of filter paper saturated with 3.5% FeCl$_3$ were then applied to opposite sides of the carotid artery, in contact with its adventitial surface, and removed 3 minutes afterward, followed by thorough washing with saline. Blood flow through the carotid artery was measured with a Transonic flow probe. Baseline blood flow was obtained for 5 minutes prior to FeCl$_3$ application and then for 30 minutes after application of FeCl$_3$ (i.e., during the thrombogenic period). At the end of the experiment blood was sampled from the vena cava into syringes containing 3.8% sodium citrate, plasma was prepared and subjected to an aPTT assay.

Figure 1B:
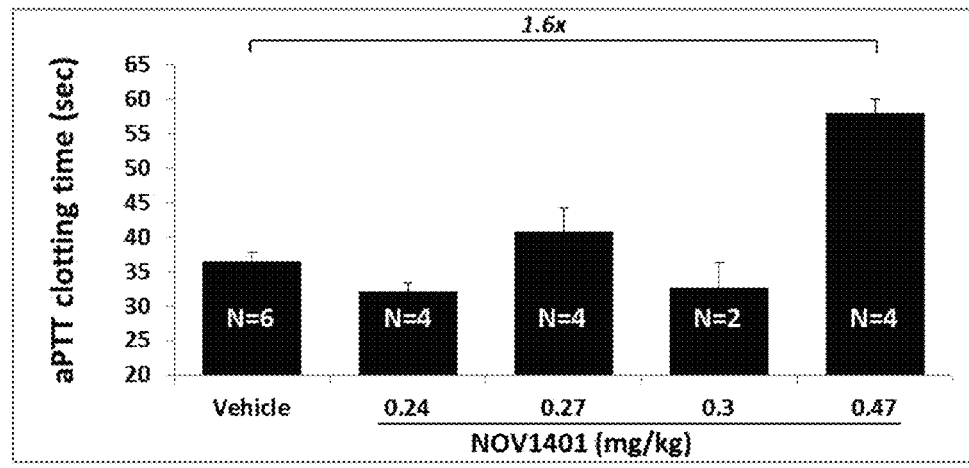
Figure 1C:
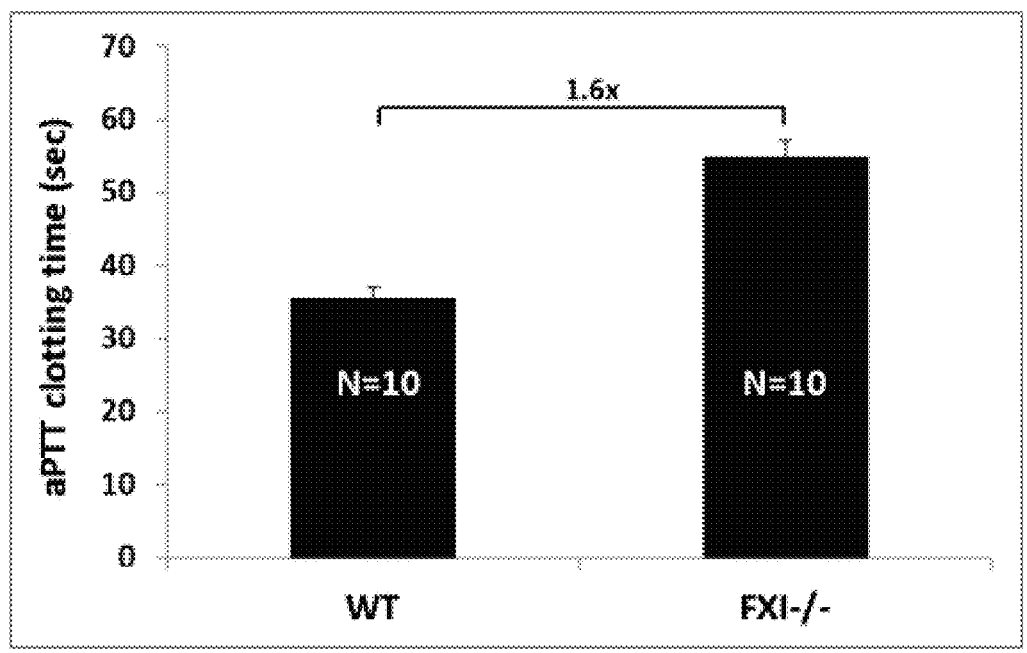

FIG. 1A shows the effect of NOV1401 on FeCl$_3$-induced thrombosis in FXI$^{-/-}$ mice reconstituted with human FXI (humanized FXI mouse model). FIG. 1B shows the effect of NOV1401 on aPTT in the same mouse model. FIG. 1C shows aPTT prolongation in FXI$^{-/-}$ mice in comparison to wild-type mice.

NOV1401 fully inhibited FeCl$_3$-induced thrombus formation in hFXI-reconstituted FXI$^{-/-}$ mice (FIG. 1A) starting at 0.24 mg/kg. A steep dose response was observed, likely reflecting a stoichiometric all-or-none antithrombotic response. The aPTT was prolonged to 1.6 fold above vehicle controls in the high dose group (FIG. 1 B), corresponding to the same level of prolongation by genetic depletion of FXI (FIG. 1 C), i.e., maximal effect. These results show that NOV1401 has anti-thrombotic activity in mouse FeCl$_3$ thrombosis model.

Example 8

Effects of FXI Antibody on Free FXI and aPTT in Cynomolgus Monkeys

To evaluate the pharmacokinetic (PK) profile and pharmacological effects of an anti-FXI/FXIa antibody, such as NOV1401, the antibody was administered via subcutaneous (s.c.) or intravenous (i.v.) injections to cynomolgus monkeys in a rising dose study.

The anticoagulant effect of NOV1401 was characterized in cynomolgus monkeys by testing the antibody's ability to prolong aPTT and reduce free FXI (FXI$_f$) levels after a single intravenous (N=2) or subcutaneous (N=2) dose of 3 mg/kg. A second dose of 10 mg/kg was administered to all animals followed by a third dose of 30 mg/kg to determine if the effects observed at 3 mg/kg can be potentiated by higher doses. These results show that NOV1401 has sustained anticoagulant activity in cynomolgus monkeys. The pharmacodynamics (PD) of NOV1401, characterized by its anticoagulant effect as determined by aPTT and FXI$_f$ levels, were then compared to the PK profile. The comparison indicates that there is a good PK/PD correlation.

Animals were dosed either i.v. (N=2) or s.c. (N=2) with NOV1401 on study day 1 at 3 mg/kg, day 85 at 10 mg/kg and day 114 at 30 mg/kg. Blood samples were collected into sodium citrate coagulation tubes at 15 min and 2 hours post-dose for i.v. dosed animals, and for all animals at pretest, 6, 24, 48, 72 and 96 hours post-dose (days 1, 85 and 114) and at 8, 11, 15, 18, 22, 25, 29, 32, 36, 39, 43, 46, 50, 53, 57, 60, 64, 66, 71, 75 and 78 days post-dose (day 1 only Blood was also collected on days 92, 95, 99, 102, 107, 110, 121, 124, 128 and prior to dosing on day 114. All blood samples were centrifuged; plasma samples were obtained and frozen at approximately −70° C. or below.

Total NOV1401 plasma concentrations were measured by standard methods for human IgG detection by ELISA using a sandwich immunoassay with a mouse anti-human-IgG monoclonal antibody as capture antibody and a goat anti-human-IgG with an HRP label as detection antibody.

For free FXI measurements in plasma samples that contain both FXI and NOV1401, unbound FXI was captured with immobilized NOV1401 and FXI already complexed with NOV1401 was washed away. Plate-bound FXI was then detected with a mouse Fc containing antibody 14E11, a monoclonal antibody that binds to the A2 domain of FXI and has been described in the literature (Cheng, et al. Blood, 116:3981-3989, 2010). The very high affinity of NOV1401 to both FXI and FXIa and the different binding sites for NOV1401 and the detection antibody 14E11 allowed an accurate determination of free FXI.

ELISA plates (384-Well LUMITRAC™ 600 HB) were coated with NOV1401 (5 µg/mL in PBS) for binding of free FXI. After blocking (milk blocker: KPL #50-82-01, 1:20 dilution) and washing the plates with wash buffer (PBS; 0.05% Tween 20), plasma samples diluted 1:40 in assay buffer (50 mM HEPES at pH 7.4, 125 mM NaCl, 5 mM $CaCl_2$, 5 mM EDTA and 0.05% (w/v) CHAPS) were incubated at RT for 30 min. and washed 3× with wash buffer. The detection antibody 14E11 was added at 1 µg/mL in dilution buffer (1.7 mM sodium phosphate monobasic, 8.1 mM sodium phosphate dibasic heptahydrate, 0.15 M sodium chloride, 0.7% Triton X-100, and 0.1% sodium azide, pH 7) containing 0.7% casein. After washing the plates with wash buffer, a secondary detection antibody, peroxidase-labeled anti-mouse IgG (Sigma #A5278), was added at 0.5 µg/mL in dilution buffer containing 0.4% casein. After washing the plates in wash buffer, 50 µL peroxidase chemiluminescent substrate solution (LumiGLO, KPL #54-61-01) was added and the luminescence signal was read immediately on multi-mode microplate reader (SPECTRAMAX M5E). The free FXI concentration in each sample was determined using a standard curve generated with human FXI (zymogen) from Enzyme Research Laboratories (Catalog #HFXI 1111) starting from 100 nM FXI with a dilution factor of 2 and 22 dilution steps. The lower limit of quantification (LLOQ) was 0.24 nM FXI taking into account the 1:40 dilution before measurement.

Figure 2A:
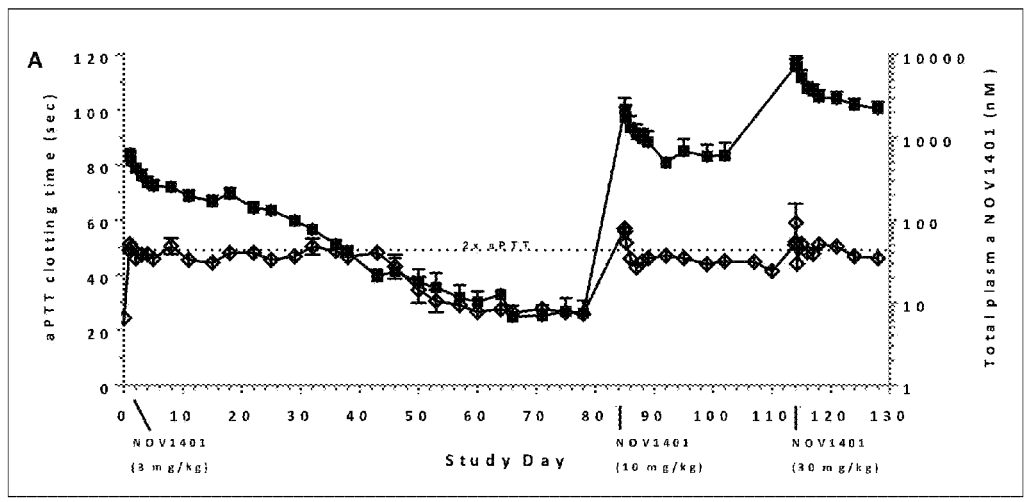
FIGS. 2A-B show the effect of multiple intravenous (i.v.) (A; N=2) or subcutaneous (s.c.) (B; N=2) doses of 3 mg/kg, 10 mg/kg and 30 mg/kg NOV1401 on aPTT (diamonds) and relationship to total plasma NOV1401 levels (squares) in cynomolgus monkeys. A single dose of 3 mg/kg led to ~2×aPTT that was maintained for 5-6 weeks. All doses tested prolonged aPTT to a similar extent, and the higher doses tested did not seem to increase the magnitude of aPTT prolongation observed at the 3 mg/kg dose.
Figure 2B:
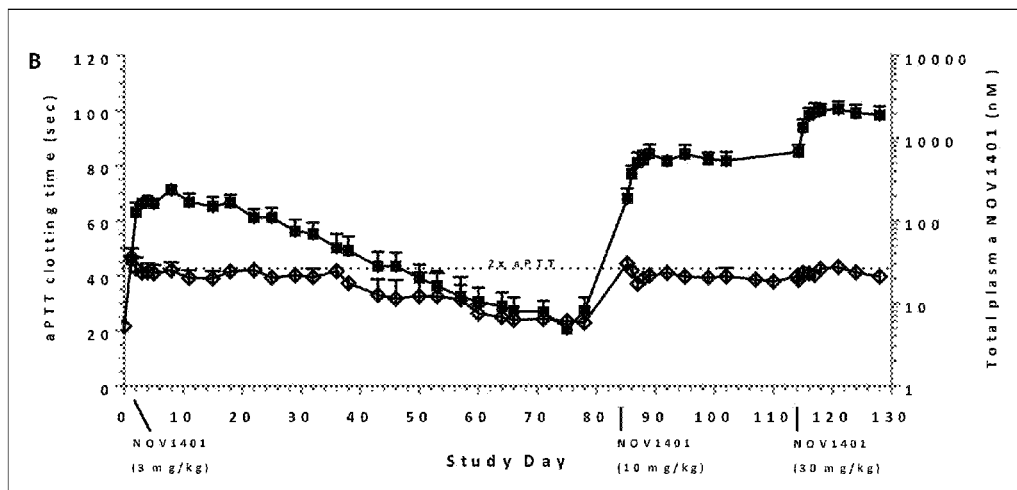
Figure 3A:
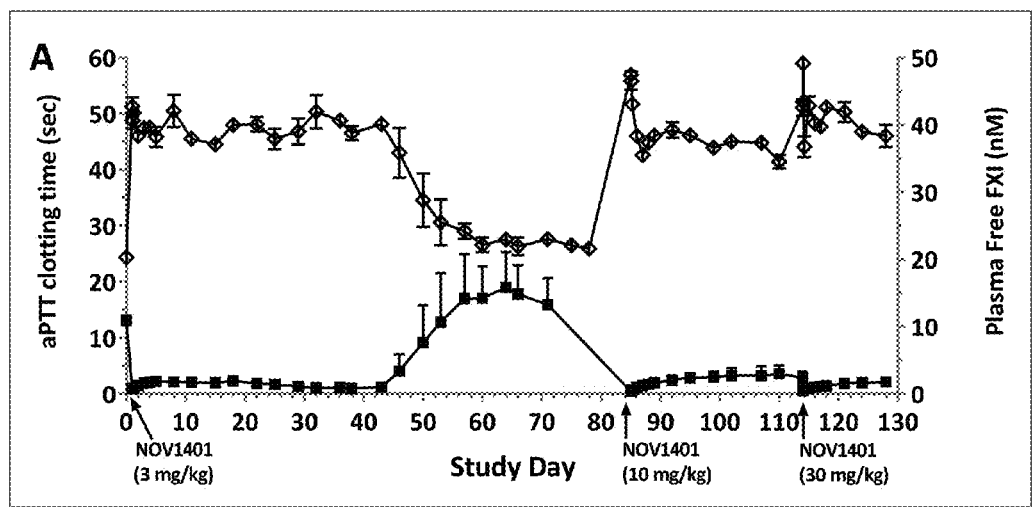
FIGS. 3A-B show the effect of multiple i.v. (A; N=2) or s.c. (B; N=2) doses of 3 mg/kg, 10 mg/kg and 30 mg/kg NOV1401 on plasma free FXI (squares) and relationship to aPTT (diamonds) in cynomolgus monkeys. A single dose of 3 mg/kg reduced free FXI by approximately 90% for 5-6 weeks. All doses tested reduced free FXI to a similar extent, and the higher doses tested did not seem to increase the magnitude of reduction of free FXI observed at the 3 mg/kg dose.
Figure 3B:
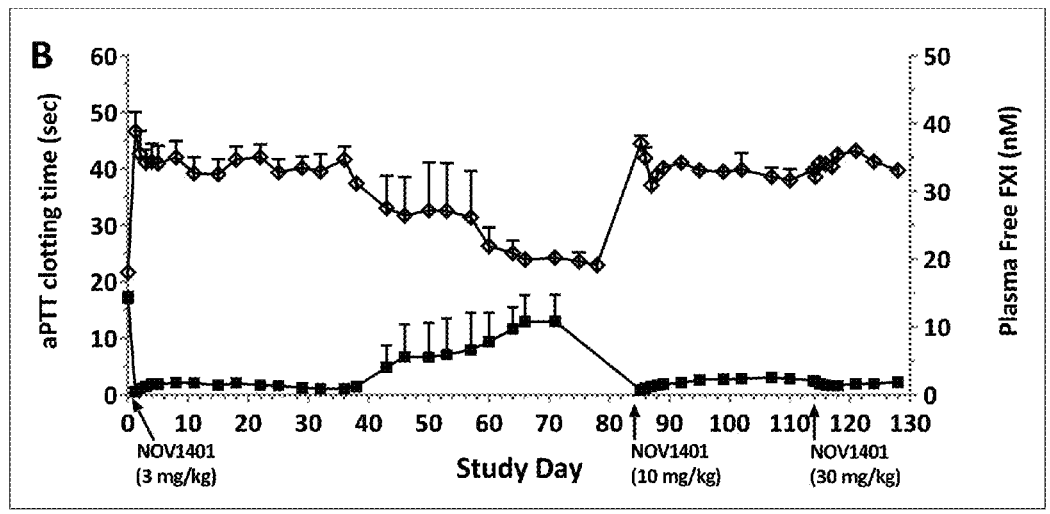

Plasma samples from all time points were subjected to aPTT analysis and aPTT results were compared to total plasma NOV1401 concentration and free FXI levels. FIGS. 2A and 2B show changes of aPTT clotting times in relationship to total plasma NOV1401 levels for i.v.- and s.c.-dosed animals. FIGS. 3A and 3B show changes of aPTT clotting times in relationship to free FXI levels for i.v.- and s.c.-dosed animals.

For i.v.-administered NOV1401, the highest plasma total NOV1401 levels were observed at 15 min. post-dose (FIG. 2A). At this time the aPTT was approximately doubled versus baseline in both animals and remained at this level for an average of 5-6 weeks. The mean aPTT prolongations from 15 min. post-dose over the measurements preceding the decline toward baseline were 2.0±0.02 times and 1.9±0.03 times for each animal.

By day 85, prior to administration of a second dose, aPTT had reached baseline levels and NOV1401 plasma concentrations had fallen below 10 nM. A second dose of 10 mg/kg was administered on day 85 increasing the plasma concentration of total NOV1401 by about at least 3-fold and resulting in aPTT prolongation similar to what was observed after the first dose. A third dose of 30 mg/kg was administered on day 114 while aPTT was still prolonged, and did not result in any significant additional aPTT prolongation, despite another at least 3-fold increase in total NOV1401 plasma concentration (FIG. 2A). Therefore, NOV1401 doses higher than 3 mg/kg achieved comparable aPTT prolongation as the 3 mg/kg dose, and did not seem to increase the magnitude of aPTT prolongation. As expected, s.c. administration of NOV1401 resulted in a slower rise in aPTT than with i.v. administration, but the extent of prolongation was comparable to that in the i.v. group (FIG. 2B). The aPTT was prolonged versus baseline for an average of 5-6 weeks in the two animals. Mean aPTT fold prolongations were similar to those of i.v.-treated animals: 2.0±0.03 and 1.8±0.02 from 6 hrs. post-dose through the measurements preceding the decline toward baseline. As in the i.v, administering higher doses did not lead to higher aPTT responses despite higher NOV1401 plasma exposures.

The results in FIGS. 2A-2B demonstrate that NOV1401 prolongs aPTT in cynomolgus monkeys.

The mean baseline plasma $FXI_f$ concentration was 10.9±0.3 nM in the i.v. group and fell rapidly (by 15 min.) upon injection of NOV1401 (FIG. 3A). Plasma $FXI_f$ levels remained low until total NOV1401 plasma levels dropped to between 15 nM-25 nM (FIG. 2A, FIG. 3A). In the s.c. group, the mean baseline $FXI_f$ concentration was 14.3±1.0 nM. $FXI_f$ was sharply lower vs baseline by 6 hrs. post-treatment (FIG. 3B), and remained low until plasma NOV1401 levels declined to between 15 nM-25 nM (FIG. 2B, FIG. 3B). $FXI_f$ dropped again sharply after the second dose at 10 mg/kg in all animals and remained low until the end of the study. The two higher doses did not further reduce $FXI_f$ relative to baseline.

In all treated animals, the drop and recovery of $FXI_f$ levels were temporally and inversely related to NOV1401-induced prolongation of aPTT, confirming that NOV1401 inhibits the function of the intrinsic coagulation pathway (prolongs aPTT) by lowering $FXI_f$.

These results (e.g., FIGS. 3A and 3B) demonstrate that NOV1401 lowers plasma $FXI_f$ levels in cynomolgus monkeys. In the cynomolgus monkey studies, no evidence of excessive bleeding was observed at the venipuncture sites or by gross observations at necropsy. Moreover, occult blood was not detected in stools throughout the study.

Figure 7A:
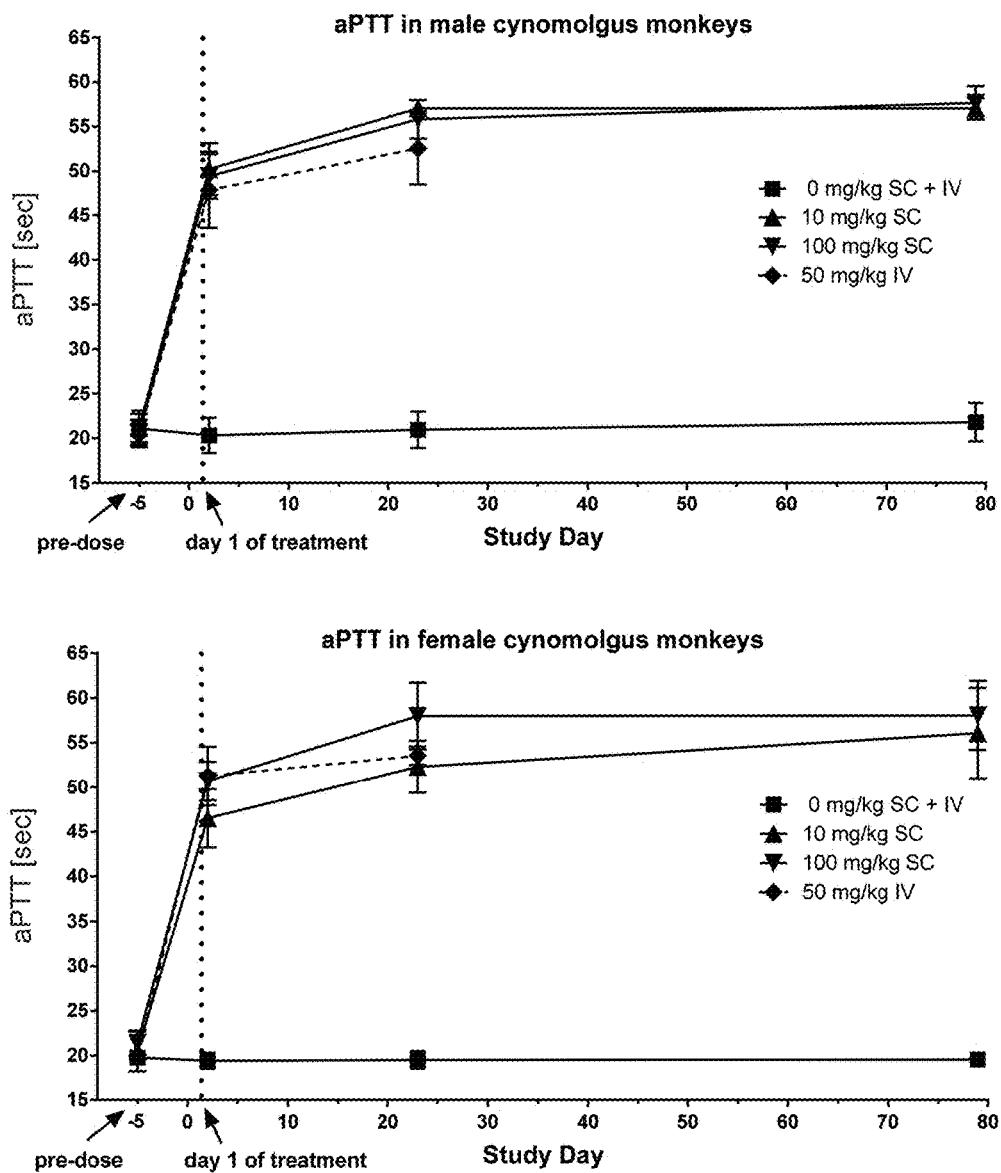
FIGS. 7A-B show the effect of weekly NOV1401 doses of 10 mg/kg (N=3) and 100 mg/kg (N=5) s.c. for 13 weeks (14 doses) or at 50 mg/kg (N=3) i.v. for 4 weeks (5 doses) on aPTT and FXI activity (FXI:C).
Figure 7B:
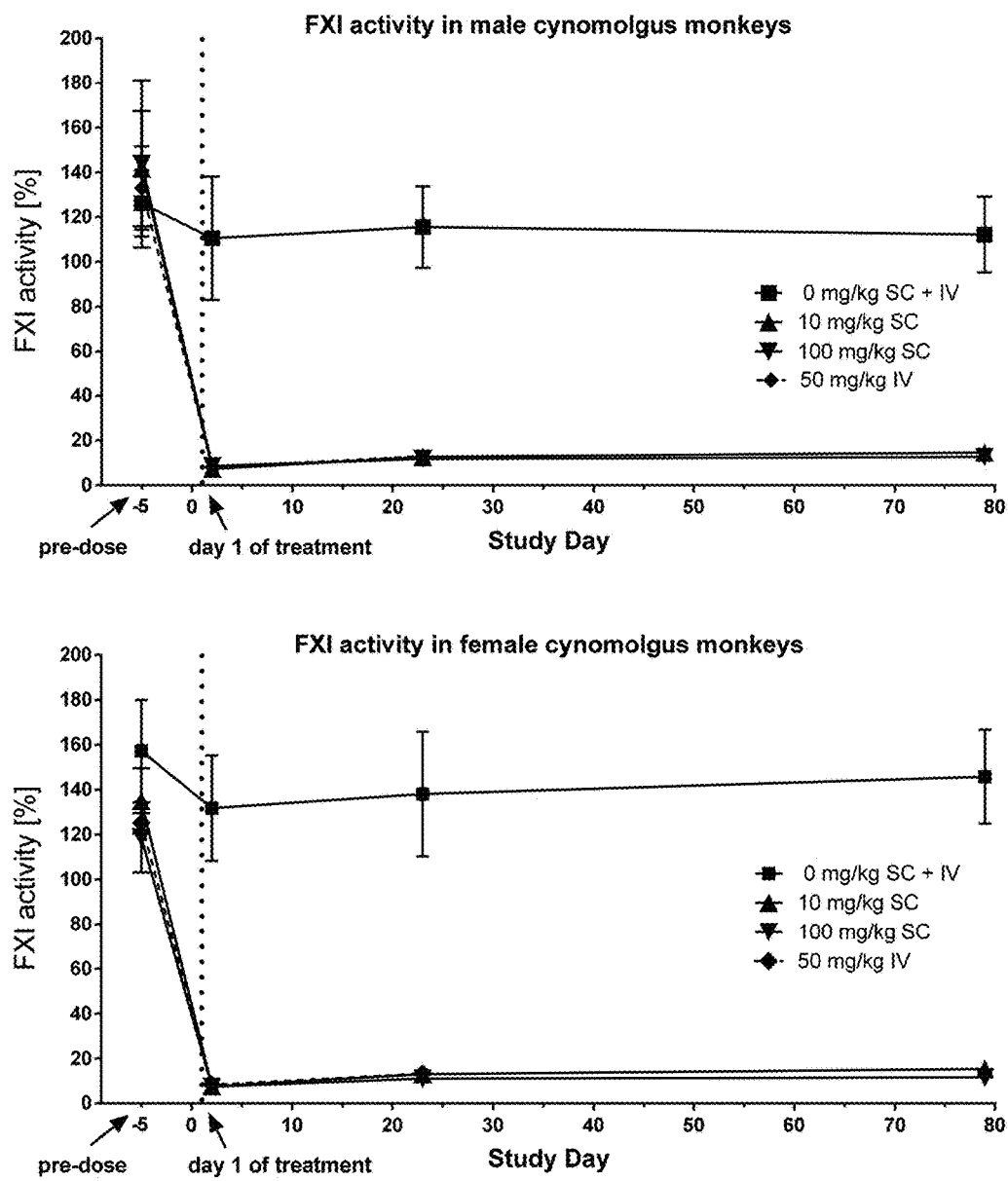

A sustained anticoagulant effect of NOV1401 was also observed in a 13-week s.c./4-week i.v. repeat dose toxicity study in cynomolgus monkeys. In this study, NOV1401 was administered weekly at doses of 10 mg/kg (N=3, male and female combined) and 100 mg/kg (N=5, male and female combined) s.c. for 13 weeks (14 doses) or at 50 mg/kg (N=3, male and female combined) i.v. for 4 weeks (5 doses). The control group (N=5, male and female combined) received vehicle for 13 and 4 weeks s.c. and i.v., respectively. FXI:C was assessed by measuring clotting time of cynomolgus monkey plasma samples in the presence of human FXI deficient plasma (one-stage aPTT). aPTT and FXI:C were measured on study days 2, 23, and 79 for the s.c. groups and on days 2 and 23 for the i.v. group. Across all animals and all treatment groups, an aPTT prolongation of 2.1- to 3-fold was observed (FIG. 7A). The effect was sustained throughout the dosing phase of the study and no dose-dependency was observed similar to the observation in the previous rising dose study. FXI:C was reduced across animals and treatment groups by 88-95% and remained at these levels throughout the dosing phase of the study (FIG. 7B). The effect on FXI:C was also dose-independent over these doses.

No evidence of macroscopic or microscopic indications of bleeding, including excessive bleeding, was observed at the venipuncture sites (including s.c. and i.v. injection and blood sampling sites) or by gross observations at necropsy. Moreover, occult blood was not detected in stools at the end of the study. In addition, no mortality occurred and there were no test article-related effects on clinical signs, body weight, food consumption, ophthalmologic and electrocardiographic parameters, hematology, clinical chemistry, or urinalysis. No target organs of toxicity were identified.

Increased thyroid weights were observed in males at 100 mg/kg s.c. However, the toxicological significance of this finding is inconclusive, since there were no histologic correlates. There was large variability of thyroid weights amongst the animals, and the finding was present only in one sex. Microscopically, dose-dependent fibrosis at s.c. injection sites in both sexes was observed at 10 and 100 mg/kg/week s.c. These findings were not considered adverse.

No significant toxicity findings were observed in single rising dose or repeat dose general toxicity studies in cynomolgus monkeys up to 13 weeks. Therefore, the highest s.c. dose level administered in the 13-week GLP toxicity study (100 mg/kg/week) was defined as the NOAEL.

Example 9

Pharmacokinetics in Cynomolgus Monkey—Single Dose

Cynomolgus monkeys (female, N=2) were administered a single 3 mg/kg dose of NOV1401 either i.v. or s.c. and observed until plasma $FXI_f$ concentrations and aPTT returned to pre-dose values. The animals were then administered a single 10 mg/kg dose of NOV1401 either i.v. or s.c. followed 2 weeks later by a 30 mg/kg dose either i.v. or s.c. and another 2-week observation period. The PK of NOV1401 was assessed by measuring total NOV1401. The exposure to total NOV1401, as measured by either the maximum observed total NOV1401 concentration ($C_{max}$) or the area under the total NOV1401 concentration-time curve ($AUC_{0-14d}$), was comparable between the individual animals in each group. Exposure ($C_{max}$ or $AUC_{0-14d}$) was approximately dose-proportional for each dosing route (Table 9). $C_{max}$ was approximately 3-fold higher in the i.v. group than in the s.c. group. However, plasma total NOV1401 concentrations were similar in both groups following the initial distribution phase. The terminal elimination half-life ($t_{1/2}$) was estimated for each animal using a two-compartment model following administration of the 3 mg/kg dose. The $t_{1/2}$ ranged from 14-15 days (N=2). The absolute bioavailability following s.c. injection ranged from 61-66% (3 dose levels). Anti-NOV1401 antibodies were not detected after either i.v. or s.c. administration in any animals.

TABLE 9

Mean pharmacokinetic parameters following single (rising) dose administration in female cynomolgus monkeys

| Dose (mg/kg) | Route | $t_{max}$ (hr)* | $C_{max}$ (μg/mL) | $AUC_{0-14\,d}$ (μg · d/mL) |
|---|---|---|---|---|
| 3 | i.v. | 0.25 | 96.0 | 544 |
| 3 | s.c. | 168 | 36.0 | 360 |
| 10 | i.v. | 0.25 | 325 | 1,810 |
| 10 | s.c. | 132 | 101 | 1,160 |
| 30 | i.v. | 1.08 | 1,170 | 6,770 |
| 30 | s.c. | 132 | 344 | 4,140 |

*$t_{max}$ is reported as median value.

Example 10

Toxicokinetics in Cynomolgus Monkey—Repeat Dose

Cynomolgus monkeys were administered weekly doses of 10 or 100 mg/kg NOV1401 s.c. for 13 weeks (14 doses) or doses of 50 mg/kg NOV1401 i.v. for 4 weeks (5 doses). Animals treated with NOV1401 were exposed to NOV1401 during the dosing phase of the study; no exposure was noted in control animals. No gender-related differences in exposure to plasma total NOV1401 were observed. The increase in exposure (both $C_{max}$ and $AUC_{0-7d}$) was dose-proportional in both male and female animals (Table 10). Anti-NOV1401 antibodies were detected in 5 of 6 animals at 10 mg/kg/week s.c., in 1 of 10 animals at 100 mg/kg/week s.c., and in 1 of 6 animals at 50 mg/kg/week i.v. Exposure to total NOV1401 was not compromised in any of the s.c. dose groups. Only one anti-drug antibody (ADA)-positive animal had an $AUC_{0-7d}$ on Study Day 22 that was lower than the other animals in the same group (50 mg/kg/week i.v.). There was no impact on aPTT prolongation in this animal and no toxicity was observed.

TABLE 10

Mean toxicokinetic parameters for the penultimate dose (Study Day 85 for the s.c. arms, Study Day 22 for the i.v. arm) of 13-week/4-week GLP-compliant toxicity study in cynomolgus monkeys (male + female combined)

| Dose (mg/kg/week) | Route | $t_{max}$ (hr)* | $C_{max}$ (μg/mL) | $AUC_{0-14\,d}$ (μg · d/mL) |
|---|---|---|---|---|
| 10 | s.c. | 24-120 | 719 | 3,100 |
| 100 | s.c. | 72-120 | 5,630 | 23,400 |
| 50 | i.v. | 0.25-96 | 1,990 | 10,700 |

*$t_{max}$ is reported as the range of values observed.

Example 11

Dose Escalation Study in Humans

Human studies are carried out to assess the safety and tolerability of anti-FXI/FXIa antibodies, such as NOV1401, following single dose administration in healthy subjects. A total of approximately 60 healthy male and post-menopausal/surgically sterile female subjects, between 18 and 55 years of age, are entered into this study. Good health is determined by past medical history, physical examination, neurological examination, vital signs, electrocardiogram (ECG), and laboratory tests at screening. Selected subjects weigh at least 50 kg, and have a body mass index (BMI) within the range of 18-35 kg/m². BMI=body weight (kg)/[height (m)]².

Six s.c. dose levels of 5, 15, 50, 150, 300 and 600 mg are to be tested in a human study, provided that the predicted mean duration of aPTT prolongation ≥2-fold does not persist for ≥42 days at any tested dose. Two interim analyses (IA) are conducted to confirm dose selection for the 2 highest dose levels. If the model-predicted mean duration of aPTT prolongation is ≥2-fold for longer than 42 days at the 300 mg or the 600 mg dose, the dose can be lowered based, for example, based on model simulations, to ensure that the mean duration of aPTT prolongation does not exceed 2-fold for ≥42 days. Non-limiting exemplary dose adjustments may involve lowering a dose using decrements of 10 mg, 20 mg, 30 mg, 40 mg, or 50 mg.

The first three dose escalation steps occur at ≈½ log increments. The last 2 dose escalation steps are 2-fold increments to mitigate the risk of prolonged target saturation and extended aPTT prolongation.

The maximum duration of 2-fold aPTT prolongation for a certain number of days (e.g., 30 days, 35 days, 40 days, 42 days, etc.) with a therapy targeting FXI can be assessed based on genetic data showing mild bleeding phenotype in patients with severe FXI deficiency, data from patients with FXI deficiency with acquired inhibitor, and also data from human studies, for instance, FXI-ASO (see, e.g., Liu et al., (2011) "ISIS-FXIRx, a novel and specific antisense inhibitor of factor XI, caused significant reduction in FXI antigen and activity and increased aPTT without causing bleeding in healthy volunteers." Presented at the 53rd American Society of Hematology annual meeting and exposition, San Diego, Calif. Blood; 118: Abstract 209), where multiple dose administration of FXI-ASO over 6 weeks resulted in a robust and sustained FXI depletion over >6 weeks (42 days) with no bleeding events. In certain embodiments, a model-based analysis predicts that maximum aPTT prolongation of ≈2.7-fold (relative to pre-dose) can be achieved transiently at a 50 mg s.c. dose of NOV1401 (60-kg subject). In certain embodiments, higher doses are predicted to extend the duration of this maximum aPTT prolongation of 2.7 fold.

Subjects are monitored throughout the study for safety parameters and/or end points, such as, physical exam, neurological exam, vital signs, electrocardiogram (ECG), safety laboratories, and adverse events (AEs) including serious AEs (SAEs) up until and including Day 106 post-dose.

The effect of anti-FXI/FXIa antibody (e.g., NOV1401) on aPTT is assessed based on relative changes from baseline. Plasma concentrations of total anti-FXI/FXIa antibody (e.g., NOV1401) are measured to assess the PK of single doses in these subjects.

To assess immunogenicity (IG) of anti-FXI/FXIa antibodies (e.g., NOV1401), screening and confirmation for ADA are conducted.

Free and total FXI and FXI coagulation activity (FXI:C) are measured to assess the effects of anti-FXI/FXIa antibodies (e.g., NOV1401) on target engagement and target-related PD parameters.

D-dimer, prothrombin fragments 1.2 (F1.2) and prothrombin-antithrombin complex (TAT) are assessed to determine the effects of anti-FXI/FXIa antibodies (e.g., NOV1401) on thrombogenesis parameters.

To study the effects of anti-FXI/FXIa antibodies (e.g., NOV1401) on other coagulation parameters, the following can be assessed: prothrombin time (PT), thrombin time (TT), and exploratory coagulation laboratory parameters such as thrombin activatable fibrinolysis inhibitor, fibrinogen, tissue plasminogen activator (tPA) and TGA in the subjects.

Biomarkers studied may include, but are not be limited to: D-Dimer, FXI activity, PT/INR, TT, F1.2, fibrinogen, TGA, TAFI activity, TAT, PAI-1 antigen, TFPi activity, tPA activity, and vWF activity.

INCORPORATION BY REFERENCE

All references cited herein, including patents, patent applications, papers, publications, text books, and the like, and the references cited therein, to the extent that they are not already, are hereby incorporated herein by reference in their entirety.

EQUIVALENTS

The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

The invention claimed is:

1. An isolated anti-Factor XI (FXI) antibody or a fragment thereof which specifically binds to the catalytic domain of FXI, wherein said antibody or fragment comprises (i) a light chain variable region (VL) comprising complementarity determining regions LCDR1, LCDR2, and LCDR3 of SEQ ID NO: 39, and (ii) a heavy chain variable region (VH) comprising complementarity determining regions HCDR1, HCDR2, and HCDR3 of SEQ ID NO: 29.

2. The isolated antibody or fragment of claim 1, wherein the antibody or fragment comprises a VH comprising the amino acid sequence of SEQ ID NO: 29 and a VL comprising the amino acid sequence of SEQ ID NO: 39.

3. The isolated antibody or fragment of claim 1, wherein the the HCDR1 comprises the amino acid sequence of SEQ ID NO: 46; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 33; the LCDR2 comprises the amino acid sequence of SEQ ID NO: 14; and the LCDR3 comprises the amino acid sequence of SEQ ID NO: 15.

4. The isolated antibody or fragment of claim 1, wherein the HCDR1 comprises the amino acid sequence of SEQ ID NO: 23; the HCDR2 comprises the amino acid sequence of SEQ ID NO: 24; The HCDR3 comprises the amino acid sequence of SEQ ID NO: 25; the LCDR1 comprises the amino acid sequence of SEQ ID NO: 33; the LCDR2 comprises the amino acid sequence of SEQ ID NO: 34; and the LCDR3 comprises the amino acid sequence of SEQ ID NO: 35.

5. The isolated antibody or fragment of claim 1, wherein the HCDR1 comprises the amino acid sequence of SEQ ID NO: 26; the HCDR2 comprises the amino acid sequence of SEQ ID NO: 27; the HCDR3 comprises the amino acid sequence of SEQ ID NO: 28; the LCDR1 comprises the amino acid sequence of SEQ ID NO: 36; the LCDR2 comprises the amino acid sequence of SEQ ID NO: 37; and the LCDR3 comprises the amino acid sequence of SEQ ID NO: 38.

6. A pharmaceutical composition comprising an antibody or fragment thereof of claim 1 and a pharmaceutically acceptable carrier.

7. The isolated antibody or fragment of claim 1, wherein the HCDR1 comprises the amino acid sequence of SEQ ID NO: 43; the HCDR2 comprises the amino acid sequence of SEQ ID NO: 44; the HCDR3 comprises the amino acid sequence of SEQ ID NO: 45; the LCDR1 comprises the amino acid sequence of SEQ ID NO: 47; the LCDR2 comprises the amino acid sequence of SEQ ID NO: 37; and the LCDR3 comprises the amino acid sequence of SEQ ID NO: 15.

8. The isolated antibody or fragment of claim 1, wherein the VH comprises the amino acid sequence of SEQ ID NO: 9 and the VL comprises the amino acid sequence of SEQ ID NO: 19.

9. An isolated anti-FXI antibody or a fragment thereof which specifically binds to the catalytic domain of FXI, wherein the antibody comprises a heavy chain comprising the amino acid sequence of SEQ ID NO: 31 and a light chain comprising the amino acid sequence of SEQ ID NO: 41.

10. The isolated antibody or fragment of claim 1, wherein the antibody comprises a heavy chain comprising the amino acid sequence of SEQ ID NO: 11 and a light chain comprising the amino acid sequence of SEQ ID NO: 21.

11. The antibody or fragment of claim 1, which is a human monoclonal antibody.

12. The antibody or fragment of claim 1, which is a single chain antibody, Fab fragments, Fv fragment, F(ab')2 fragment, or scFv fragment.

13. The antibody or fragment of claim 1, which is a human IgG1 isotype.

14. A pharmaceutical composition comprising the antibody or fragment thereof of claim 2 and a pharmaceutically acceptable carrier.

15. A pharmaceutical composition comprising the antibody or fragment thereof of claim 9 and a pharmaceutically acceptable carrier.

16. The isolated antibody or fragment of claim 1, wherein the VH comprising an amino acid sequence that is at least 95% identical to the amino acid sequence of SEQ ID NO: 29 and the VL comprises an amino acid sequence that is at least 95% identical to the amino acid sequence of SEQ ID NO: 39.

* * * * *